(12) United States Patent
Youdim et al.

(10) Patent No.: US 8,685,955 B2
(45) Date of Patent: Apr. 1, 2014

(54) NEUROPROTECTIVE IRON CHELATORS AND PHARMACEUTICAL COMPOSITIONS COMPRISING THEM

(75) Inventors: Moussa B. H. Youdim, Haifa (IL); Matitiyahu Fridkin, Rehovot (IL); Hailin Zheng, Rehovot (IL); Abraham Warshawsky, Rehovot (IL); Rivka Warshawsky, legal representative, Jaffe (IL)

(73) Assignees: Technion Research and Development Foundation Ltd., Haifa (IL); Yeda Research and Development Co. Ltd., Rehovot (IL)

(*) Notice: Subject to any disclaimer, the term of this patent is extended or adjusted under 35 U.S.C. 154(b) by 167 days.

(21) Appl. No.: 13/296,061

(22) Filed: Nov. 14, 2011

(65) Prior Publication Data

US 2012/0058945 A1 Mar. 8, 2012

Related U.S. Application Data

(62) Division of application No. 10/534,357, filed as application No. PCT/IL03/00932 on Nov. 7, 2003, now Pat. No. 8,058,442.

(60) Provisional application No. 60/424,313, filed on Nov. 7, 2002, provisional application No. 60/504,126, filed on Sep. 22, 2003.

(51) Int. Cl.
| | |
|---|---|
| A61K 38/09 | (2006.01) |
| A61P 5/02 | (2006.01) |
| A61K 38/22 | (2006.01) |
| C07K 14/575 | (2006.01) |
| A61K 38/00 | (2006.01) |
| A61P 3/04 | (2006.01) |
| A61P 25/00 | (2006.01) |
| A61P 25/28 | (2006.01) |
| C07K 14/70 | (2006.01) |
| A61K 31/50 | (2006.01) |
| A61K 31/501 | (2006.01) |
| A01N 43/42 | (2006.01) |
| A61K 31/47 | (2006.01) |
| A01N 43/40 | (2006.01) |
| A61K 31/44 | (2006.01) |
| A61K 38/04 | (2006.01) |
| C07K 5/00 | (2006.01) |
| C07K 7/00 | (2006.01) |
| C07K 16/00 | (2006.01) |
| C07K 17/00 | (2006.01) |

(52) U.S. Cl.
USPC ........ 514/183; 514/10.3; 514/13.1; 514/17.7; 514/17.8; 514/18.5; 514/252.1; 514/311; 514/345; 514/348; 530/327; 530/328; 530/330

(58) Field of Classification Search
None
See application file for complete search history.

(56) References Cited

U.S. PATENT DOCUMENTS 6,855,711 B1 2/2005 Warshawsky et al.

FOREIGN PATENT DOCUMENTS

| EP | 1006108 A1 | 6/2000 |
| JP | 58174318 A1 | 10/1983 |
| JP | 2002500663 A1 | 12/1998 |
| JP | 2001521924 T | 11/2001 |
| RO | 63861 | 9/1978 |
| WO | 00/74664 A2 | 12/2000 |
| WO | 2004007461 A1 | 1/2004 |

OTHER PUBLICATIONS

Khatuya et al., Arylpiperazine substituted heterocycles as Selective α1a adrenergic antagonists, Bioorganic & Medicinal Chemistry Letters, vol. 12, Issue 17, Sep. 2, 2002, pp. 2443-2446 (available online Aug. 3, 2002).*
Youdim & Wadia The Anti-Parkinson Drug Rasagiline and Its Cholinesterase Inhibitor Derivatives Exert Neuroprotection Unrelated to MAO Inhibition in Cell Culture and in Vivo, Annals of the New York Academy of Sciences vol. 939, Issue 1, Jun. 2001.*
Youdim & Weinstock., Molecular Basis of Neuroprotective Activities of Rasagiline and the Anti-Alzheimer Drug TV3326 [(N-Propargyl-(3R)Aminoindan-5-YL)-Ethyl Methyl Carbamate] Cellular and Molecular Neurobiology, vol. 21, No. 6, Dec. 2001.*
Zhang et al., "Neuroprotection by iron chelator against proteasome inhibitor-induced nigral degeneration" Biochem Biophys Res Comm, pp. 544-549, vol. (2) (2005).
Burckhalter et al. "Amino- and Chloromethylation of 8-Quinolinol. Mechanism of Preponderant ortho Substitution in Phenols under Mannich Conditions", Jounal of Organic Chmistry 26 pp. 4078-4083 (1961).
Matsumura et al. "3-[8'-Quinolinol (5')-yl]alanine and related compounds" Bulletin of the chemical society of Japan 42 (6), pp. 1741-1743 (1969).

(Continued)

Primary Examiner — Jeffrey S. Lundgren
Assistant Examiner — William Lee
(74) Attorney, Agent, or Firm — Browdy and Neimark, PLLC

(57) ABSTRACT

Novel iron chelators exhibiting neuroprotective and good transport properties are useful in iron chelation therapy for treatment of a disease, disorder or condition associated with iron overload and oxidative stress, e.g., a neurodegenerative or cerebrovascular disease or disorder, a neoplastic disease, hemochromatosis, thalassemia, a cardiovascular disease, diabetes, an inflammatory disorder, anthracycline cardiotoxicity, a viral infection, a protozoal infection, a yeast infection, retarding aging, and prevention and/or treatment of skin aging and skin protection against sunlight and/or UV light. The iron chelator function is provided by a 8-hydroxyquinoline, a hydroxypyridinone or a hydroxamate moiety. The neuroprotective function is imparted to the compound, e.g., by a neuroprotective peptide. A combined antiapoptotic and neuroprotective function is provided by a propargyl group.

9 Claims, 15 Drawing Sheets

(56) References Cited

OTHER PUBLICATIONS

Sparrow, James T. "Synthesis of substituted quinolinols. II" Journal of Heterocylic Chemistry 8(3), pp. 477-478 (1971).

Walkup G.K. "Stereoselective Synthesis of Fluorescent α-Amino Acids Containing Oxine (8-Hydroxyquinoline) and Their Peptide Incorporation in Chemosensors for Divalent Zinc", Journal of Organic Chemistry 63(19), pp. 6727-6731 (1998).

Supplemental European Search Report for European Application No. EP 03773953.9, dated Dec. 3, 2010.

Shatemirova et al. "Effect of New Derivatives of 2-Propynylamine on the Activity of Mitochondrial Monoaminooxidase", Voprosy Meditsinskoi Khimii 23(5), pp. 609-18 (1977) (Complete English Translation).

Kirienko et al. "Derivatives of 8-Hydroxyquinoline as Possible Anthelmintics, Nematocides, and Fungicides" Izv. Akad. Nauk Mold. SSR, Ser. Biol. Khirn. Nauki, No. 10. pp. 55-62 (1967). (Full Russian Text. English Langauge abstract previously submitted on Dec. 22, 2010).

* cited by examiner

NEUROPROTECTIVE IRON CHELATORS AND PHARMACEUTICAL COMPOSITIONS COMPRISING THEM

FIELD OF THE INVENTION

The present invention relates to amphiphilic metal chelators that have specificity for iron and are useful for treatment of diseases, disorders and conditions by iron chelation therapy. In one aspect, the iron chelators are designed to provide desired cell membrane, particularly blood-brain-barrier (BBB), transport properties in lipophilic media. In another aspect, these chelators are part of multifunctional compounds possessing an iron chelator function and a residue that imparts a neuroprotective function and/or a residue that imparts both antiapoptotic and neuroprotective functions. The invention further relates to pharmaceutical compositions and methods for treatment and/or prevention of diseases, disorders and conditions associated with iron overload and oxidative stress, in particular neurodegenerative diseases, conditions and disorders such as Parkinson's disease, Alzheimer's disease, stroke, amyotrophic lateral sclerosis (ALS), multiple sclerosis, Friedreich's ataxia, Hallervorden-Spatz disease, epilepsy and neurotrauma.

BACKGROUND OF THE INVENTION

Iron is known to enhance the production of the highly reactive and toxic hydroxyl radical, thus stimulating oxidative damage. Iron has been associated with a number of diseases, disorders and conditions because humans have no physiologic means of eliminating excess iron.

Hereditary hemochromatosis, a condition in which the body accumulates excess amounts of iron, is one of the most common genetic diseases in humans. In the United States, as many as one million people have evidence of hemochromatosis, and up to one in every ten people may carry the gene for the disorder. Hemochromatosis is characterized by lifelong excessive absorption of iron from the diet, with iron accumulating in body organs, eventually causing inflammation and damage. Serious and even fatal health effects can result, including cirrhosis of the liver, liver cancer, heart abnormalities (leading to heart failure), diabetes, impotence, and arthritis.

Clinical thalassemia (major and minor) are hereditary disorders characterized by defective production of hemoglobin, which leads to decreased production and increased destruction of red blood cells. With severe thalassemia, regular blood transfusions and folate supplementation are given, resulting in iron overload. Since iron is usually not ingested in large amounts, the body holds onto what it receives and has no way of ridding itself of any excess. Iron overload is therefore the leading cause of death among thalassemia patients in industrialized nations.

Patients with b-thalassemia major (TM) or refractory anemia (as in myelodysplastic syndrome) who receive frequent or regular red-cell transfusions, coupled with increased iron absorption due to ineffective erytropoiesis, develop iron overload rapidly. The toxicity of iron begins when its load exceeds the tissue or blood binding capacity to join a mobile intracellular or free nontransferrin-bound pool in the blood, the unbound iron accelerates hydroxyl radical formation resulting in peroxidative damage to cells. In the absence of chelation therapy, chronically transfused patients inevitably undergo progressive deterioration in pancreatic, hepatic and cardiac function, and usually succumb to life-threatening arrhythmias or intractable heart failure as a result of iron overload. This usually happens in the second decade of life in poorly or unchelated patients with thalassemia major.

Deferoxamine (DFO), a naturally occurring siderophore, chelating iron in a labile intracellular pool that is itself rapidly renewed from the storage pool, was introduced in early 1960s. The minimal absorption of DFO from the gastrointestinal tract and its short half-life in the blood necessitate a slow prolonged parenteral administration of the drug to achieve net negative iron balance as the prime goal of an effective chelation therapy. The expense and inconvenience of DFO has led to a search for an orally-active iron chelator, and deferiprone (L1) has been used in the last years for oral treatment of thalassemia major patients, but the risk of agranulocytosis mandates a careful evaluation of the use of this drug. Other orally active iron chelators have reached clinical trials in the past decade but their use in iron chelation therapy need more investigation. The identification of suitable, preferably orally, effective iron chelators for the treatment of iron overload diseases, disorders and conditions still remains an unsolved problem.

Neurodegenerative diseases, such as Parkinson's disease (PD) and Alzheimer's disease (AD), are neurodegenerative syndromes for which at present no cure is available. Both diseases are the most widespread neurodegenerative disorders. They affect approximately 0.5% and 4-8%, respectively, of the population over the age of 50 years, thereby, considering the still growing number of the elderly, forming an increasing economic burden for society. Therefore, development of an effective drug for preventing (neuroprotective) and treating neurodegenerative diseases is essential for the whole society.

Numerous studies including in vivo, in vitro and relevant animal models have shown a linkage between free radical production and neurodegenerative diseases and disorders, such as Parkinson's diseases, Alzheimer's disease and stroke as well as ALS, multiple sclerosis, Friedreich's ataxia, Hallervorden-Spatz disease, epilepsy and neurotrauma.

For this reason, 8-hydroxyquinolines and hydroxypyridinones have been proposed for iron binding as antioxidant-type drugs. Since iron accumulation in neurodegenerative diseases is a common feature, the inventors have shown previously that it has a pivotal role in the process of neurodegenration (Youdim, 1988). We (Gassen and Youdim, 1999) and others (Cuajungco et al., 2000; Sayre et al., 2000) have suggested on several occasions the development of iron chelators as therapeutic agents for Alzheimer's disease and Parkinson's disease.

In Parkinson's disease, the brain defensive mechanisms against the formation of oxygen free radicals are defective. In the substantia nigra of parkinsonian brains there are reductions in activities of antioxidant enzymes. Moreover, iron concentrations are significantly elevated in parkinsonian substantia nigra pars compacta and within the melanized dopamine neurons. Latest studies have also shown that significant accumulations of iron in white matter tracts and nuclei throughout the brain precede the onset of neurodegeneration and movement disorder symptoms. Indeed the accumulation of iron at the site of neurodegeneration is one of the mysteries of neurodegenerative diseases because iron does not cross the BBB. Where the iron comes from and why it accumulates is not known.

The etiology of Alzheimer's disease (AD) and the mechanism of cholinergic neuron degeneration remain elusive. Nevertheless, the chemical pathology of AD shows many similarities to Parkinson's disease: the involvement of increased iron, release of cytochrome C, increased alpha-synuclein aggregation, oxidative stress, loss of tissue reduced glutathione (GSH), an essential factor for removal of hydrogen peroxide, reduction in mitochondrial complex I activity, increased lipid peroxidation, and loss of calcium-binding protein 28-kDa calbindin, to mention a few. These similarities also include the progressive nature of the disease, proliferation of reactive microglia around and on top of the dying neurons, the onset of oxidative stress and inflammatory processes.

Oxygen free radicals have been shown to be associated with protein denaturation, enzyme inactivation, and DNA damage, resulting in lipid peroxidation of cell membranes, and finally the cell death in neurodegenerative diseases. One of the profound aspects of neurodegenerative diseases is the accumulation and deposition of significant amount of iron at the neurodegenerative sites. In AD, iron accumulates within the microglia and within the neurons and in plaques and tangles. Current reports have provided evidence that the pathogenesis of AD is linked to the characteristic neocortical beta-amyloid deposition, which may be mediated by abnormal interaction with metals such as iron. Indeed, iron is thought to cause aggregation of not only beta-amyloid protein but also of alpha-synuclein, promoting a greater neurotoxicity. This has led to the notion that chelatable free iron may have a pivotal role in the induction of the oxidative stress and the inflammatory process leading to apoptosis of neurons. Iron and radical oxygen species activate the proinflammatory transcription factor, NFκB, which is thought to be responsible for promotion of the cytotoxic proinflammatory cytokines IL-1, IL-6 and TNF-alpha, which increase in AD brains is one feature of AD pathology. This is considered logical since iron, as a transition metal, participates in Fenton chemistry with hydrogen peroxide to generate the most reactive of all radical oxygen species, reactive hydroxyl radical. This radical has been implicated in the pathology of cell death and mechanism of action of numerous toxins and neurotoxins (6-hydroxydopamine, MPTP, kainite, streptocozin model of AD). Furthermore, such toxins mimic many of the pathologies of neurodegenerative diseases (AD, Parkinson's disease and Huntington's Chorea), one feature of which is the accumulation of iron, but not of other metals, at the site of neurodegeneration.

Iron alone or iron decompartmentalized from its binding site by a neurotoxin, e.g. the dopaminergic neurotoxin 6-hydroxydopamine (6-OHDA), may induce oxidative stress and neurodegeneration, as evidenced in previous studies of the inventors in which intranigral administration of iron-induced "Parkinsonism" in rats and the iron chelator desferrioxamine protected the rats against 6-OHDA-induced lesions of nigrostrial dopamine neurons (Ben-Shachar et al., 1991). It has thus been suggested that treatment or retardation of the process of dopaminergic neurodegeneration in the substantia nigra may be affected by iron chelators capable of crossing the blood brain barrier in a fashion similar to the copper chelator D-penacillamine used in the treatment of Wilson's disease. This therapeutic approach for the treatment of Parkinson's disease can be applied to other metal-associated neurological disorders such as tardive dyskinesia, Alzheimer's and Hallervorden-Spatz diseases.

Stroke is the third leading cause of death in the Western world today, exceeded only by heart diseases and cancer. The overall prevalence of the disease is 0.5-0.8% of the population. Stroke is characterized by a sudden appearance of neurological disorders such as paralysis of limbs, speech and memory disorders, sight and hearing defects, etc., which result from a cerebrovascular damage.

Haemorrhage and ischemia are the two major causes of stroke. The impairment of normal blood supply to the brain is associated with a rapid damage to normal cell metabolism including impaired respiration and energy metabolism lactacidosis, impaired cellular calcium homeostasis release of excitatory neurotransmitters, elevated oxidative stress, formation of free radicals, etc. Ultimately these events lead to cerebral cell death and neurological disfunction.

Treatment of stroke is primarily surgical. Much effort is being invested in less aggressive therapeutical intervention in the search for drugs which are capable of restoring normal blood perfusion in the damaged area as well as drugs which are designed to overcome the above listed damaging events associated with cellular damage.

Oxidative stress and free radical formation play a major role in tissue injury and cell death. These processes are catalyzed by transient metal ions, mainly iron and copper. In the case of stroke, since vascular damage is involved, iron is available for the free radical formation, a process that could be prevented by iron chelators. Indeed, with lazaroides (21-amino steroids), known free radical scavengers, a significant improvement of local and global ischemia damages induced in animals has been achieved.

Iron chelators and radical scavengers have been shown to have potent neuroprotective activity in animal models of neurodegeneration. However, the major problem with such compounds is that they do not cross the BBB. The prototype iron chelator Desferal (desferrioxamine) was first shown by us to be a highly potent neuroprotective agent in animal models of Parkinson's disease (Ben-Schachar et al., 1991). However, Desferal does not cross the BBB and has to be injected centrally. Desferal also protects against streptozocin model of diabetes.

Free radicals in living organism are believed to be produced by the reaction of transition metal ions (especially copper and iron) with poorly reactive species such as $H_2O_2$, $[O_2.^-]$, thiols, lipid peroxides. Antioxidant metal chelators, by binding free metal ions (especially copper and iron) or metal ions from active centers of enzymes of the defense system, can influence the oxidant/antioxidant balance in vivo, and hence, may affect the process of dopaminergic and cholinergic neurodegeneration and have great therapeutic potential against neuodegenerative diseases.

Iron accumulation in aging and the resulting oxidative stress has been suggested to be a potential causal factor in aging and age-related neurodegenerative disorders (Butterfield et al., 2001). There is increasing evidence that reactive oxygen species play a pivotal role in the process of ageing and the skin, as the outermost barrier of the body, is exposed to various exogenous sources of oxidative stress, in particular UV-irradiation. These are believed to be responsible for the extrinsic type of skin ageing, termed photo-ageing. (Podda et al., 2001). Iron chelators have thus been suggested to favor successful ageing in general, and when applied topically, successful skin ageing (Polla et al., 2003).

Iron is a factor in skin photodamage, not only in ageing, apparently by way of its participation in oxygen radical production. Certain topical iron chelators were found to be photoprotective (Bisset and McBride, 1996; Kitazawa et al., 1999). UVA radiation-induced oxidative damage to lipids and proteins in skin fibroblasts was shown to be dependent on iron and singlet oxygen (Vile and Tyrrel, 1995). Iron chelators can thus be used in cosmetic and non-cosmetic formulations, optionally with sunscreen compositions, to provide protection against UV radiation exposure.

Other diseases, disorders or conditions associated with iron overload include: (i) viral infections, including HIV infection and AIDS—oxidative stress and iron have been described to be important in the activation of HIV-1 and iron chelation, in combination with antivirals, might add to improve the treatment of viral, particularly HIV disease (van Asbeck et al., 2001); (ii) protozoal, e.g. malaria, infections; (iii) yeast, e.g. *Candida albicans*, infections; (iv) cancer—several iron chelators have been shown to exhibit anti-tumor activity and may be used for cancer therapy either alone or in combination with other anti-cancer therapies (Buss et al., 2003); (v) iron chelators may prevent cardiotoxicity induced by anthracycline neoplastic drugs (Hershko et al., 1996); (vi) inflammatory disorders—iron and oxidative stress have been shown to be associated with inflammatory joint diseases such as rheumatoid arthritis (Andrews et al., 1987; Hewitt et al., 1989; Ostrakhovitch et al., 2001); (vii) diabetes—iron chelators have been shown to delay diabetes in diabetic model rats (Roza et al., 1994); (viii) iron chelators have been described to be potential candidates for treatment of cardiovascular diseases, e.g. to prevent the damage associated with free radical generation in reperfusion injury (Hershko, 1994; Flaherty et al., 1991); (ix) iron chelators may be useful ex-vivo for preservation of organs intended for transplantation such as heart, lung or kidney (Hershko, 1994).

One of the main problems in the use of chelating agents as antioxidant-type drugs is the limited transport of these ligands or their metal complexes through cell membranes or other biological barriers.

Drugs with the brain as the site of action should, in general, be able to cross the blood brain barrier (BBB) in order to attain maximal in vivo biological activity. The efficacy of the best established iron-chelating drug, Desferal, in the neurodegenerative diseases, is limited by its ineffective transport property and high cerebro- and oculotoxicity.

8-Hydroxyquinoline is a strong chelating agent for iron, and contains two aromatic rings, which can scavenge free radicals by themselves. In our previous PCT Publication No. WO 00/74664, various iron chelators have been disclosed and their action in Parkinson's disease prevention has been shown. The lead compound, 5-[4-(2-hydroxyethyl)piperazin-1-ylmethyl]-8-hydroxyquinoline (herein referred to as VK-28), was able to cross the BBB and was shown to be active against 6-hydroxydopamine (6-OHDA) in an animal model of Parkinson's disease.

It would be very desirable to provide novel iron chelators that exhibit also neuroprotective activity and/or good transport properties through cell membranes including the blood brain barrier.

SUMMARY OF THE INVENTION

The present invention relates to amphiphilic metal chelators that have specificity for iron and exhibit neuroprotective and/or good transport properties in lipophilic media.

In one aspect, the invention provides a compound comprising an iron chelator function and a residue selected from the group consisting of a residue that imparts a neuroprotective function to the compound, a residue that imparts combined antiapoptotic and neuroprotective functions to the compound, or both, and pharmaceutically acceptable salts thereof.

The iron chelator function is provided preferably by a 8-hydroxyquinoline residue, a hydroxamate residue, or a pyridinone residue, the neuroprotective function may be provided by a cysteine or alanine residue or by the residue of a neuroprotective peptide, a neuroprotective analog or a neuroprotective fragment thereof, and the combined antiapoptotic and neuroprotective functions is preferably provided by a propargyl group.

In another aspect, the invention provides compounds of the formulas I to IV as defined hereinafter in the description and in the claims, and pharmaceutically acceptable salts thereof.

The compounds of the present invention are useful for treatment and/or prevention of diseases, disorders and conditions associated with iron overload and oxidative stress such as, but not limited to, neurodegenerative and cerebrovascular diseases and disorders, neoplastic diseases, hemochromatosis, thalassemia, cardiovascular diseases, diabetes, inflammatory disorders, anthracycline cardiotoxicity, viral, protozoal and yeast infections, for retarding ageing, and for prevention and/or treatment of skin ageing and/or skin damage associated with skin ageing and/or exposure to sunlight and/or UV light.

In a further aspect, the present invention provides a pharmaceutical composition comprising a pharmaceutically acceptable carrier and a compound of the invention.

In yet another aspect, the present invention provides a cosmetic composition comprising a compound of the invention.

In still a further aspect, the present invention provides the use of a compound of the invention for the preparation of a pharmaceutical composition for iron chelation therapy.

In still another aspect, the present invention provides a method for iron chelation therapy which comprises administering to an individual in need thereof an effective amount of a compound of the invention or of a pharmaceutically acceptable salt thereof.

BRIEF DESCRIPTION OF THE FIGURES

The formulas of the compounds defined by the adopted designation used in the description of the specification and in the claims appear in the Appendices I to VI at the end of the description, just before the claims.

DETAILED DESCRIPTION OF THE INVENTION

Figure 1A:
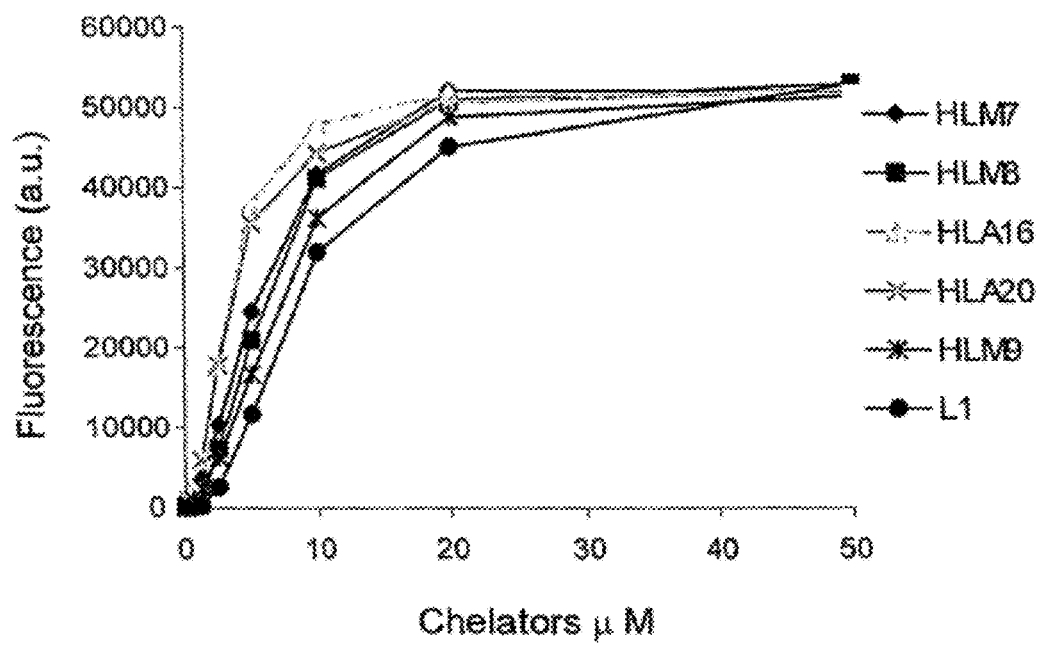
FIGS. 1A-1C are graphs showing iron chelation (in solution) by the chelators of the invention HLM7, HLM8, HLM9, HLA16, HLA20 (FIG. 1A), HLA16, HLA20, M9, M10 (FIG. 1B), and M7, M11, M12 (FIG. 1C), and the known iron chelators deferiprone (L1) and VK-28, using iron precomplexed calcein (Fe-CAL) solutions.

In one broad aspect, the present invention provides a compound comprising iron chelator function and a residue selected from the group consisting of a residue that imparts a neuroprotective function to the compound, a residue that imparts combined antiapoptotic and neuroprotective functions to the compound, or both.

In one most preferred embodiment, the residue imparting combined antiapoptotic and neuroprotective functions is a propargyl moiety, described recently as playing a crucial role in the antiapoptotie and neuroprotective effects of anti-Parkinson drug rasagiline [N-propargyl-(1R)-aminoindan] (Yogev-Falach et al., 2003).

The iron chelator function in the compounds of the invention is provided by a residue selected from the group consisting of a 8-hydroxyquinoline residue, a hydroxamate residue, and a pyridinone residue.

In one preferred embodiment, the iron chelator function is provided by a 8-hydroxyquinoline group to which the residue imparting the neuroprotective function and/or combined antiapoptotic and neuroprotective functions may be linked through the 5, 6 or 7 position of the quinoline ring. In a more preferred embodiment, the iron-chelating group is the 8-hydroxy-5-quinolinyl group of the formula below and, most preferably, it is a 8-hydroxy-5-quinolinylmethylene group.

In another preferred embodiment, the iron chelator function is provided by or a 3-hydroxypyridin-4-one or 1-hydroxypyridin-2-one of the formulas below:

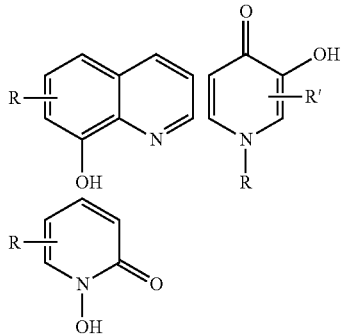

In the formulas above, R represents the group carrying the neuroprotective function and/or combined neuroprotective and antiapoptotic functions that may be linked at position 5, 6 or 7 of the quinoline ring, at position 1, 2, 5 or 6 of the 3-hydroxy-4-pyridinone ring that may be further substituted by a lower alkyl, preferably, methyl group, and at position 4 or 5 of the 1-hydroxy-2-pyridinone ring. In one preferred embodiment, the iron-chelating function is provided by a 2-methyl-3-hydroxy-4-pyridinone group substituted at position 1 by the desired further functions.

The proposed N-hydroxypyridin-2-ones and 3-hydroxypyridin-4-ones are a suitable type of candidate iron chelators for three reasons: (1) hydroxypyridinones are the most promising oral iron chelators considering both their properties and the results of biological trials—one hydroxypyridinone, deferiprone (CP20 or L1), is an orally iron chelating agent which is used worldwide in thalassaemia, cancer, leukaemia, haemodialysis and other patients (Kontoghiorghes, 2001); (2) some hydroxypyridinones, for example CP20, CP24, CP94, have been proved to be able to cross the BBB (Crivori et al., 2000); and (3) there are many structural similarities between hydroxypyridinones with catechol, an iron chelator group in the DOPA structure.

In another embodiment, the iron-chelating function is provided by a hydroxamate group. Hydroxamtes are known as iron chelators. For decades, desferrioxamine B (Desferal) has been the therapeutic iron chelator of choice for iron-overload treatment, despite numerous problems associated with its use.

In one embodiment of the invention, the residue imparting a neuroprotective function to the compound of the invention is selected from the group consisting of a neuroprotective peptide, a neuroprotective analog and a neuroprotective fragment thereof.

The neuroprotective peptide that can be used in the compounds of the invention may be, without being limited to, vasoactive intestinal peptide (VIP), gonadotropin-releasing hormone (GnRH), Substance P and enkephalin.

In one preferred embodiment, the neuroprotective function is provided by the residue of VIP, GnRH, Substance P car enkephalin or a fragment thereof in which one amino acid residue is replaced by a L- or D-cysteine residue, to which the iron-chelating residue is linked via the —S— atom of the L- or D-Cys residue.

In one embodiment of the invention, the neuroprotective peptide vasoactive intestinal peptide (VIP), a basic 28 amino acid peptide, origin isolated from the gastrointestinal system, that has been shown to protect neurons the central nervous system from a variety of neurotoxic substances including the envelop protein from HIV, tetrodotoxin, and the beta amyloid peptide. The beta amyloid peptide is a major component of the cerebral, amyloid plaque in Alzheimer disease and has been shown to be neurotoxic and associated with Alzheimer disease onset and progression, VIP itself presents a limitation for clinical use as a possible neuroprotectant since it does not cross the BBB. Lipophilic derivatives of VIP, such as stearyl-VIP, do cross the BBB. However, for more efficient penetration and as well as from economical aspects, it is desirable to have much smaller molecules mimicking the parent peptide (VIP) activity while possessing better penetration through biological barriers. In the laboratory of one of the present inventors it was found that a 4-amino acids lipidic derivative of VIP (stearyl-Lys-Lys-Tyr-Leu-NH₂—SEQ ID NO:1) surpasses the activity of the parent peptide (VIP), through binding and activation of its receptor, and provides a lead compound for drug design against neurodegenerative diseases (Gozes et al., 1999).

Thus, in one embodiment of the invention, the neuroprotective function is imparted by a VIP fragment of the SEQ ID NO: 2:

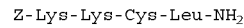

wherein Z is H or a hydrophobic group such as stearyl (St) or Fmoc.

In one embodiment, the iron chelator is a 8-hydroxyquinolinylmethyl group and the compound has the formula:

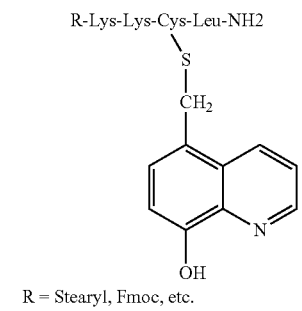

R = Stearyl, Fmoc, etc.

In this model, the peptide Lys-Lys-Tyr-Leu-NH$_2$ (SEQ ID NO:1) is the core active site for neuroprotective effect. The aromatic phenolic moiety of Tyr is substituted by an iron chelator 8-hydroxyquinoline, which serves as an antioxidative active core. The hydrophobic group R may be used to adjust the lipophilicity of the whole molecule so as to control the transport properties through the BBB.

Examples of compounds containing the above formula containing a 8-hydroxy-5-quinolinylmethyl residue (HQ) are the compounds herein designated StKKC(HQ)L (M6) and Fmoc-KKC(HQ)L (M7) in Appendix II. The corresponding compounds herein designated StKKC(HQ-Pr)L (M6A) and Fmoc-KKC(HQ-Pr)L (M7A) in Appendix I have in addition a propargylamino (Pr) group linked to the —CH$_2$ group at the 5-position of the quinoline ring.

Examples of further compounds of the invention comprising a VIP fragment analog of SEQ ID NO: 2 are the hydroxamates herein designated M6B and M7B in Appendix V that comprise also an aminopropargyl group.

Gonadotropin-releasing hormone (GnRH) is a neurohormone produced in the hypothalamic neurosecretory cells that controls release of the gonadotropins luteinizing hormone (LH) and follicle-stimulating hormone (FSH) from the anterior pituitary. The peptide was later found to function in the brain as a neurotransmitter and/or neuromodulator and to have good transport properties (GnRH is able to cross the BBB). Several GnRH analogs are now either in clinical trials or in clinical use for contraception and for the treatment of various hormone-dependent diseases including prostate and breast cancers. The combination of GnRH analogs with an iron chelator, e.g. hydroxamate, pyridinone or 8-hydroxyquinoline as an antioxidative core, is envisaged specially as protective agents in the treatment of neurodegenerative diseases.

GnRH is a decapeptide of the sequence below (the 5-oxo proline at the amino terminal is sometimes presented as pyroglutamic acid—pGlu):

```
                                        (SEQ ID NO: 3)
5-oxo-Pro-His-Trp-Ser-Tyr-Gly-Leu-Arg-Pro-Gly-NH2
```

Two analogs of GnRH were prepared in which the amino acid residue at position 5 (Tyr) or 6 (Gly) was replaced by L-Cys or D-Cys, respectively. These modifications are not expected to significantly affect the bioactivity of GnRH. Moreover these changes may generate superagonists. The free SH group of this analogs at the cysteine (5 or 6) position makes these compounds good candidates for specific chemical modifications. This change, ie, at position 6, also serves to improve the stability of the analog to proteolysis.

The resulting GnRG analogs have the sequences identified by SEQ ID NO:4 and SEQ ID NO:5, as follows:

```
                                        (SEQ ID NO: 4)
5-oxo-Pro-His-Trp-Ser-Cys-Gly-Leu-Arg-Pro-Gly-NH2

(SEQ ID NO: 5)
5-oxo-Pro-His-Trp-Ser-Tyr-D-Cys-Leu-Arg-Pro-Gly-NH2
```

To the S atom of the L-Cys or D-Cys residue the iron chelator function is attached. For example, the resulting compounds with a 8-hydroxy-5-quinolinylmethyl residue (HQ) are the compounds herein designated L-Cys[5](HQ)GnRH (M8) and D-Cys[6](HQ)GnRH (M22) in Appendix II. The corresponding compounds herein designated L-Cys[5](HQ-Pr) GnRH (M8) and D-Cys[6](HQ-Pr)GnRH (M22) in Appendix I have in addition a propargylamino (Pr) group linked to the —CH$_2$ group at the 5-position of the quinoline ring.

Examples of further compounds of the invention comprising a GnRH analog of SEQ ID NO:4 or SEQ ID NO:5 are the hydroxamates herein designated M8B and M22B in Appendix V that comprise also a propargylamino group.

According to the invention, similar Cys-containing GnRH analogs can be prepared starting from analogs of GnRH such as, but not limited to, leuprolide, nafarelin, goserelin, histrelin, and D-Lys[6]GnRH, and then attaching them to a HQ, pyridinone or hydroxamate residue and, optionally, to a propargylamino residue.

Substance P (SP) is a peptide neurotransmitter widely distributed in the peripheral and central nervous systems of vertebrates. SP is involved in modulating neuronal nicotinic acetylcholine receptors (nAChRs) in the sympathetic nervous system. Substance P analogs may be useful as drugs in control of neurodegenerative diseases.

Substance P is a undecapeptide of the sequence:

```
                                        (SEQ ID NO: 6)
Arg-Pro-Lys-Pro-Gln-Gln-Phe-Phe-Gly-Leu-Met-NH2
```

Two analogs of Substance P were prepared in which the amino acid residue at position 7 (Phe) or 8 (Phe) was replaced by Cys, resulting in the peptides of the sequences:

```
                                        (SEQ ID NO: 7)
Arg-Pro-Lys-Pro-Gln-Gln-Cys-Phe-Gly-Leu-Met-NH2

(SEQ ID NO: 8)
Arg-Pro-Lys-Pro-Gln-Gln-Phe-Cys-Gly-Leu-Met-NH2
```

To the S atom of the Cys residue the iron chelator function is attached. For example, the resulting compounds with a 8-hydroxy-5-quinolinylmethyl residue (HQ) are the compounds herein designated Cys[7](HQ)Substance-P (M27) and Cys[8](HQ) Substance-P (M28) in Appendix II. The corresponding compounds herein designated Cys[7](HQ-Pr)Substance-P (M27A) and Cys[8](HQ-Pr) Substance-P (M28A) in Appendix I have in addition a propargylamino group (Pr) linked to the —CH$_2$ group at the 5-position of the quinoline ring.

Examples of further compounds of the invention comprising a Substance-P analog of SEQ ID NO:7 or SEQ ID NO:8 are the hydroxamates herein designated M27B and M28B in Appendix V that comprise also a propargylamino group.

Met[5]-enkephalin and Leu[5]-enkephalin are two naturally occurring pentapeptides belonging to the endorphin class, of the sequences, respectively:

```
Tyr-Gly-Gly-Phe-Met            (SEQ ID NO: 9)

Tyr-Gly-Gly-Phe-Leu.           (SEQ ID NO: 10)
```

Two analogs of each of Met[5]-enkephalin (SEQ ID NO:9) and Leu[5]-enkephalin (SEQ ID NO:10) have been prepared in which either the Phe residue at position 4 or the Tyr residue at position 1 was replaced by a Cys residue, as follows:

```
Tyr-Gly-Gly-Cys-Met       (SEQ ID NO: 11)
Cys-Gly-Gly-Phe-Met       (SEQ ID NO: 12)
Tyr-Gly-Gly-Cys-Leut      (SEQ ID NO: 13)
Cys-Gly-Gly-Phe-Leu       (SEQ ID NO: 14)
```

To the S atom of the Cys residue the iron chelator function is attached. For example, the resulting compounds with a 8-hydroxy-5-quinolinylmethyl residue (HQ) are the compounds herein designated YGGC(HQ)L (M18) for SEQ ID NO: 13, YGGC(HQ)M (M19) for SEQ ID NO: 11, C(HQ)GGFL (M20) for SEQ ID NO: 14, and C(HQ)GGFM (M21) for SEQ ID NO: 12, in Appendix II. The corresponding compounds herein designated YGGC(HQ-Pr)L (M18A), YGGC(HQ-Pr)M (M19A), C(HQ-Pr)GGFL (M20A), and C(HQ-Pr)GGFM (M21A) in Appendix I have in addition a propargylamino (Pr) group linked to the —CH$_2$ group at the 5-position of the quinoline ring.

Examples of further compounds of the invention comprising an enkephalin analog of SEQ ID NO:11-14 are the hydroxamates herein designated M18BA, M19B, M20B and M21B in Appendix V that comprise also a propargylamino group.

In another embodiment of the invention, the residue imparting a neuroprotective function to the compound of the invention is selected from the group consisting of a L or D cysteine or alanine residue.

When the neuroprotective function is L- or D-cysteine, the iron chelator function is attached to the S atom of the Cys residue. For example, the resulting compounds with a 8-hydroxy-5-quinolinylmethyl residue (HQ) are the compounds herein designated D-HQ-CysOH (M11) and L-HQ-CysOH (M12) in Appendix II, and the corresponding compounds herein designated D-(HQ-Pr)-CysOH (M11a) and L-(HQ-Pr)-CysOH (M12a) in Appendix III. Examples of further compounds of the invention comprising a cysteine residue are the hydropyridinone derivatives herein designated M11b and M12b in Appendix VI that contain a propargylamino group.

Examples of compounds of the invention wherein the neuroprotective function is L- or D-alanine are the compounds with a 8-hydroxy-5-quinolinyl residue (HQ) herein designated D-HQ-Ala (M9), L-HQ-Ala (M10), the internal salt HQAla (HLM8), and the ethyl ester HQAlaEt (HLM9) in Appendix IV, and the corresponding compounds herein designated D-(HQ-Pr)-Ala (M9a), L-(HQ-Pr)-Ala (M10a), in Appendix III. A further example is the hydroxypyridinone derivative herein designated M9b in Appendix VI.

Parkinson's disease is associated with decreased dopaminergic function in the brain, and many of the symptoms of the disease can be alleviated by oral administration of L-DOPA (L-dihydroxyphenylalanine). L-DOPA is converted to dopamine by DOPA decarboxylase in the brain. Based on retrosynthesis analysis of the lead compound DOPA, which contains iron chelating group (catechol) and an amino acid (alanine), the iron-chelator-peptide and iron chelator-amino acid derivatives described above may be useful drug candidates as antioxidant-type drugs constituting another class of antiparkinsonism, and also potentially other neurodegenerative diseases and other disorders in which iron chelators are useful.

As mentioned before, drugs with the brain as the site of action should, in general, be able to cross the blood brain barrier (BBB) in order to attain maximal in vivo biological activity. When the intention is to bring to the brain iron chelators to bind and remove iron that accumulates in the brain in some neurodegenerative diseases, one of the possible solutions is to design iron-chelating molecules with specific groups, responsible for amphiphilic behavior. Such amphiphilic groups possess lipophilic and hydrophilic centers. The size and structure of both centers control the overall lipophilicity of the whole molecule, and hence its transport properties.

The present invention further provides amphiphilic metal chelators that have specificity for iron and are designed to provide desired blood brain barrier (BBB) transport properties in lipophilic media.

In one embodiment, the invention relates to compounds comprising an iron chelating residue that crosses the BBB wherein said iron chelating residue is a 8-hydroxy-5-quinolinylmethyl group linked to an aliphatic chain via a linker selected from the group consisting of an ethylenediamine moiety or a piperazine or 1,3,5-perhydrotriazine ring as shown below, but excluding the compound 5-[4-(2-hydroxyethyl)piperazin-1-ylmethyl]-8-hydroxy-quinoline.

According to this embodiment, the 8-hydroxyquinoline part of the molecule serves both as iron-specific chelator and radical-scavenger and R is an aliphatic

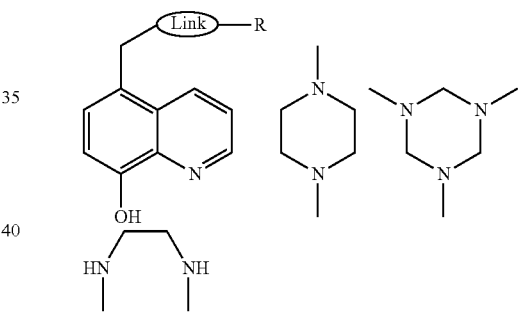

chain of different lengths, but is not a 2-hydroxyethyl group when the linker is a piperazine ring. By changing R, we can adjust the size and lipophilicity of the whole molecule, thus controlling the transport properties through the BBB. In a preferred embodiment, the linker is a piperazine ring.

The above iron chelators when the linker is piperazine may be prepared by reacting piperazine with di(t-butyl)dicarbonate (Boc$_2$O), followed by reaction of the Boc-protected piperazine with a halide R—X (R is a propargyl containing group, X is hal), removal of the Boc group with TFA, and reaction with 8-hydroxy-5-chloromethylquinoline, as described in the scheme below:

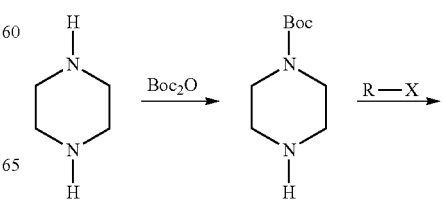

-continued

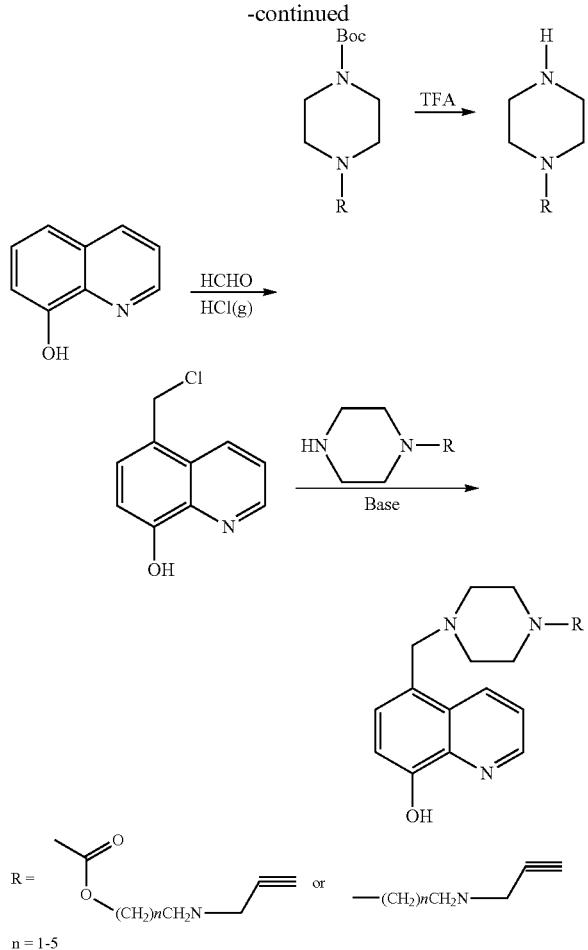

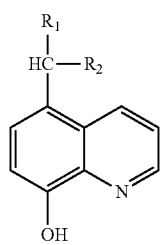

n = 1-5

The lipid solubility of the whole molecule, which is a key factor in controlling the transport property of a drug through the BBB, can be adjusted by changing n. The aliphatic chain may also contain a heteroatom selected from O, S and N. Examples of such compounds according to the invention are the compounds herein designated HLA16a, HLA20 and M17 in Appendix III. Also envisaged by the invention is Compound HLA16 in Appendix IV, that has no propargyl group.

The present invention encompasses compounds of the formulas I to IV:

-continued

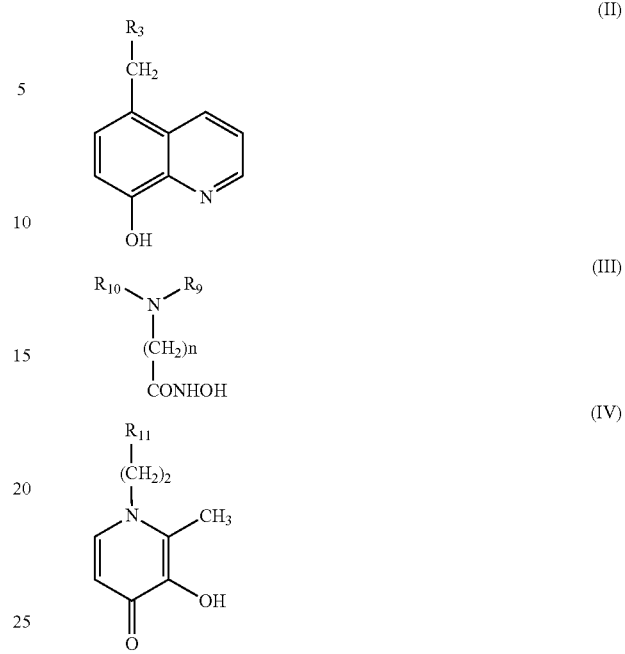

wherein $R_1$ is a residue of an analog of a neuroprotective peptide or a fragment thereof containing a cysteine residue that is linked to the C atom via the —S— atom of the Cys residue, and wherein the amino terminal of the peptide is optionally substituted by a hydrophobic group such as Fmoc or stearyl;

$R_2$ is H or —NH—X;

$R_3$ is a group selected from the group consisting of (i) —NH—CH$_2$—CH$_2$—NH—R$_4$;

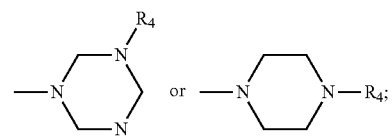

(ii) —CR$_5$R$_6$R$_7$; —N(CH$_3$)—X; (iv) —N(R$_8$)—CH(CH$_2$SH)COOC$_2$H$_5$;

(v) —N(R$_8$)—CH$_2$—COOCH$_2$C$_6$H$_5$; and (vi) —S—CH$_2$—CH(COOH)—NHR$_8$';

$R_4$ is selected from the group consisting of (i) X; (ii) COOC$_2$H$_5$;

(iii) (CH$_2$)$_2$—O—R$_8$; and (iv) —COO—(CH$_2$)$_2$—NH—R$_8$;

$R_5$ is H, C$_1$-C$_4$ lower alkyl, preferably CH$_3$, or COOC$_2$H$_5$;

$R_6$ is H, COOH, COO⁻ or COOC$_2$H$_5$;

$R_7$ is selected from the group consisting of (i) —NH—R$_8$; (ii) —NH$_3^+$;

(iii) —NH—COCH$_3$; (iv) —NH—NH—R$_8$;

and (v) —NH—NH—CO—CH(CH$_2$OH)—NH—R$_3$;

$R_8$ is H or X, and R'$_8$ is H, X, or Fmoc;

$R_9$ is selected from the group consisting of (i) H; (ii) —CO—CH$_2$—R$_1$;

(iii) —CH$_2$—COOCH$_2$C$_6$H$_5$; (iv) —CH(CH$_2$SH)COOC$_2$H$_5$;

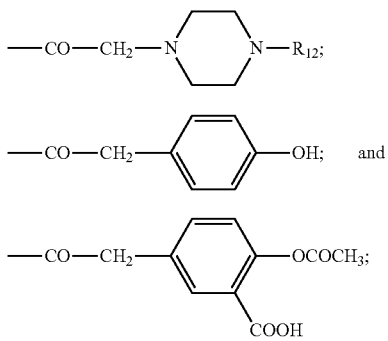

$R_{10}$ is X; —$CH_2$—CH(SH)$COOC_2H_5$; or

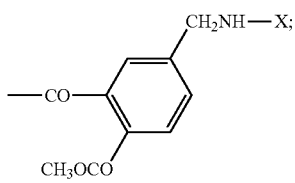

n is an integer from 1 to 6;
$R_{11}$ is a group selected from the group consisting of
(i) —S—$CH_2$—CH(COOH)—NH—X;
(ii) —N(X)—$CH_2$COO—$CH_2$—$C_6H_5$;
(iii) —N($CH_3$)—X;
(iv) (iv) —N(X)—CH($CH_2$SH)$COOC_2H_5$;
(v) —$CH_2$—NH—NH—CO—CH($CH_2$OH)—NH—X;
(vi) —C($CH_3$)(COOH)—NH—NH—X,
(vii) —CH(COOH)—NH—X;
(viii) —CH($COOC_2H_5$)—NH—X; and

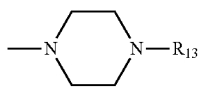

$R_{12}$ is X, $C_1$-$C_4$ lower alkyl, preferably methyl, $COOC_2H_5$, or —$(CH_2)_2$—OH;
$R_{13}$ is X, —$(CH_2)_2$—OX, or —COO—$(CH_2)_2$—NH—X; and
X is a propargyl group,
but excluding the compound 5-[4-(2-hydroxyethyl)piperazin-1-ylmethyl]-8-hydroxy-quinoline.

In one preferred embodiment, the compound of the invention is a compound of the formula I above

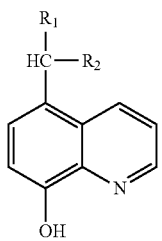

$R_1$ is a residue of an analog of a neuroprotective peptide or a fragment thereof containing a cysteine residue that is linked to the C atom via the —S— atom of the Cys residue, and wherein the amino terminal of the peptide is optionally substituted by a hydrophobic group such as Fmoc or stearyl;
$R_2$ is H or —NH—X; and
X is a propargyl group.
$R_1$ is preferably the residue of an analog of VIP, GnRH, Substance P or enkephalin or a fragment thereof in which one amino acid residue is replaced by a cysteine residue, more preferably the VIP fragment analogs of SEQ ID NO:2 that may bear a stearyl or a Fmoc group at the amino terminal, the GnRH analogs of SEQ ID NO:4 and SEQ ID NO:5, the Substance P analogs of SEQ ID NO:7 and SEQ ID NO:8, and the enkephalin analogs SEQ ID NO:11, SEQ ID NO:12, SEQ ID NO:13, and SEQ ID NO:14.

In preferred embodiments, the compounds of formula I are the compounds wherein $R_2$ is H and $R_1$ is selected from the group consisting of the residue of a VIP fragment analog of SEQ ID NO:2 bearing a stearyl (M6, Appendix II) or a Fmoc group (M7, Appendix II) at the amino terminal, the residue of a GnRH analog of SEQ ID NO:4 (M8, Appendix II) or SEQ ID NO:5 (M22, Appendix II), the residue of a Substance P analog of SEQ ID NO:7 (M27, Appendix II) or SEQ ID NO:8 (M28, Appendix II), and the residue of an enkephalin analog of SEQ ID NO:11 (M19, Appendix II), SEQ ID NO:12 (M21, Appendix II), SEQ ID NO:13 (M18, Appendix II), and SEQ ID NO:14 (M20, Appendix II).

In more preferred embodiments, the compounds of formula I are the compounds wherein $R_2$ is a propargylamino group and $R_1$ is selected from the group consisting of the residue of a VIP fragment analog of SEQ ID NO:2 bearing a stearyl (M6A, Appendix I) or a Fmoc group (M7A, Appendix I) at the amino terminal, the residue of a GnRH analog of SEQ ID NO:4 (M8A) or SEQ ID NO:5 (M22A, Appendix I), the residue of a Substance P analog of SEQ ID NO:7 (M27A, Appendix I) or SEQ ID NO:8 (M28A, Appendix I), and the residue of an enkephalin analog of SEQ ID NO:11 (M19A, Appendix I), SEQ ID NO:12 (M21A, Appendix I), SEQ ID NO:13 (M18A, Appendix I), and SEQ ID NO:14 (M20A, Appendix I).

In another preferred embodiment of the invention, there is provided a compound of formula II:

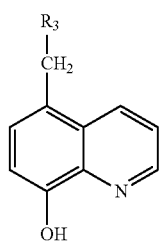

$R_3$ is a group selected from the group consisting of
(i) —NH—$CH_2$—$CH_2$—NH—$R_4$;

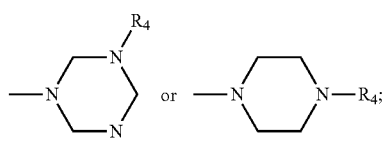

(ii) —$CR_5R_6R_7$; (iii) —N($CH_3$)—X; (iv) —N($R_8$)—CH($CH_2$SH)$COOC_2H_5$;

(v) —N($R_8$)—$CH_2$—COO$CH_2$$C_6$$H_5$; and (vi) —S—$CH_2$—CH(COOH)—NH$R_8$';

$R_4$ is selected from the group consisting of (i) X; (ii) COO$C_2$$H_5$;

(iii) $(CH_2)_2$—O—$R_8$; and (iv) —COO—$(CH_2)_2$—NH—$R_8$;

$R_5$ is H, $CH_3$ or COO$C_2$$H_5$;

$R_6$ is H, COOH, COO⁻ or COO$C_2$$H_5$;

$R_7$ is selected from the group consisting of (i) —NH—$R_8$; (ii) —$NH_3^+$;

(iii) —NH—COC$H_3$; (iv) —NH—NH—$R_8$; and (v) —NH—NH—CO—CH($CH_2$OH)—NH—$R_8$;

$R_8$ is H or X, and $R'_8$ is H, X, or Fmoc; and

X is a propargyl group, but excluding the compound 5-[4-(2-hydroxyethyl)piperazin-1-ylmethyl]-8-hydroxy-quinoline.

In a more preferred embodiment, in the compound of formula II, $R_3$ is a piperazine ring to which an aliphatic chain $R_4$ is linked to the nitrogen atom at the 4-position, but excluding the compound wherein $R_4$ is —$(CH_2)_2$—OH. This compound, 5-[4-(2-hydroxyethyl)piperazin-1-ylmethyl]-8-hydroxy-quinoline, is herein identified in Appendix IV as VK-28, and is known from WO 00/74664. In one preferred embodiment, the 8-hydroxy-5-quinolinylmethylpiperazine compounds of the invention do not contain a propargyl group ($R_4$ is —COO$C_2$$H_5$ or $R_8$ is H), as represented by the compound herein designated HLA16 (Appendix IV). In another preferred embodiment, the 8-hydroxy-5-quinolinylmethylpiperazine compounds of the invention contain a propargyl group ($R_8$ is X), as represented by the compounds herein designated HLA16a, HLA20, and M17 (Appendix In another more preferred embodiment, in the compound of formula II, $R_3$ is —S—$CH_2$—CH(COOH)—NH$R_8$', wherein $R_8$' is H, namely, $R_3$ is the residue of L-Cys or D-Cys, as represented by the compounds herein designated D-HQ-CysOH (M11, Appendix II) and L-HQ-CysOH (M12, Appendix II), or $R_8$' is propargyl, as represented by the compounds herein designated D-(HQ-Pr)-CysOH (M11a, Appendix III) and L-(HQ-Pr)-CysOH (M12a, Appendix III), or $R_8$' is Fmoc, as represented by the compounds herein designated M11B and m12B (Appendix IV).

In another more preferred embodiment, in the compound of formula II, $R_3$ is a group —C$R_5$$R_6$$R_7$, wherein $R_5$ is H, $R_6$ is COOH, and $R_7$ is —NH—$R_8$, wherein $R_8$ is H, namely, $R_3$ is the residue of L-Ala or D-Ala, as represented by the compounds herein designated D-HQ-Ala (M9, Appendix IV) and L-HQ-Ala (M10, Appendix IV); or $R_8$ is propargyl, as represented by the compounds herein designated D-(HQ-Pr)-Ala (M9a, Appendix III) and L-(HQ-Pr)-Ala (M10a, Appendix III); or $R_5$ is H, $R_6$ is COO⁻ and $R_7$ is —$NH_3^+$, as represented by the compound herein designated HQ-Ala (HLM8, Appendix IV); or $R_5$ is H, $R_6$ is COO$C_2$$H_5$ and $R_7$ is —$NH_2$, as represented by the compound herein designated HQ-AlaEt (HLM9, Appendix IV); or $R_5$ and $R_6$ are both COO$C_2$$H_5$, and $R_7$ is —NH—COC$H_3$, as represented by the compound herein designated HLM7 (Appendix IV); or $R_5$ is H, $R_6$ is COO$C_2$$H_5$ and $R_7$ is —NH-propargyl, as represented by the compound herein designated M3I (Appendix III).

In another more preferred embodiment, in the compound of formula II, $R_3$ is a group —N$R_8$—CH($CH_2$SH)COO$C_2$$H_5$, wherein $R_8$ is H or propargyl, as represented by the compounds herein designated M32 (Appendix IV) and M33 (Appendix III), respectively.

In another more preferred embodiment, in the compound of formula II, $R_3$ is a group —N($CH_3$)-propargyl, as represented by the compound herein designated M30 (Appendix III).

In still another preferred embodiment of the invention, there is provided a compound of formula III:

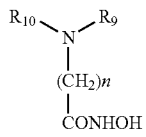

wherein $R_9$ is selected from the group consisting of (i) H; (ii) —CO—$CH_2$—$R_1$;

(iii) —$CH_2$—COO$CH_2$$C_6$$H_5$; (iv) —CH($CH_2$SH)COO$C_2$$H_5$;

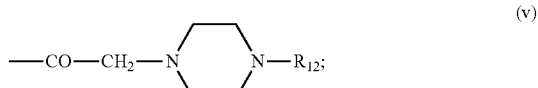

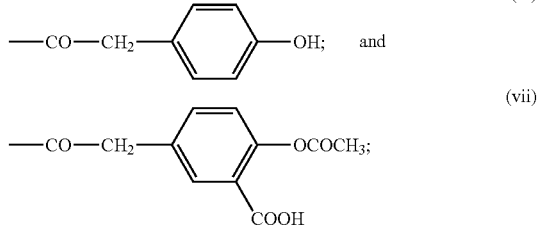

$R_{10}$ is X; —$CH_2$—CH(SH)COO$C_2$$H_5$; or

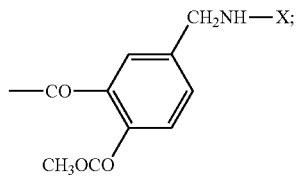

n is an integer from 1 to 6, preferably 1 or 2;

$R_{12}$ is X, $C_1$-$C_4$ lower alkyl, preferably methyl, COO$C_2$$H_5$, or —$(CH_2)_2$—OH;

and X is a propargyl group.

In one preferred embodiment, $R_9$ is —CO—$CH_2$—$R_1$, wherein $R_1$ is the residue of an analog of a neuroprotective peptide or a fragment thereof containing a Cys residue. In more preferred embodiments, the compounds of formula III are the hydroxamates containing a propargylamino group and a $R_1$ selected from the group consisting of the residue of a VIP fragment analog of SEQ ID NO:2 bearing a stearyl (M6B, Appendix V) or a Fmoc group (M7B, Appendix V) at the amino terminal, the residue of a GnRH analog of SEQ ID NO:4 (M8B, Appendix V) or SEQ ID NO:5 (M22B, Appendix V), the residue of a Substance P analog of SEQ ID NO:7 (M27B, Appendix V) or SEQ ID NO:8 (M28B, Appendix V), and the residue of an enkephalin analog of SEQ ID NO:11 (M19B, Appendix V), SEQ ID NO:12 (M21B, Appendix V), SEQ ID NO:13 (M18B, Appendix V), and SEQ ID NO:14 (M20B, Appendix V).

In other preferred embodiments, $R_9$, $R_{10}$ and $R_{12}$ are as defined above as exemplified by the compounds herein designated M35, M36, M37, M38, M39, M40, M41, M42, M43, M44, M45 and M46 (Appendix V).

In yet another preferred embodiment, there is provided a compound of formula IV:

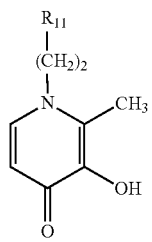

wherein
$R_{11}$ is selected from the group consisting of
(i) —S—CH$_2$—CH(COOH)—NH—X;
(ii) —N(X)—CH$_2$COO—CH$_2$—C$_6$H$_5$;
(iii) —N(CH$_3$)—X;
(iv) (iv) —N(X)—CH(CH$_2$SH)COOC$_2$H$_5$;
(v) —CH$_2$—NH—NH—CO—CH(CH$_2$OH)—NH—X;
(vi) —C(CH$_3$)(COOH)—NH—NH—X;
(vii) —CH(COOH)—NH—X;
(viii) —CH(COOC$_2$H$_5$)—NH—X; and

(ix)

$R_{13}$ is X, —(CH$_2$)$_2$—OX, or —COO—(CH$_2$)$_2$—NH—X; and

X is a propargyl group.

In preferred embodiments, the pyridinone derivatives are exemplified by the compounds herein designated M9b, M11b, M12b, M13b, M15b, HLA16b, M17a, HLA20a, M30a, M31a, M33a, and M34b, whose formulas are depicted in Appendix VI herein. Other derivatives of pyridinones may be used wherein the Me group is replaced by a different alkyl, e.g. ethyl, or the ring may contain a further alkyl group, optionally substituted.

The following Schemes A-D depict examples of methods that can be used for the preparation of compounds of the formulas I, II, III and IV. All of the starting materials are prepared by procedures described in these schemes, by procedures well known to one of ordinary skill in organic chemistry or can be obtained commercially. All of the final compounds of the present invention are prepared by procedures described in these schemes or by procedures analogous thereto, which would be well known to one of ordinary skill in organic chemistry. All the modified peptides were prepared automatically or manually by solid-phase peptide synthesis using Fmoc chemistry following the company's protocols.

The compounds of formula I can be prepared by the method as shown in Scheme A, or by the methods given in the examples or by analogous methods.

As shown in Scheme A below, 8-hydroxyquinoline (A1) is treated with hydrochloric acid and formaldehyde to give 5-chloromethyl-8-hydroxyquinoline (A2). The chloro group of A2 is substituted with propargylamine to afford 5-(1-propargylamino)methyl-8-hydroxyquinoline (A3). Bromination of A3 employing N-bromosuccinimide (NBS) provides the bromide A4 which is then treated, for example, with the modified peptide [D-Cys$^6$]GnRH to give the target compound A5, which is the compound M22A in Appendix I.

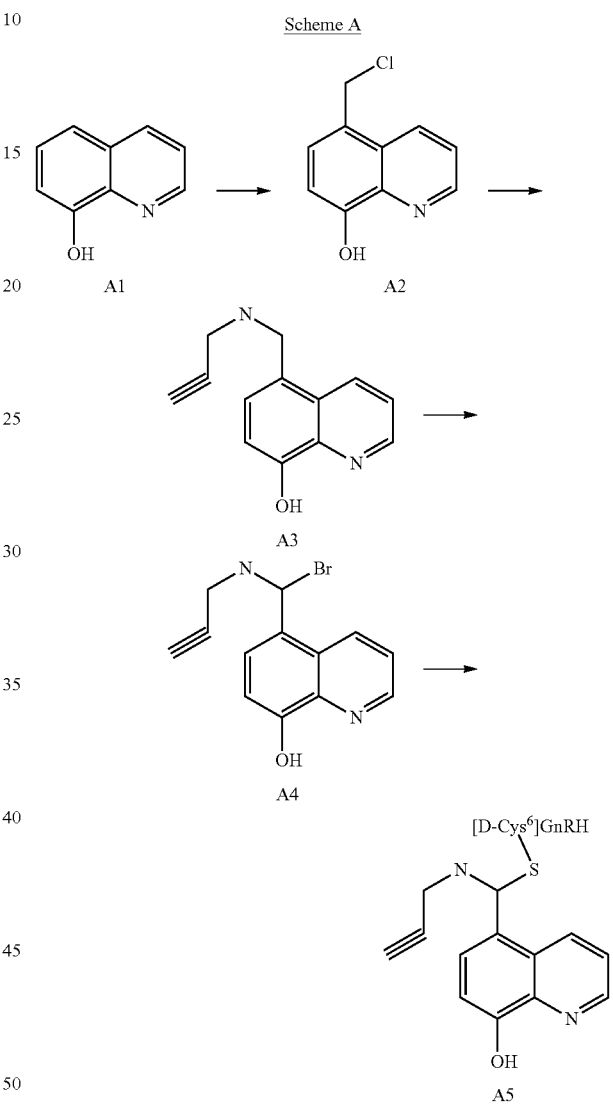

Scheme A

The compounds of formula II can be prepared by the method as shown in Scheme B, or by the methods given in the examples or by analogous methods.

As shown in Scheme B below, substitution of the chloro group in 5-chloromethyl-8-hydroxyquinoline A2 (prepared as described in Scheme A) with cysteine provides the intermediate B1. Alkylation of the intermediate B1 with propargyl bromide produces the target compound B2, which is the compound M11a or M12a in Appendix III.

Scheme B

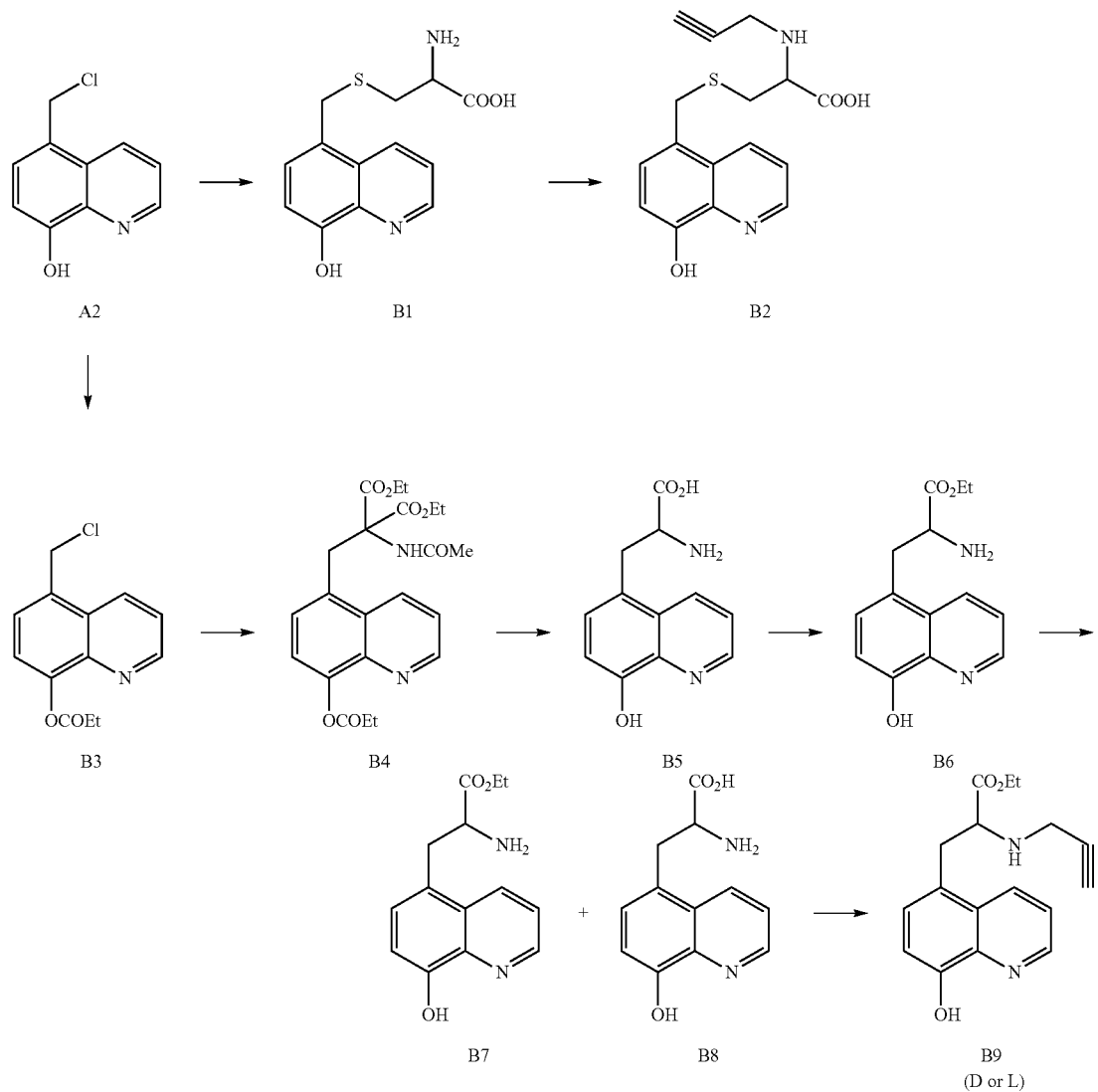

In another synthetic route according to Scheme B, the OH group of 5-chloromethyl-8-hydroxyquinoline A2 is first protected as its acetyl derivative B3. Condensation of compound B3 with diethyl acetamidomalonate proceeds smoothly in ethanol, with sodium ethoxide as the base, and gives the expected condensation derivative B4. Decarboxylation of compound B4 affords the amino acid derivative B5. Esterification of B5 in the presence of thionyl chloride and ethanol produces the ethyl ester derivative B6. Compound B6 is hydrolyzed using α-chymotripsin as a catalyst to give a mixture of the L-amino acid derivative B8 (α-chymotripsin is L-specific and hydrolyzes only the L-form) and the D-amino acid ester derivative B7, which can be separated by HPLC. Treatment of the L-amino acid B8 or D-amino acid (obtained from the ester B7) with propargyl bromide provides the desired compound B9, which is the compound M9a or M31 in Appendix III.

For production of the compounds of formula III, the method shown in Scheme C or analogous methods or the methods given in the examples may be used.

Scheme C

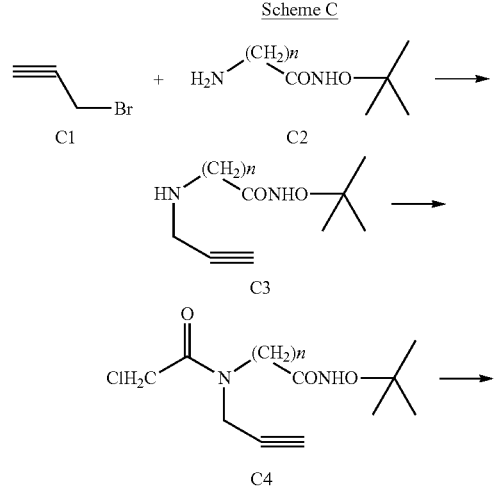

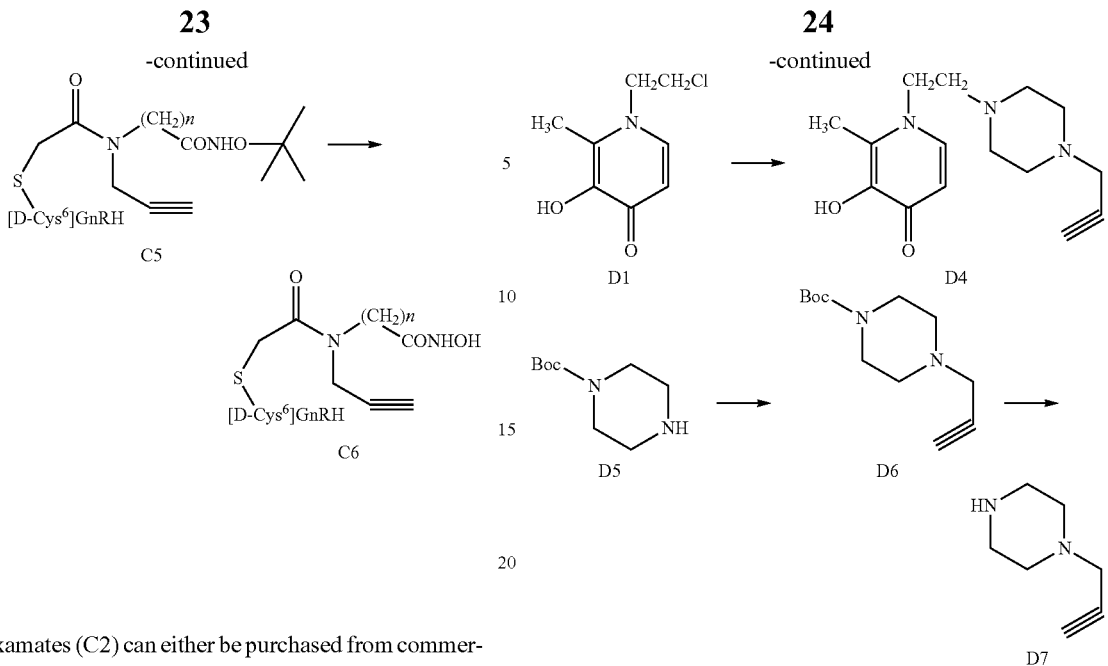

Hydroxamates (C2) can either be purchased from commercial sources or prepared by procedures well known to one of ordinary skill in organic chemistry. Alkylation of a hydroxamate (C2) with propargyl bromide (C1) in the presence of the appropriate base such as diisopropylethylamine provides a compound C3. Reaction of compound C3 with chloroacetyl chloride at about 0° C. in the presence of nitrogen, gives the N-chloroacetyl derivative (C4). Treatment of C4, for example, with the modified peptide [D-Cys6]GnRH, followed by deprotection of the hydroxamate, affords the target compound C6, which is the compound M22B in Appendix V.

The compounds of formula IV can be manufactured by the method as shown in Scheme D, or by the methods given in the examples or by analogous methods.

Scheme D

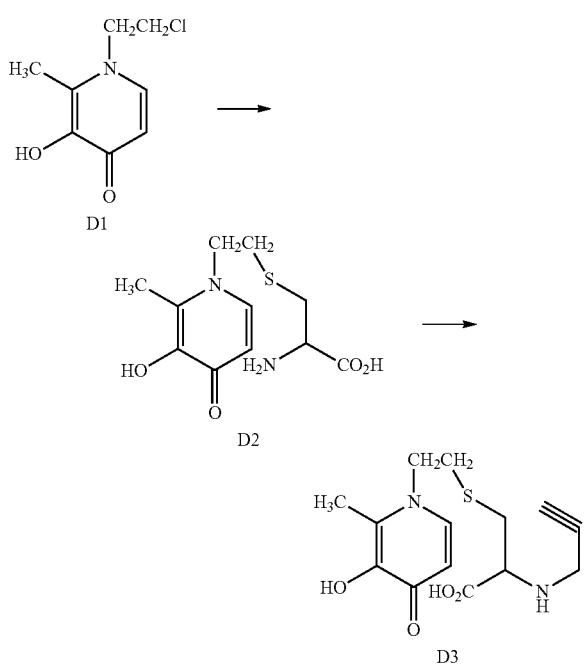

The starting material 1-chloroethyl-2-methyl-3-hydroxy-pyridinone (D1) can be prepared by known procedures. Treatment of D1 with cysteine results in the formation of the sulfide D2, that is then alkylated with propargylamine to give the desired compound D4, which is the compound designated M11b in Appendix VI.

In another synthetic route according to Scheme D, the compound D1 is directly reacted with propargylpiperazine D7 to give the desired chelator compound D4, which is the compound designated HLA20a in Appendix VI.

Propargylpiperazine (D7) is prepared by reaction of N-Boc-piperazine (D5) with propargylamine giving the compound D6, followed by removal of the protecting Boc group using trifluoroacetic acid.

Also contemplated by the present invention are pharmaceutically acceptable salts of the compounds of formula I, both salts formed by any carboxy groups present in the molecule and a base as well as acid addition and/or base salts.

Pharmaceutically acceptable salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge S. M., et al., "Pharmaceutical Salts," (1977) J. of Pharmaceutical Science, 66:1-19). The salts can also be pharmaceutically acceptable quaternary salts such as a quaternary salt of the formula —NRR'R"+Z' wherein R, R' and R" each is independently hydrogen, alkyl or benzyl and Z is a counterion, including chloride, bromide, iodide, O-alkyl, toluenesulfonate, methylsulfonate, sulfonate, phosphate, or carboxylate.

Pharmaceutically acceptable acid addition salts of the compounds include salts derived from inorganic acids such as hydrochloric, nitric, phosphoric, sulfuric, hydrobromic, hydriodic, phosphorous, and the like, as well as salts derived from organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate or galacturonate (see, for example, Berge S. M., et al., "Pharmaceutical Salts," (1977) J. of Pharmaceutical Science, 66:1-19).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

The compounds of the invention are specific iron chelators that are suitable to bind unbound iron within the cells. Iron that is not bound to transferrin is the toxic form of iron. The iron chelators of the invention have good transport properties and cross cell membranes thus chelating the unbound iron in excess within the cells. It is expected that their complexes with iron will leave the cells freely and will be rapidly excreted. It is further expected that the compounds, or at least a major part of the compounds, will be able to cross the BBB and thus will be suitable candidates for treatment of neurodegenerative diseases, disorders and conditions.

In another aspect, the present invention relates to pharmaceutical compositions comprising a compound of the invention or a pharmaceutically acceptable salt thereof, in combination with a pharmaceutically acceptable carrier.

In a further aspect, the present invention provides the use of a compound of the invention or of a pharmaceutically acceptable salt thereof as neuroprotective iron chelator for the preparation of a pharmaceutical composition for iron chelation therapy.

The pharmaceutical composition are intended for use in iron chelation therapy for treatment of diseases, disorders and conditions associated with iron overload and oxidative stress.

The pharmaceutical composition of the invention is for treatment and/or prevention of diseases, disorders and conditions associated with iron overload and oxidative stress such as, but not limited to, neurodegenerative and cerebrovascular diseases and disorders, neoplastic diseases, hemochromatosis, thalassemia, cardiovascular diseases, diabetes, inflammatory disorders, anthracycline cardiotoxicity, viral, protozoal and yeast infections, and for retarding ageing, and prevention and/or treatment of skin ageing and skin protection against sunlight and/or UV light.

In one preferred embodiment, the pharmaceutical compositions are for use for iron chelation and neuroprotection in the prevention and/or treatment of neurodegenerative and cerebrovascular diseases, conditions and disorders such as Parkinson's disease, Alzheimer's disease, stroke, amyotrophic lateral sclerosis (ALS), multiple sclerosis, Friedreich's ataxia, Hallervorden-Spatz disease, epilepsy and neurotrauma. In one preferred embodiment, the pharmaceutical composition is for treatment of Parkinson's disease. In another preferred embodiment, the pharmaceutical composition is for treatment of Alzheimer's disease. In a further preferred embodiment, the pharmaceutical composition is for treatment of a cerebrovascular disorder, particularly stroke.

The "prevention' aspect of the use of the iron chelators of the invention in diseases such as Parkinson's disease and Alzheimer's disease involves the prevention of further neurodegeneration and the further progress of the disease.

In still another preferred embodiment, the pharmaceutical compositions are for inhibition of cell proliferation in the treatment of neoplastic diseases, all types of cancer being encompassed by the invention. The iron chelator of the invention can be used alone or in combination with one or more cytotoxic anticancer drugs.

In another preferred embodiment, the pharmaceutical compositions are for prevention and/or treatment of iron overload in hemochromatosis and thalassemia.

In yet another preferred embodiment, the pharmaceutical compositions are for prevention and/or treatment of cardiovascular diseases, e.g. to prevent the damage associated with free radical generation in reperfusion injury.

In yet another preferred embodiment, the pharmaceutical compositions are for prevention and/or treatment of diabetes.

In yet another preferred embodiment, the pharmaceutical compositions are for prevention and/or treatment of inflammatory disorders. In one preferred embodiment, the inflammatory disorder is a joint inflammatory disorder, particularly rheumatoid arthritis. In another preferred embodiment, the inflammatory disorder is inflammatory bowel disease (IBD). In a further preferred embodiment, the inflammatory disorder is psoriasis.

In yet another preferred embodiment, the pharmaceutical compositions are for prevention and/or treatment of anthracycline cardiotoxicity, in case of cancer patients being treated with anthracycline neoplastic drugs.

In yet another preferred embodiment, the pharmaceutical compositions are for prevention and/or treatment of viral, protozoal and yeast infections. In one preferred embodiment, the viral infection is a retroviral infection, e.g. HIV-1, and the compound is used in the treatment of AIDS, optionally in combination with antiviral agents. In another preferred embodiment, the protozoal infection is malaria caused by *Plasmodium falciparum*. In a further preferred embodiment, the yeast infection is a *Candida albicans* infection.

In yet another preferred embodiment, the pharmaceutical compositions are for retarding ageing and/or improving the ageing process by prevention of ageing-related diseases, disorders or conditions such as neurodegenerative diseases, disorders or conditions.

In yet another preferred embodiment, the pharmaceutical compositions are for prevention and/or treatment of skin ageing and/or skin damage associated with ageing and/or exposure to sunlight and/or UV light.

In yet another preferred embodiment, the present invention provides a cosmetic composition for topical application for prevention and/or treatment of skin ageing and/or skin damage associated with ageing and/or exposure to sunlight and/or UV light. The cosmetic composition may be in the form of a lotion or cream and may be administered with other agents for skin treatment.

In another embodiment, the iron chelators are for use ex-vivo for preservation of organs intended for transplantation such as heart, lung or kidney In still another aspect, the present invention provides a method for iron chelation therapy which comprises administering to an individual in need thereof an effective amount of a compound of the invention or of a pharmaceutically acceptable salt thereof.

In one embodiment, the present invention provides a method for the prevention and/or treatment of a neurodegenerative disease, condition or disorder, which comprises administering to an individual in need thereof an effective amount of a compound of the invention or of a pharmaceutically acceptable salt thereof.

In yet another embodiment, the present invention provides a method for the prevention and/or treatment of cancer, which comprises administering to an individual in need thereof an effective amount of a compound of the invention or of a pharmaceutically acceptable salt thereof. In one preferred embodiment, the iron chelator of the invention is administered before, concurrently or after administration of one or more chemotherapeutic agents.

In another embodiment, the present invention provides a method for the prevention and/or treatment of iron overload in hemochromatosis or thalassemia patients, which comprises administering to said patient an effective amount of a compound of the invention or of a pharmaceutically acceptable salt thereof.

In yet another preferred embodiment, the present invention provides a method for prevention and/or treatment of cardiovascular diseases, e.g. to prevent the damage associated with free radical generation in reperfusion injury, which comprises administering to an individual in need thereof an effective amount of a compound of the invention or of a pharmaceutically acceptable salt thereof.

In yet another preferred embodiment, the present invention provides a method for prevention and/or treatment of diabetes, which comprises administering to an individual in need thereof an effective amount of a compound of the invention or of a pharmaceutically acceptable salt thereof.

In yet another preferred embodiment, the present invention provides a method for prevention and/or treatment of inflammatory disorders, which comprises administering to an individual in need thereof an effective amount of a compound of the invention or of a pharmaceutically acceptable salt thereof. In one preferred embodiment, the inflammatory disorder is a joint inflammatory disorder, particularly rheumatoid arthritis. In another preferred embodiment, the inflammatory disorder is inflammatory bowel disease (IBD). In a further preferred embodiment, the inflammatory disorder is psoriasis.

In yet another preferred embodiment, the present invention provides a method for prevention and/or treatment of anthracycline cardiotoxicity, which comprises administering to an individual undergoing treatment with anthracycline neoplastic drugs an effective amount of a compound of the invention or of a pharmaceutically acceptable salt thereof.

In yet another preferred embodiment, the present invention provides a method for prevention and/or treatment of a viral, protozoal or yeast infection which comprises administering to an individual in need thereof an effective amount of a compound of the invention or of a pharmaceutically acceptable salt thereof. In one preferred embodiment, the viral infection is a retroviral infection, e.g. HIV-1, and the compound is used in the treatment of AIDS, optionally in combination with antiviral agents. In another preferred embodiment, the protozoal infection is malaria caused by *Plasmodium falciparum*. In a further preferred embodiment, the yeast infection is a *Candida albicans* infection.

In yet another preferred embodiment, the present invention provides a method for retarding ageing and/or improving the ageing process by prevention of ageing-related diseases, disorders or conditions which comprises administering to an individual in need thereof an effective amount of a compound of the invention or of a pharmaceutically acceptable salt thereof. The individual in need may be a healthy individual or an individual suffering from an age-related disease such as a neurodegenerative disease, disorder or condition.

In yet another preferred embodiment, the present invention provides a method for prevention and/or treatment of skin ageing and/or skin damage associated with ageing and/or exposure to sunlight and/or UV light, which comprises administering to an individual in need thereof an effective amount of a compound of the invention or of a pharmaceutically acceptable salt thereof. The compound is most preferably administered topically in a pharmaceutical or cosmetic formulation.

The present invention also provides the use of the compound 5-[4-(2-hydroxyethyl)piperazin-1-ylmethyl]-8-hydroxyquinoline (herein identified as VK-28, Appendix IV) for the preparation of a pharmaceutical composition for treatment and/or prevention of a disease, disorder or condition associated with iron overload and oxidative stress selected from a neoplastic disease, hemochromatosis, thalassemia, a cardiovascular disease, diabetes, a inflammatory disorder, anthracycline cardiotoxicity, a viral infection, a protozoal infection, a yeast infection, retarding ageing, and prevention and/or treatment of skin ageing and skin protection against sunlight and/or UV light.

The present invention further provides a method for iron chelation therapy which comprises administering to an individual in need thereof an effective amount the compound 5-[4-(2-hydroxyethyl)piperazin-1-ylmethyl]-8-hydroxyquinoline (herein identified as VK-28, Appendix IV) for treatment and/or prevention of a disease, disorder or condition associated with iron overload and oxidative stress, excluding the prevention and/or treatment of a neurodegenerative disease, condition or disorder.

The present invention still further provides the use of the compound 5-[4-(2-hydroxyethyl)piperazin-1-ylmethyl]-8-hydroxyquinoline (herein identified as VK-28, Appendix IV) for the preparation of a cosmetic composition for topical application for prevention and/or treatment of skin ageing and/or skin damage associated with ageing and/or exposure to sunlight and/or UV light.

The present invention yet further provides the use of the compound 5-[4-(2-hydroxyethyl)piperazin-1-ylmethyl]-8-hydroxyquinoline (herein identified as VK-28, Appendix IV) ex-vivo for preservation of organs intended for transplantation such as heart, lung or kidney.

For preparing the pharmaceutical compositions of the present invention, methods well-known in the art can be used. Inert pharmaceutically acceptable carriers can be used that are either solid of liquid. Solid form preparations include powders, tablets, dispersible granules, capsules, cachets and suppositories.

A solid carrier can be one or more substances which may also act as diluents, flavoring agents, solubilizers, lubricants, suspending agents, binders, or tablet disintegrating agents; it can also be an encapsulating material.

Liquid pharmaceutical compositions include solutions, suspensions, and emulsions. As an example, water or water-propylene glycol solutions for parenteral injection may be mentioned. Liquid preparations can also be formulated in solution in aqueous polyethylene glycol solution. Aqueous solutions for oral use can be prepared by dissolving the active component in water and adding suitable colorants, flavoring agents, stabilizers, and thickening agents as desired. Aqueous suspensions for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical composition is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vial or ampoules. The unit dosage form can also be a capsule, cachet, or table itself or it can be the appropriate number of any of these packaged forms.

In therapeutic use for the treatment of Parkinson's disease, the compounds utilized in the pharmaceutical method of this invention may be administered to the patient at dosage levels of from 1 mg/Kg to 20 mg/Kg per day.

In therapeutic use for the treatment of stroke one or more dosages of from about 100 mg/Kg to about 500 mg/Kg of body weight may be administered to the patient as soon as possible after the event.

The dosage, however, may be varied depending upon the requirements of the patient, the severity of the condition being treated, and the compound being employed. Determination of optimum dosages for a particular situation is within the skill of the art.

The following examples illustrate particular methods for preparing compounds in accordance with this invention. These examples are intended as an illustration, and not as a limitation, of the scope of the invention.

EXAMPLES

The following examples describe the synthesis of the compounds of the invention (Chemical Section) and their biological activity (Biological Section).

I. Chemical Section
(i) Appendices I-VII

The structural formulas of the compounds of the invention are depicted in Appendices I to VI herein. Appendix VII contains the formulas of some intermediate compounds. For better identification of the compounds in the following examples, when possible, the compound designations used herein and the respective Appendix are given within brackets near the compound's name. When suitable, the designation given in the Schemes A-D above are used for starting compounds or intermediates.

The contents of the Appendices are as follows:
Appendix I—Compounds M6A, M7A, MBA, M18A, M19A, M20A, M21A, M22A, M27A, M28A.
Appendix II—Compounds M6, M7, M8, M11, M12, M18, M19, M20, M21, M22 M27, M28.
Appendix III—Compounds HLA16a, HLA20, M9a, M10a, M11a, M12a, M13a, m15a, M17, M30, M31, M33, M34.
Appendix IV—Compounds VK-28 (known), HLA16, HLM7, HLM8, HLM9, M9, M10, M11B, M12B, M13, M15, M32.
Appendix V—Compounds M6B, M7B, M8B, M18B, M19B, M20B, M21B, M22B, M27B, M28B, M35, M36, M36a, M37-46.
Appendix VI—Compounds M9b, M11b, M12b, M13b, M15b, HLA16b, M17a, HLA20a, M30a, M31a, M33a, M34b.
Appendix VII—Intermediates H1, H2, H3, H4, H5, H6.
(ii) General Starting materials for chemical synthesis were obtained from the following companies: Aldrich (USA), E. Merck (Germany), Fluka, (Switzerland).

Proton NMR spectra were measured on a Bruker WH-270, a Bruker DPX-250, or a Bruker AMX-400 NMR spectrometer. Flash column chromatography separations were performed on silica gel Merck 60 (230-400 mesh ASTM). UV/VIS spectra were measured on a Hewlett-Packard 8450A diode array spectrophotometer. TLC was performed on E. Merck Kieselgel 60 $F_{254}$ plates. Staining of TLC plates was done by: (i) basic aqueous 1% $KMnO_4$; (ii) 0.3% ninhydrin in $EtOH_{abs}$. Tetrahydrofuran was distilled over $LiAlH_4$ and passed through an $Al_2O_3$ column. Mass spectra (DI, EI-MS) were measured on a VG-platform-II electrospry single quadropole mass spectrometry (Micro Mass, UK).

Examples

Example 1

Synthesis of D-N-propargyl-3-(8-hydroxyquinolin-5-yl)alanine (M9a, Appendix III) and L-N-propargyl-3-(8-hydroxyquinolin-5-yl)alanine (M10a, Appendix III)

These enantiomers of Formula II herein were prepared by the method depicted in Scheme B above, by the following steps:
(i) Synthesis of 5-chloromethyl-8-hydroxyquinolinoline (A2)

A mixture of 14.6 g (0.1 mole) of 8-hydroxyquinolinoline, 16 ml of 32% hydrochloric acid, and 16 ml (0.1 ml) of 37% formaldehyde at 0° C. was treated with hydrogen chloride gas for 6 h. The solution was allowed to stand at room temperature for 2 h without stirring. The yellow solid was collected on a filter and dried to give crude 5-chloromethyl-8-hydroxyquinoline hydrochloride (A2): 2 16 g; $H^1$ NMR (250 MHz, $CDCl_3$): 5.32 (s, 2H), 7.53 (m, 1H), 7.85 (m, H), 8.12 (m, 1H), 9.12 (m, 1H), 9.28 (m, 1H).
(ii) Synthesis of 8-(5-chloromethyl)quinolyl acetate (B3)

To a stirred solution of crude A2 obtained in step (i) above (230 mg, 1 mmole) in dry DMF (5 ml) at 0° C., pyridine (0.3 ml, 2.5 mmol) and acetyl chloride (0.6 ml, 8 mmole) were slowly added simultaneously under $N_2$. The reaction mixture was stirred at 0° C. for 1 h and at room temperature for 1 h. After cooling to 0° C., 10 ml of water were added, and the resulting mixture was stirred at 0° C., for 20 min. The mixture was then extracted with chloroform (3×20 ml). The combined organic layer was washed with saturated $NaHCO_3$ (2×20 ml), brine (2×20 ml) and dried over $Na_2SO_4$. Evaporation afforded the compound (B3) (crude) (180 mg, 75%) as a light brown solid. m.p.=119-120° C., $R_f$ 0.75 ($CHCl_3$:MeOH:$NH_3$ 9:1: 0.25). $^1H$ NMR (250 MHz, $CDCl_3$): 2.25 (s, 3H), 4.98 (s, 2H), 7.40 (d, J=7.7 Hz, 1H), 7.55 (m, 2H), 8.47 (dd, J=8.6, 1.6 Hz, 1H), 8.96 (dd, J=4.2, 1.5 Hz, 1H).
(iii) Synthesis of diethyl 8-hydroxyquinolin-5-yl-methyl-acetamidomalonate (HLM7, Appendix IV)

To a solution of acetamidomalonate (183 mg, 0.842 mmol) and metallic sodium (34 mg, 0.842 mmole) in ethanol (50 ml), 8-(5-chloromethyl)quinolyl acetate (B3) (180 mg, 765 mmole) in $CHCl_3$ (5 m) was added. The mixture was stirred for 5 h under reflux, cooled, and evaporated in vacuum. Water (20 ml) was added to the residue and the mixture was extracted with CHCl₃: EtOAc (3×20 ml, 1: 1). The organic layer was washed with brine (2×20 ml) and dried over Na₂SO₄. Evaporation afforded the title compound (HLM7): (170 mg, 59%) as a light brown solid (crude) m.p.=153-154° C., R$_f$ 0.25 (CHCl₃:MeOH:NH₃ 9:1:0.25). ¹H NMR (250 MHz, CDCl₃): 1.30 (dd, J=7.1, 7.1 Hz, 6H), 1.86 (s, 3H), 4.03 (s, 2H), 4.27 (m, 4H), 6.46 (s, 1NH), 7.10 (dd, J=16.6, 7.9 Hz, 2H), 7.42 (dd, J=8.7, 4.2 Hz, 1H), 8.76 (dd, J=4.2, 1.1 Hz, 1H).

(iv) Synthesis of DL-3-(8-hydroxyquinolin-5-yl)alanine (HLM8, Appendix IV)

Diethyl (8-hydroxyquinolin-5-yl-methyl)-acetamidomalonate (HLM7) obtained in (iii) above (8.9 g, 21.9 mmol) was dissolved in 6 N HCl (150 ml), and the resultant mixture was refluxed for 10 h. The reaction mixture was evaporated to dryness; solvent was removed in vacuum. The residue was redissolved in H₂O and filtered. The pH of the solution was adjusted to between 5-5.5 with 10% NaOH. A yellow precipitate was collected by filtration, washed with water thoroughly, and re-crystallized from water (pH=5.5) and then washed with acetone to give the title compound (HLM8) (3.8 g, yield 65%), 100% purity, checked by HPLC [(C₁₈; solvent A=water, 0.1% v/v TFA; solvent B=MeCN:water=3:1, 0.1% v/v TFA; t$_R$=18.2 min (linear gradient 0-80% B over 55 min)]. m.p.=194° C., (decompose). ¹H NMR (250 MHz, D₂O) 3.42 (m, 1H), 3.58 (m, 1H), 3.93 (dd, J=7.2, 7.2 Hz, 1H), 7.22 (d, J=8.0 Hz, 1H), 7.50 (d, J=8.1 Hz, 1H), 7.94 (dd, J=8.7, 5.4 Hz, 1H), 8.84 (d, J=5.1 Hz, 1H), 9.06 (d, J=8.7 Hz, 1H); ¹³C NMR (100 MHz, DMSO) 32.14, 53.11, 111.03, 121.27, 127.46, 129.76, 133.35, 138.13, 147.46, 152.55, 170.30. Mass spectrometry: calculated for C₁₂H₁₂N₂O₃ m/z [M+H]⁺=233.24. found [M+H]⁺=233.25.

(v) Synthesis of DL-3-(8-hydroxyquinolin-5-yl)alanine ethyl ester (HLM9, Appendix IV)

To a stirred slurry of DL-3-(8-hydroxyquinolin-5-yl)alanine (HLM8) (2.19 g, 7.04 mmol) in absolute ethanol (26 ml) at 0° C., with protection from atmospheric moisture by CaCl₂ tube in N₂, thionyl chloride was added dropwise (1.1 ml, 14.1 mmol). The reaction mixture was stirred at 0° C. for 30 minutes and at room temperature for 30 minutes, and then refluxed overnight. The solution was evaporated to dryness in vacuum. The residue was dissolved in absolute ethanol and reevaporated to dryness. To ensure completeness of the esterification, the whole operation was repeated. The ester HLM9 (yellow solid, 1.67 g, 92% yield), which was shown by HPLC to contain about 1% of free amino acid, was further purified by FC(CH₂Cl₂:MeOH:AcOH 9:1.5:1.5). ¹H NMR (250 MHz, D₂O) 0.94 (dd, J=7.2, 7.2 Hz, 3H), 3.63 (m, 2H), 4.01 (m, 2H), 4.34 (dd, J=7.7, 7.5 Hz, 1H), 7.31 (d, J=8.0 Hz, 1H), 7.56 (d, J=8.2 Hz, 1H), 8.01 (dd, J=8.7, 5.4 Hz, 1H), 8.93 (d, J=5.4 Hz, 1H), 9.08 (d, J=8.7 Hz, 1H).

(vi) Synthesis of L-3-(8-hydroxyquinolin-5-yl)alanine (M10, Appendix 19 and D-3-(8-hydroxy-quinolin-5-yl)alanine ethyl ester (B7, Scheme B)

DL-3-(8-hydroxy-quinolin-5-yl)alanine ethyl ester (HLM9) (89.2 mg) obtained in 1(v) above was dissolved in 5 ml water, the pH of the solution was adjusted to about 6.4 with 0.2M NaOH, α-chymotrypsin (0.9 mg) was added, and the mixture was incubated at room temperature for 6 h, the pH being kept constant by addition of 0.2 M NaOH. After the digestion, the mixture was lyophilized to dryness and separated by semi-preparative HPLC [(C₁₈; solvent A=water, 0.1% v/v TFA; solvent B=MeCN:water=3:1, 0.1% v/v TFA; t$_R$=18.0 min (linear gradient 0-80% B over 55 min)]. Since α-chymotrypsin is specific for the L-form, L-3-(8-hydroxyquinolin-5-yl)alanine (M10) was obtained: 27.6 mg, 35%, 100% purity, [α]$_D^{20}$=+13.5. (D-3-(8-hydroxy-quinolin-5-yl)alanine ethyl ester (B7) was recovered: 39.2 mg, 88% recovery). ¹H NMR (250 MHz, D₂O) 3.49 (m, 1H), 3.65 (m, 1H), 3.95 (m, 1H), 7.34 (m, 1H), 7.57 (m, 1H), 8.0 (m, 1H), 8.91 (m, 1H), 9.14 (m, 1H). Mass spectrometry: calculated for C₁₂H₁₂N₂O₃ m/z [M+H]⁺=233.24. found [M+H]⁺=233.26.

(vii) Synthesis of D-3-(8-hydroxyquinolin-5-yl)alanine (M9, Appendix IV)

For hydrolysis of the ethyl ester, 33.4 mg D-3-(8-hydroxyquinolin-5-yl)alanine ethyl ester (B7) recovered in step 1(vi) was dissolved in 11 ml 0.2 M NaOH, and the solution was stirred at room temperature for 6 h The water was removed by lyophilization, and the product was purified by semi-preparative HPLC [(C₁₈; solvent A=water, 0.1% v/v TFA; solvent B=MeCN:water=3:1, 0.1% v/v TFA; t$_R$=18.4 min (linear gradient 0-80% B over 55 min)] to give the title compound M9: 26.8 mg, 89%, 99.1% purity. [α]$_D^{20}$=−10.3. ¹H NMR (250 MHz, D₂O) 3.40 (s, 1H), 3.55 (s, 1H), 3.91 (s, 1H), 7.15 (s, 1H), 7.45 (s, 1H), 7.91 (s, 1H), 8.80 (s, 1H), 9.02 (s, 1H). Mass spectrometry ç calculated for C₁₂H₁₂N₂O₃ m/z [M+H]⁺=233.24. found [M+H]⁺=233.26.

(viii) Synthesis of D-N-propargyl-3-(8-hydroxyquinolin-5-yl)alanine (M9a, Appendix III)

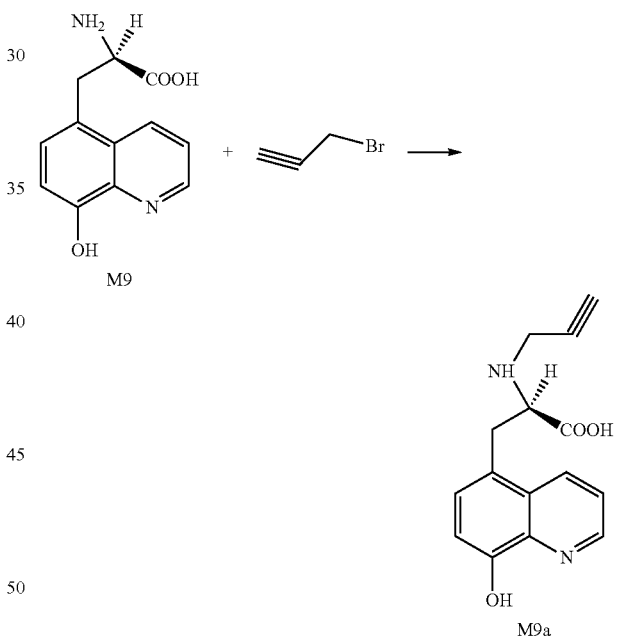

A mixture of NaHCO₃ (17 mg, 0.2 mmol) and compound M9 (23.2 mg, 0.1 mmol) from step (vii) above was dissolved in 5 ml DMSO, and the solution was stirred at room temperature for 2 h. To the solution, propargyl bromide (11.9 mg, 0.1 mmol) was slowly added, and the solution was stirred at room temperature for 24 h. The solvent was removed by vacuum, and the crude product was purified by semi-preparative HPLC [(C₁₈; solvent A=water, 0.1% v/v TFA; solvent B=MeCN:water=3:1, 0.1% v/v TFA; t$_R$=22.4 min (linear gradient 0-80% B over 55 min)] to give the title compound M9a: 19 mg, 70% yield. [α]$_D^{20}$=−12.3. H¹ NMR (250 MHz, CDCl₃), 2.21 (m, 1H), 3.28 (d, J=2.44 Hz, 2H), 3.82 (s, 2H), 7.08 (m, 1H), 7.33 (d, J=10.59, 1H), 7.46 (dd, J=8.55, 4.18 Hz, 1H), 8.67 (dd, J=8.56, 1.55 Hz, 1H), 8.78 (dd, J=4.18.

1.51 Hz, 1H). Mass spectrometry: calculated for $C_{15}H_{14}N_2O_3$ m/z $[M+H]^+$=271.28. found $[M+H]^+$=271.30.

(ix) Synthesis of L-N-propargyl-3-(8-hydroxyquinolin-5-yl) alanine (M10a, Appendix III)

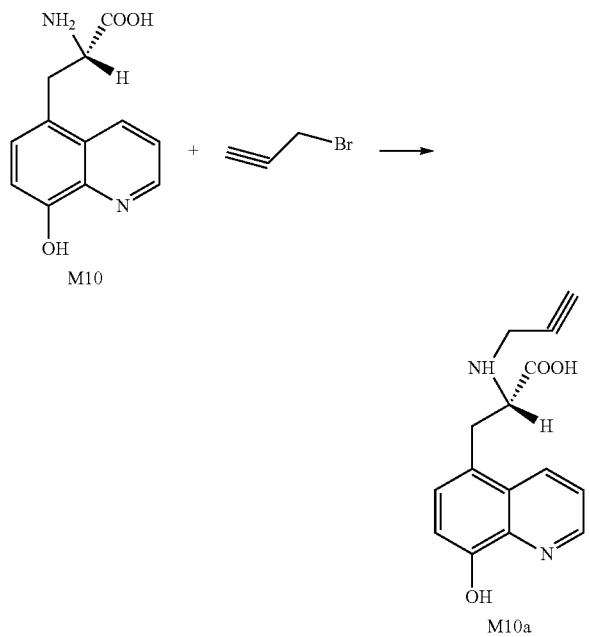

The title compound was synthesized using the procedure of step (viii) above. 78% yield. $[\alpha]_D^{20}$=+15.3. $H^1$ NMR (250 MHz, CDCl$_3$), 2.25 (m, 1H), 3.26 (d, J=2.44 Hz, 2H), 3.80 (s, 2H), 7.08 (m, 1H), 7.33 (d, J=10.59, 1H), 7.46 (dd, J=8.55, 4.18 Hz, 1H), 8.64 (dd, J=8.53, 1.55 Hz, 1H), 8.78 (dd, J=4.18. 1.51 Hz, 1H); Mass spectrometry: calculated for $C_{15}H_{14}N_2O_3$ m/z $[M+H]^+$=271.28. found $[M+H]^+$=271.30.

Example 2

Synthesis of 5-(4-propargylpiperazin-1-ylmethyl)-8-hydroxy-quinoline (HLA20, Appendix III)

The title compound was prepared by reaction of 5-chloromethyl-8-hydroxyquinolinoline (A2) with N-propargyl piperazine as follows:

(i) Synthesis of tert-butyl 1-piperazinecarboxylate (D5, Scheme D)

A solution of di(tert-butyl) dicarbonate (2.93 g, 12.77 mmole) in MeOH (25 ml) was slowly added to a stirring solution of piperazine (2.00 g, 23.22 mmole) in MeOH (50 ml) at 0° C. The mixture was then stirred for 2 days at room temperature, and the solvent was removed in vacuum. The crude solid was redissolved in Et$_2$O (100 ml) with warming, and a white precipitate was filtered off. The product was extracted from the mother liquor with 1 M citric acid solution (3×50 ml), and the aqueous layer was washed with Et$_2$OAc (3×50 ml), basified with Na$_2$CO$_3$ (pH 11), and extracted with Et$_2$OAc (3×50 ml). The organic layer was dried over Na$_2$SO$_4$ and evaporated in vacuum to give tert-butyl 1-piperazinecarboxylate (D5) as a waxy white solid (crude, 1.57 g, 66%), mp=53-45° C. $H^1$ NMR (250 MHz, CDCl$_3$) 1.42 (s, 9H), 1.89 (s, 1NH), 2.78 (m, 4H), 3.36 (m, 4H).

(ii) Synthesis of tert-butyl 4-propargylpiperazine-1-carboxylate (D6, Scheme D)

Propargyl bromide (356.9 mg, 3 mmol) was slowly added to a mixture of tert-butyl 1-piperazinecarboxylate obtained in step 2(i) above (558.8 mg, 3 mmole) and diisopropylethylamine (407.1 mg, 3.15 mmol) in CHCl$_3$ (25 ml) at 0° C. The mixture was stirred for 24 h at room temperature. 50 ml of CHCl$_3$ was then added and the solution was washed with 5% NaHCO$_3$ (3×50 ml), brine (2×50 ml), and then dried over Na$_2$SO$_4$. The solution was filtered and evaporated to dryness. The residue was crystallized from a mixture of benzene-hexane (1:1) to give tert-butyl 4-propargylpiperazine-1-carboxylate (D6) (crude 337 mg, 86%). $H^1$ NMR (250 MHz, CDCl$_3$): 1.42 (s, 9H), 2.22 (s, 1H), 2.46 (s, 4H), 3.26 (s, 2H), 3.41 (s, 4H).

(iii) Synthesis of N-propargylpiperazine (D7, Scheme D)

tert-Butyl 4-propargylpiperazine-1-carboxylate of step 2(ii) above (570 mg, 2.545 mmol) was dissolved in trifluoroacetic acid (10 ml) and water (2.5 ml). The mixture was then stirred at room temperature overnight. The solution was evaporated to dryness in vacuum. The residue was dissolved in water (10 ml) and then basified with Na$_2$CO$_3$ (pH 11), and extracted with Et$_2$OAc (3×50 ml). The organic layer was washed with brine (2×50 ml) and dried over Na$_2$SO$_4$ overnight. Evaporation in vacuum gave N-propargylpiperazine (D7) as white solid. (crude, 193 mg, 62% yield). $H^1$ NMR (250 MHz, CDCl$_3$) 1.64 (s, 1NH), 2.26 (m, 1H), 2.55 (dd, J=4.73, 4.50 Hz, 4H), 2.93 (dd, J=4.96, 4.84 Hz, 4H), 3.29 (d, J=2.44 Hz, 2H).

(iv) Synthesis of 5-(4-propargylpiperazin-1-ylmethyl)-8-hydroxyquinoline (HLA20, Appendix III))

To a mixture of 5-chloromethyl-8-hydroxyquinoline hydrochloride (A2) (323 mg, 1.407 mmol) and diisopropylethylamine (0.26 ml, 1.477 mmol, 1.05 eq) in 6 ml CHCl$_3$ at 0° C., N-propargylpiperazine obtained in step 2(iii) above was added (173 mg, 1.407 mmol, 1 eq). The mixture was stirred for 24 h at room temperature. 10 ml of CHCl$_3$ was then added and the solution was washed with 5% NaHCO$_3$ (3×50 ml), brine (2×50 ml), and then dried over Na$_2$SO$_4$. The crude product was purified by FC to give the title compound (HLA20) as a white solid. (337 mg, 86% yield). $H^1$ NMR (250 MHz, CDCl$_3$), 2.23 (m, 1H), 2.54 (s, 8H), 3.28 (d, J=2.44 Hz, 2H), 3.80 (s, 2H), 7.08 (m, 1H), 7.36 (d, J=10.59, 1H), 7.46 (dd, J=8.55, 4.18 Hz, 1H), 8.67 (dd, J=8.56, 1.55 Hz, 1H), 8.78 (dd, J=4.18. 1.51 Hz, 1H); $^{13}$C NMR (100 MHz, CDCl$_3$) 46.77, 51.98, 52.87, 60.55, 73.05, 78.92, 108.60, 121.40, 124.58, 127.87, 128.87, 134.10, 138.68, 147.50, 151.78.

Example 3

Synthesis of 5-(4-propargylaminoethoxycarbonyl-piperazin-1-ylmethyl)-8-hydroxyquinoline (HLA16a, Appendix III)

(i) Synthesis of ethyl 4-(8-hydroxyquinolin-5-ylmethyl)-1-piperazine carboxylate (HLA16, Appendix IV)

To a mixture of 5-chloromethyl-8-hydroxyquinoline hydrochloride (A2) (2.36 g, 10.2 mmol) and diisopropylethylamine (3.6 ml, 20.4 mmol, 2 eq) in 50 ml CHCl$_3$ at 0° C., ethyl 1-piperazinecarboxylate (1.5 ml, 10.2 mmol, 1 eq) was added. The mixture was stirred for 24 h at room temperature, and then 100 ml of CHCl$_3$ was added and the solution was washed with 5% NaHCO$_3$ (3×50 ml), brine (2×50 ml), and then dried over Na$_2$SO$_4$. The solution was filtered and evaporated to dryness. The residue was crystallized from a mixture of benzene-hexane (1:1) to yield the title compound HLA16 as white solid. (1.38 g, 42% yield, m.p.=92-93° C.). H$^1$ NMR (250 MHz, CDCl$_3$), 1.25 (dd, J=7.1, 7.1 Hz 3H), 2.42 (s, 4H), 3.43 (s, 4H), 3.81 (s, 2H), 4.14 (dd, j=14.21, 7.12 Hz, 2H), 7.08 (d, J=7.72 Hz, 1H), 7.31 (m, 1H), 7.47 (dd, J=8.52, 4.20 Hz, 1H), 8.66 (dd, J=8.56, 1.58 Hz, 1H), 8.79 (dd, J=4.18. 1.54 Hz, 1H).

(ii) In an alternative method, the title compound HLA16a is prepared by reaction of 5-chloromethyl-8-hydroxyquinoline with N-propargylaminoethoxycarbonyl-piperazine as follows:

(iia) Synthesis of N-propargylaminoethoxycarbonylpiperazine (H1, Appendix VII)

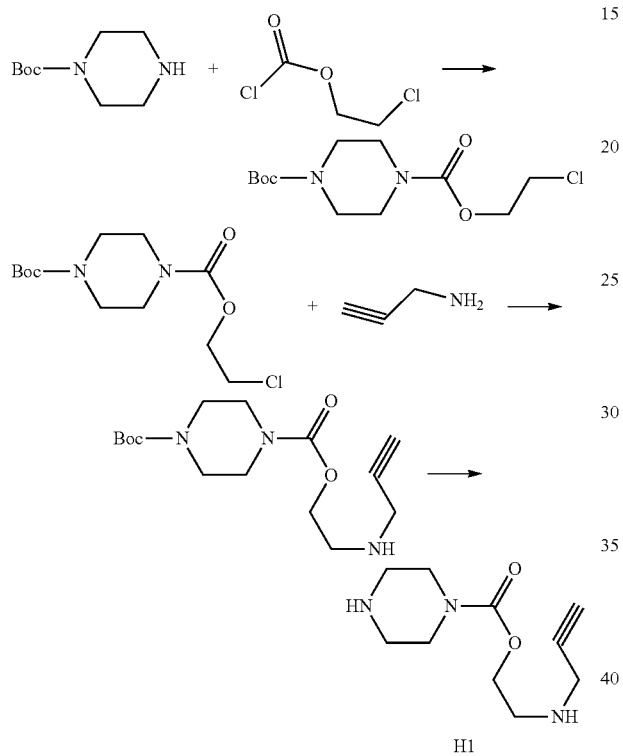

2-chloroethyl chloroformate (429 mg, 3 mmol) was added slowly to a mixture of tert-butyl 1-piperazinecarboxylate obtained as step (ii) in Example 2 (559 mg, 3 mmol) and diisopropylethylamine (407 mg, 3.15 mmol) in CHCl$_3$ (25 ml) at 0° C. The mixture was stirred for 2 h at room temperature. CHCl$_3$ (50 ml) was then added and the solution was washed with 5% NaHCO$_3$ (3×50 ml), brine (2×50 ml), and then dried over Na$_2$SO$_4$. The solution was filtered and evaporated to dryness. The residue was dissolved in CH$_2$Cl$_2$ (25 ml) at room temperature, and propargylamine (0.205 ml, 165 mg, 3 mmol) was added. After 24 h of stirring at room temperature, the solvent was removed by vacuum, and to the residue was added 20 ml of a solution of TFA:H$_2$O:TES:thioanisole (85:5:5:5). The mixture was then stirred at room temperature for 2 h. The solution was evaporated to dryness in vacuum. The resulted residue was dissolved in water (10 ml) and then basified with Na$_2$CO$_3$ (pH 11), and extracted with Et$_2$OAc (3×50 ml). The organic layer was washed with brine (2×50 ml) and dried over Na$_2$SO$_4$ overnight. Evaporation in vacuum gave the title compound H1: (251 mg, 40% total yield). H$^1$ NMR (250 MHz, CDCl3+D$_2$O) 2.26 (m, 1H), 3.11 (s 2H), 3.29 (dd, J=10.21, 7.45 Hz, 2H), 4.29 (d, J=11.23, 7.12 Hz, 2H), 2.55 (dd, J=4.73, 4.50 Hz, 4H), 2.93 (dd, J=4.96, 4.84 Hz, 4H). Mass spectrometry: calculated for C$_{10}$H$_n$N$_3$O$_2$ m/z [M+H]$^+$=212.26. found [M+H]$^+$=212.22.

(iib) Synthesis of 5-(4-propargylaminoethoxycarbonyl-piperazin-1-ylmethyl)-8-hydroxyquinoline (HLA16a, Appendix III)

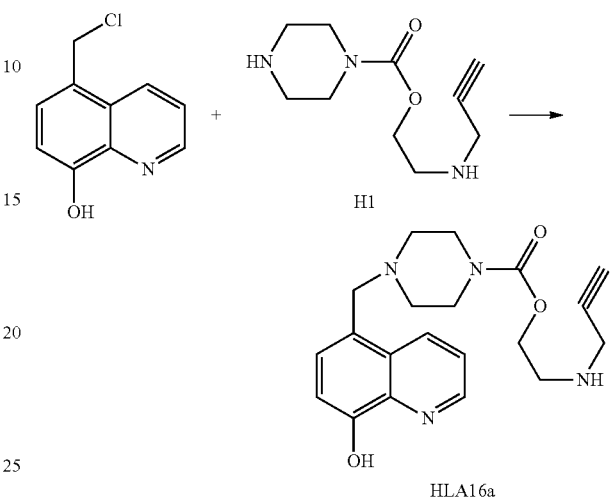

To a mixture of 5-chloromethyl-8-hydroxyquinoline hydrochloride (A2) (194 mg, 1 mmol) and diisopropylethylamine (0.348 ml, 2 mmol, 2 eq) in 5 ml CHCl$_3$ at room temperature, was added H1 (221 mg, 1 mmol, 1 eq). The mixture was stirred for 24 h at room temperature. 10 ml of CHCl$_3$ was then added and the solution was washed with 5% NaHCO$_3$ (3×10 ml), brine (2×10 ml), and then dried over Na$_2$SO$_4$. The solution was filtered and evaporated to dryness. The residue was crystallized from a mixture of toluene-hexane (1:1) to yield the title compound HLA16a as white solid. (184 mg, 50% yield). H$^1$ NMR (250 MHz, CDCl$_3$+D$_2$O) 2.23 (m, 1H), 3.30 (s 2H), 3.29 (dd, J=10.21, 7.45 Hz, 2H), 4.29 (d, J=11.23, 7.12 Hz, 2H), 2.55 (dd, J=4.73, 4.50 Hz, 4H), 2.93 (dd, J=4.96, 4.84 Hz, 4H), 3.78 (s, 2H), 7.08 (d, J=7.72 Hz, 1H), 7.31 (m, 1H), 7.47 (dd, J=8.52, 4.20 Hz, 1H), 8.66 (dd, J=8.56, 1.58 Hz, 1H), 8.79 (dd, J=4.18, 1.54 Hz, 1H). Mass spectrometry: calculated for C$_{20}$H$_{24}$N$_4$O$_3$ m/z [M+H]$^+$=369.43. found [M+H]$^+$=369.28.

Example 4

Synthesis of N-propargyl S-(8-hydroxyquinolin-5-ylmethyl)-L-cysteine (M12a, Appendix III) and N-propargyl S-(8-hydroxyquinolin-5-ylmethyl)-D-cysteine (M11a, Appendix III)

The title compounds were prepared according to the first route depicted in Scheme B hereinabove.

(i) Synthesis of S-(8-hydroxyquinolin-5-ylmethyl)-L-cysteine (M12, Appendix II)

L-cysteine hydrochloride hydrate (37 mg, 0.31 mmol) was dissolved in DMSO (3 ml). To the solution powdered KOH (36 mg, 0.34 mmol) was added, and the mixture was stirred for 30 min at room temperature. Then, powdered 5-chloromethyl-8-hydroxyquinoline hydrochloride (A2) (65 mg, 0.34 mmol) was added. The suspension was stirred at room temperature 12 h, 2 N HCl was added and the pH was adjusted to 5. The precipitate was washed with water and acetone. The crude product was further purified by semi-preparative HPLC to yield compound M12: 53 mg (61%). HPLC ($t_R$): 38.1 min (linear gradient: 50% B for the first 4 min, increased linearly to 100% B for 60 min) $[\alpha]_D^{20}$=20.5° (c=1.0, $H_2O$); $^1H$ NMR (250 MHz, $D_2O$) 2.89 (d, J=5.6 Hz, 2H), 3.95 (dd, J=5.1, 5.0 Hz, 1H), 4.18 (s, 2H), 7.25 (d, J=8.0 Hz, 1H), 7.57 (d, J=8.0 Hz, 1H), 7.96 (dd, J=8.7, 5.5 Hz, 1H), 8.88 (d, J=5.4 Hz, 1H), 9.22 (d, J=8.7 Hz, 1H); IR (KBr) $cm^{-1}$: 3438 (broad), 3081, 1685, 1637, 1560; Mass spectrometry: calculated for $C_{12}H_{12}N_2O_3$ m/z $[M+H]^+$=279.33. found $[M+H]^+$=279.13.

(ii) Synthesis of S-(8-hydroxyquinolin-5-ylmethyl)-D-cysteine (M11, Appendix II)

Compound M11 was prepared as method described in 4(i) above for M12, but using D-cysteine instead of L-cysteine as starting material. $^1H$ NMR (250 MHz, $D_2O$) 2.85 (d, J=5.5 Hz, 2H), 3.83 (t, J=5.4 Hz, 1H), 4.05 (s, 2H), 7.06 (d, J=8.0 Hz, 1H), 7.42 (d, J=8.0 Hz, 1H), 7.86 (dd, J=8.7, 5.4 Hz, 1H), 8.77 (d, J=5.3 Hz, 1H), 9.06 (d, J=8.7 Hz, 1H). IR (KBr) $cm^{-1}$: 3410 (broad), 3050, 2926, 1701, 1685, 1550. Mass spectrometry: calculated for $C_{12}H_{12}N_2O_3$ m/z $[M+H]^+$=279.33. found $[M+H]^+$=279.26; $[\alpha]_D^{20}$=−15.3° (c=1.0, $H_2O$).

(iii) Synthesis of N-propargyl S-(8-hydroxyquinolin-5-ylmethyl)-L-cysteine (M12a, Appendix III)

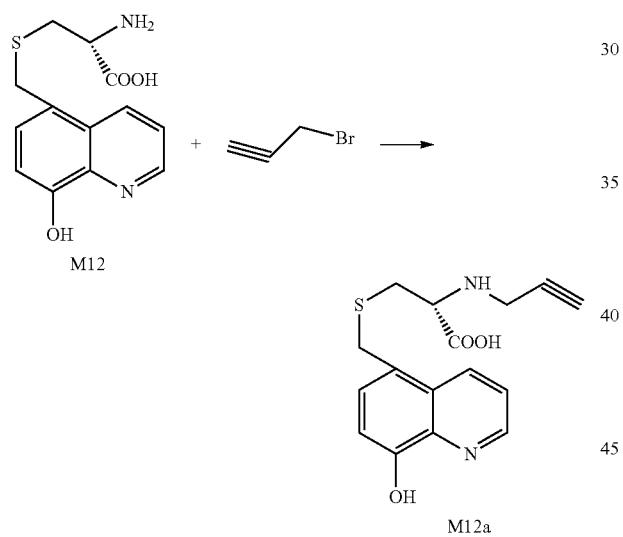

To a stirred mixture of $NaHCO_3$ (34 mg, 0.4 mmol) and compound M12 (54 mg, 0.2 mmol) in 5 ml DMSO, propargyl bromide (24 mg, 0.2 mmol) was slowly added, and the solution was stirred at room temperature for 24 h. The solvent was removed by vacuum, and the crude product was crystallized (pH 5.5) and then further purified by semi-preparative HPLC [($C_H$; solvent A=water, 0.1% v/v TFA; solvent B=$CH_3CN$: water=3:1, 0.1% v/v TFA; $t_R$=24.4 min (linear gradient 0-80% B over 55 min)] to give the title compound M12a: 37 mg, 60% yield. $[\alpha]_D^{20}$=−16.3. (c=1.0, 0.1 N HCl). Mass spectrometry: calculated for $C_{16}H_{16}N_2O_3S$ m/z $[M+H]^+$= 317.38. found $[M+H]^+$=317.30. $^1H$ NMR (250 MHz, $CHCl_3$+$D_2O$) 2.34 (m, 1H), 2.89 (d, J=5.6 Hz, 2H), 3.37 (s, 2H), 3.91 (dd, J=5.1, 5.0 Hz, 1H), 4.13 (s, 2H), 7.25 (d, J=8.0 Hz, 1H), 7.57 (d, J=8.0 Hz, 1H), 7.96 (dd, J=8.7, 5.5 Hz, 1H), 8.88 (d, J=5.4 Hz, 1H), 9.22 (d, J=8.7 Hz, 1H); IR (KBr) $cm^{-1}$: 3428 (broad), 3091, 1695, 1637, 1568.

(iv) Synthesis of N-propargyl S-(8-hydroxyquinolin-5-ylmethyl)-D-cysteine (M11a, Appendix III)

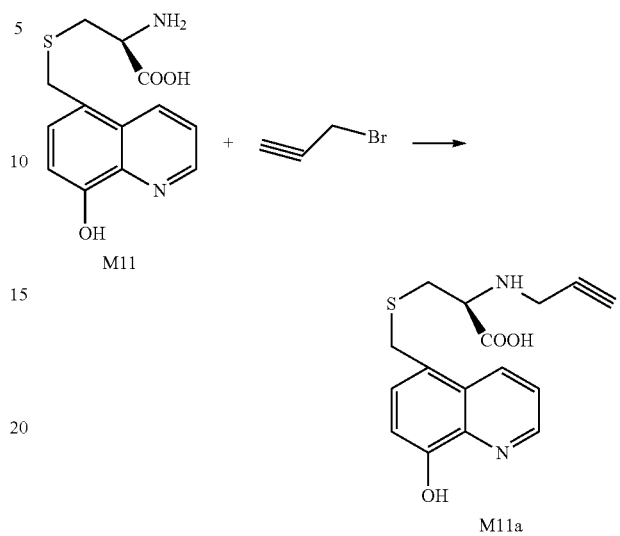

The title compound M11a was prepared according to the procedure for M12a, but using M11 instead of M12 as the starting material. Yield 70%. $[\alpha]_D^{20}$=−18.3. (c=1.0, 0.1 N HCl). Mass spectrometry: calculated for $C_{16}H_{16}N_2O_3S$ m/z $[M+H]^+$=317.38. found $[M+H]^+$=317.31. $^1H$ NMR. (250 MHz, $CHCl_3$+$D_2O$) 2.39 (m, 1H), 2.85 (d, J=5.6 Hz, 2H), 3.27 (s, 2H), 3.91 (dd, J=5.1, 5.0 Hz, 1H), 4.13 (s, 2H), 7.25 (d, J=8.0 Hz, 1H), 7.57 (d, J=8.0 Hz, 1H), 7.96 (dd, J=8.7, 5.5 Hz, 1H), 8.88 (d, J=5.4 Hz, 1H), 9.22 (d, J=8.7 Hz, 1H); IR (KBr) $cm^{-1}$: 3422 (broad), 3090, 1691, 1639, 1565.

Example 5

Synthesis of N-propargyl S-(8-hydroxyquinolin-5-ylmethyl)-L-cysteine (M12a, Appendix III) and N-propargyl S-(8-hydroxyquinolin-5-ylmethyl)-D-cysteine (M11a, Appendix III)—Method B The title compounds can be prepared by another method consisting in preparation of the N-9-fluorenylmethoxycarbonyl (N-Fmoc) derivatives of the compounds M11 and M12, removing the protecting Fmoc group and reacting with propargyl bromide.

(i) Synthesis of N-9-Fmoc-S-(8-hydroxyquinolin-5-ylmethyl)-L-cysteine (M11B, Appendix IV)

The crude compound M11 obtained in Example 4(i) (27.5 mg, 0.1 mmol) was dissolved in 10% $NaCO_3$ (12 ml). The solution was stirred and the pH was adjusted to approximately 8 using small portions of 10% $NaCO_3$. To the solution, (9-Fluorenylmethyl) succinimidyl carbonate (36.6 mg, 0.11 mmol, 1.1 equiv) in dioxane (2 ml) was added dropwise. The reaction mixture was stirred at room temperature for 12 h. The dioxane was evaporated under reduced pressure at room temperature, and the aqueous phase was extracted with $Et_2O$ (3×30 ml). The aqueous phase was acidified to pH 2-3 with 10% $KHSO4$ and extracted with EtOAc (3×30 ml). The combined EtOAc portions were dried over $NaSO_4$ and concentrated under reduced pressure. The residue was further purified by semi-preparative HPLC to yield the title compound: 26 mg (50%) HPLC ($t_R$: 38.1 min (linear gradient: 50% B for the first 4 min, increased linearly to 100% B 60 min) $^1H$ NMR (250 MHz, $CD_3OD$) 2.71 (dd, J=14.1, 9.1 Hz, 1H), 2.95 (dd, J=14.2, 4.5 Hz, 1H), 4.07 (t, J=7.1 Hz, 1H), 4.23 (m, 5H), 7.19 (m, 5H), 7.54 (m, 3H), 7.68 (m, 3H), 8.78 (d, J=4.9 Hz, 1H), 9.13 (d, J=8.6 Hz, 1H); IR (KBr) cm$^{-1}$: 3398, 3063, 2950, 1702, 1598, 1555; Mass spectrometry: calculated for $C_{28}H_{24}N_2O_5S$ m/z [M+H]$^+$=501.57. found [M+H]$^+$=501.51; $[\alpha]_D^{20}$=−18.3° (c=1.0, 9:1 MeOH/1.0 aqueous HCl).

(ii) Synthesis of N-9-Fmoc-(8-hydroxyquinolin-5-ylmethyl)-D-cysteine (M12B, Appendix IV)

Compound M12B was prepared by the method for synthesizing compound M11B as described in step 5(i) above, using the appropriate starting materials. $^1$H NMR (250 MHz, CD$_3$OD) 2.71 (dd, J=14.2, 9.1 Hz, 1H), 2.96 (dd, J=14.2, 4.4 Hz, 1H), 4.08 (t, J=7.0 Hz, 1H), 4.21 (m, 5H), 7.19 (m, 5H), 7.55 (m, 3H), 7.72 (m, 3H), 8.79 (d, J=4.9 Hz, 1H), 9.14 (d, J=8.2 Hz, 1H); IR (KBr) cm$^{-1}$: 3397, 3065, 2952, 1701, 1598, 1554; Mass spectrometry: calculated for $C_{28}H_{24}N_2O_5S$ m/z [M+H]$^+$=501.57. found [M+H]$^+$=501.51; $[\alpha]_D^{20}$=+17.1° (c=1.0, 9:1 MeOH/1.0 aqueous HCl)

(iii) Synthesis of N-propargyl S-(8-hydroxyquinolin-5-ylmethyl)-L-cysteine (M12a, Appendix III)

The title compound is obtained by removal of the Fmoc group from the compound M12B and reaction thereof with propargyl bromide.

(iv) Synthesis of N-propargyl S-(8-hydroxyquinolin-5-ylmethyl)-D-cysteine (M11a, Appendix III)

The title compound is obtained by removal of the Fmoc group from the compound M11B and reaction thereof with propargyl bromide.

Example 6

Synthesis of N-(4-propargylpiperazin-1-ylethyl)-2-methyl-3-hydroxy-4-pyridinone (HLA20a, Appendix VI)

The title compound was prepared as described in Scheme D by reaction of N-(2-chloroethyl)-2-methyl-3-hydroxy-4-pyridinone (H2, Appendix VII) (prepared as described in Bijaya L. Rai, Lotfollah Dekhordi, Hicham Khodr, Yi Jin, Zudong Liu, and Robert C. Hider *J. Med. Chem.* 1998, 41, 3347-3359) with N-propargylpiperazine (obtained as in step (iii) in Example 2):

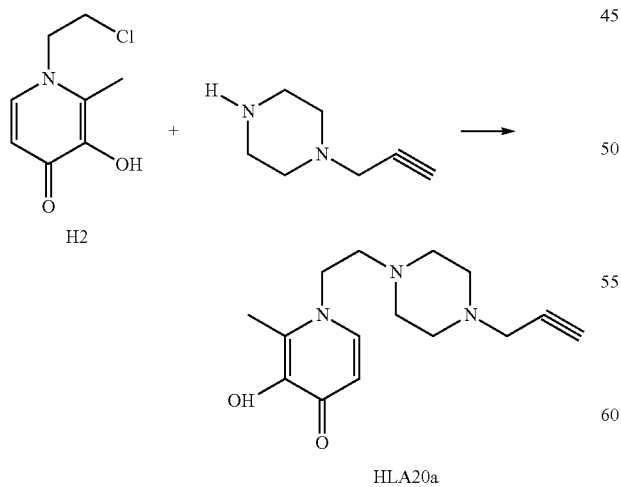

To a mixture of H2 (375 mg, 2 mmol) and diisopropylethylamine (0.352 ml, 2 mmol, 1 eq) in 6 ml CHCl$_3$ at 0° C., N-propargylpiperazine (245 mg, 2 mmol, 1 eq) was added. The mixture was then stirred for 24 h at room temperature. CHCl$_3$ (10 ml) was added and the solution was washed with 5% NaHCO$_3$ (3×50 ml), brine (2×50 ml), and then dried over Na$_2$SO$_4$. The crude product was purified by FC to give the title compound HLA20a: 337 mg, 60% yield. H$^1$ NMR (250 MHz, CDCl3+D2O), 2.23 (m, 1H), 3.28 (d, J=2.44 Hz, 2H), 2.54 (s, 8H), 3.42 (dd, 1.5 Hz 2H), 3.70 (dd, J=3.44, 1.5 Hz 2H), 7.18 (m, 1H), 7.78 (d, J=7.59, 1H), 2.60 (s 3H) Mass spectrometry: calculated for $C_{15}H_{21}N_3O_2$ m/z [M+H]$^+$=276.35. found [M+H]$^+$=276.30.

Example 7

Synthesis of N-(N-methyl-propargylaminoethyl))-2-methyl-3-hydroxy-4-pyridinone (M30a, Appendix VI)

The title compound was prepared as described in Scheme D by reaction of H2 and N-methyl-propargylamine as starting compound instead of N-propargylpiperazine:

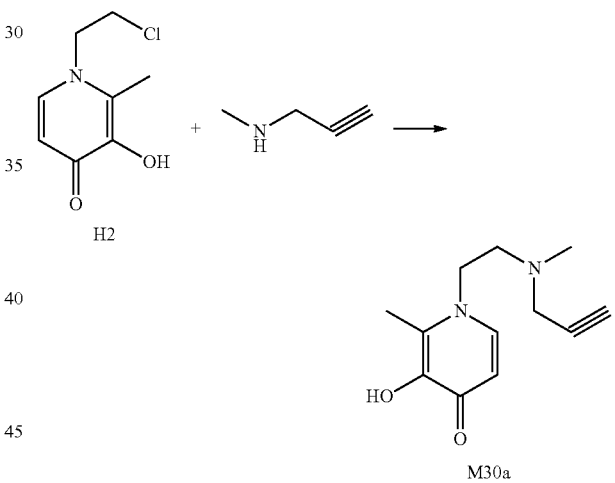

A solution of N-methyl-propargylamine hydrochloride (212 mg, 2 mmole) in CH$_2$Cl$_2$ (2 ml) was slowly added to a stirred solution of H2 (375 mg, 2 mmol) and diisopropylethylamine (0.352 ml, 2 mmol, 1 eq) in 6 ml CH$_2$Cl$_2$ at 0° C. The mixture was then stirred overnight at room temperature, and the solvent was removed in vacuum. The crude solid was redissolved in 10 ml of CHCl$_3$, then washed with 5% NaHCO$_3$ (3×30 ml), brine (2×20 ml). The organic layer was dried over Na$_2$SO$_4$ and evaporated in vacuum to give the title compound M30a. H$^1$ NMR (250 MHz, CDCl3+D2O), 2.23 (m, 1H), 3.28 (d, J=2.44 Hz, 2H), 2.33 (s 3H), 3.41 (dd, J=3.44, 1.5 Hz 2H), 3.78 (dd, J=3.44, 1.5 Hz 2H), 7.08 (m, 1H), 7.78 (d, J=7.59, 1H), 2.60 (s, 3H). Mass spectrometry: calculated for $C_{12}H_{16}N_2O_2$ m/z $[M+H]^+$=221.27. found $[M+H]^+$=221.30.

Example 8

Synthesis of N-(4-propargylaminoethoxycarbonyl-piperazin-1-ylmethyl))-2-methyl-3-hydroxy-4-pyridinone (HLA16b, Appendix VI)

The title compound HLA16b was synthesized according to the procedure for M30a in Example 7, but using N-propargylaminoethoxycarbonylpiperazine (H1) instead of N-methylpropargylamine as the starting material. Yield 64%. $H^1$ NMR (250 MHz, CDCl3+$D_2O$) 2.27 (m, 1H), 3.11 (s 2H), 3.29 (dd, J=10.21, 7.45 Hz, 2H), 4.29 (d, J=11.23, 7.12 Hz, 2H), 2.55 (dd, J=4.73, 4.50 Hz, 4H), 2.93 (dd, J=4.96, 4.84 Hz, 4H). 3.45 (dd, J=3.44, 1.5 Hz 2H), 3.81 (dd, J=3.44, 1.5 Hz 2H), 7.18 (m, 1H), 7.78 (d, J=7.59, 1H), 2.56 (s 3H). Mass spectrometry: calculated for $C_{17}H_{24}N_4O_4$ m/z $[M+H]^+$=349.40. found $[M+H]^+$=349.51.

Example 9

Synthesis of N-propargyl-S-(2-methyl-3-hydroxy-4-pyridinon-1-ylethyl)-L-cysteine. (M12b, Appendix VI) and N-propargyl-S-(2-methyl-3-hydroxy-4-pyridinon-1-ylethyl)-D-cysteine (M11b, Appendix VI)

The title compounds were prepared according to the first route depicted in Scheme D hereinabove by reaction of D1 with cysteine, and further reaction of the obtained D2 with propargyl bromide, as follows:

(i) Synthesis of S-(2-methyl-3-hydroxy-4-pyridinon-1-yl-ethyl)-L-cysteine (L-H3, Appendix VII)

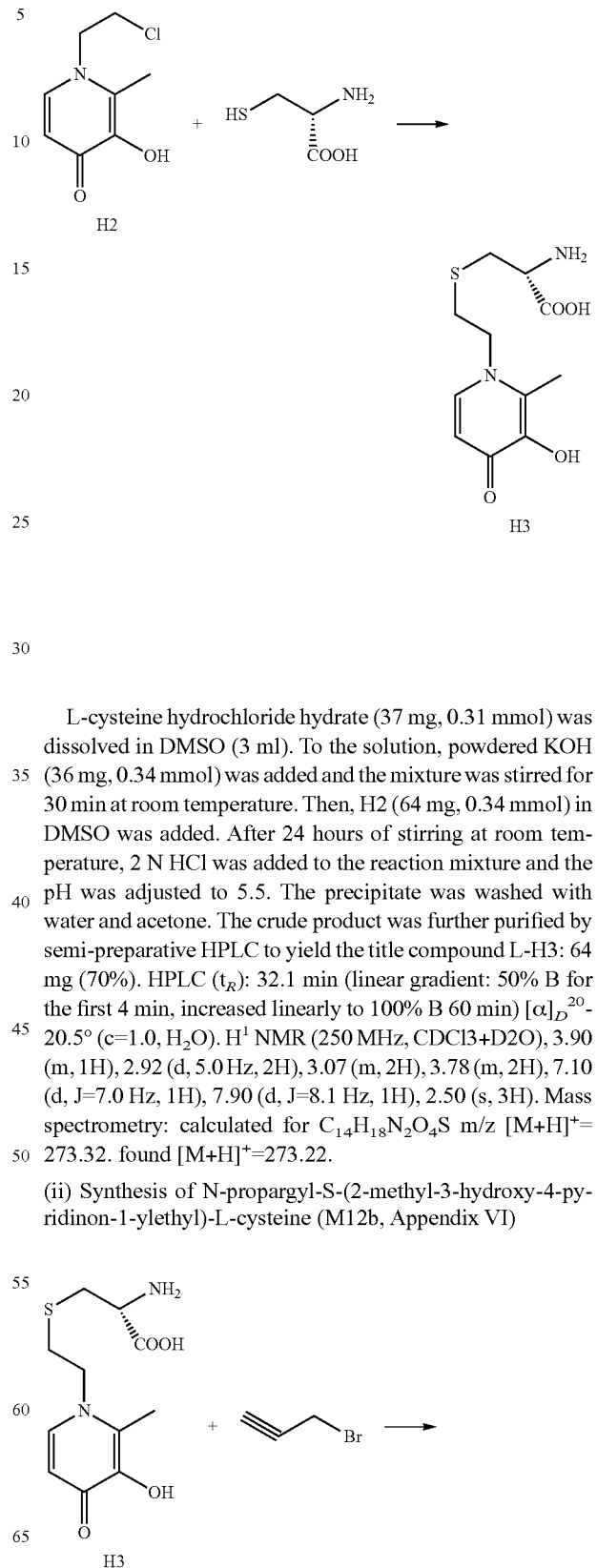

L-cysteine hydrochloride hydrate (37 mg, 0.31 mmol) was dissolved in DMSO (3 ml). To the solution, powdered KOH (36 mg, 0.34 mmol) was added and the mixture was stirred for 30 min at room temperature. Then, H2 (64 mg, 0.34 mmol) in DMSO was added. After 24 hours of stirring at room temperature, 2 N HCl was added to the reaction mixture and the pH was adjusted to 5.5. The precipitate was washed with water and acetone. The crude product was further purified by semi-preparative HPLC to yield the title compound L-H3: 64 mg (70%). HPLC ($t_R$): 32.1 min (linear gradient: 50% B for the first 4 min, increased linearly to 100% B 60 min) $[\alpha]_D^{20}$- 20.5° (c=1.0, $H_2O$). $H^1$ NMR (250 MHz, CDCl3+D2O), 3.90 (m, 1H), 2.92 (d, 5.0 Hz, 2H), 3.07 (m, 2H), 3.78 (m, 2H), 7.10 (d, J=7.0 Hz, 1H), 7.90 (d, J=8.1 Hz, 1H), 2.50 (s, 3H). Mass spectrometry: calculated for $C_{14}H_{18}N_2O_4S$ m/z $[M+H]^+$= 273.32. found $[M+H]^+$=273.22.

(ii) Synthesis of N-propargyl-S-(2-methyl-3-hydroxy-4-pyridinon-1-ylethyl)-L-cysteine (M12b, Appendix VI)

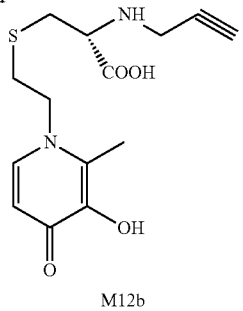

M12b

A mixture of NaHCO₃ (34 mg, 0.4 mmol) and L-H3 (75 mg, 0.34 mmol) was dissolved in 5 ml DMSO, and the solution was stirred at room temperature for 2 h. To the solution propargyl bromide (24 mg, 0.2 mmol) was slowly added, and the solution was stirred at room temperature for 24 h. The solvent was removed by vacuum, and the crude product was crystallized in water (pH 5.5) and further purified by semi-preparative HPLC [(C₁₈; solvent A=water, 0.1% v/v TFA; solvent B═CH₃CN:water=3:1, 0.1% v/v TEA; $t_R$=20.4 min (linear gradient 0-80% B over 55 min)] to give the title compound M12b: 37 mg, 60% yield. $[\alpha]_D^{20}$=−16.3. ¹H NMR (250 MHz, CHCl₃+D₂O) 2.39 (m, 1H), 3.35 (d, J=5.6 Hz, 2H), 4.01 (m, 1H), 2.92 (d, 5.0 Hz, 2H), 3.07 (m, 2H), 3.78 (m, 2H), 7.20 (d, J=7.0 Hz, 1H), 8.01 (d, J=8.1 Hz, 1H), 2.60 (s, 3H). Mass spectrometry: calculated for C₁₄H₁₈N₂O₄S m/z [M+H]⁺=311.37. found [M+H]⁺=311.40.

(iii) Synthesis of S-(2-methyl-3-hydroxy-4-pyridinon-1-ylethyl)-D-cysteine (D-H3, Appendix VII)

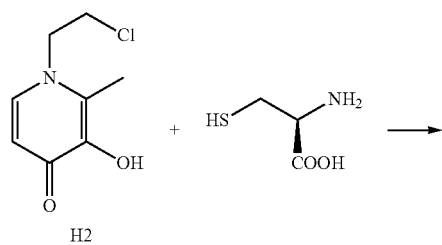

The title compound was prepared according to the procedure for L-H3, but using D-cysteine instead of L-cysteine as the starting material. Yield 71%. HPLC ($t_R$): 32.1 min (linear gradient: 50% B for the first 4 min, increased linearly to 100% B 60 min) $[\alpha]_D^{20}$=+19.5° (c=1.0, H₂O). H¹ NMR (250 MHz, CDCl3+D2O), 3.89 (m, 1H), 2.91 (d, 5.0 Hz, 2H), 3.07 (m, 2H), 3.78 (m, 2H), 7.10 (d, J=7.0 Hz, 1H), 7.90 (d, J=8.1 Hz, 1H), 2.50 (s, 3H). Mass spectrometry: calculated for C₁₄H₁₈N₂O₄S m/z [M+H]⁺=273.32. found [M+H]⁺=273.40

(iv) Synthesis of N-propargyl S-(2-methyl-3-hydroxy-4-pyridinon-1-ylethyl)-D-cysteine. (M11b, Appendix VI)

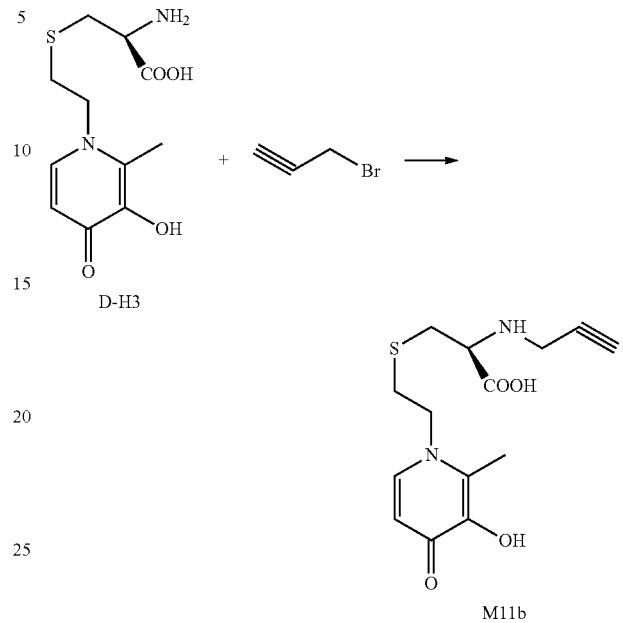

M11b

The title compound M11b was synthesized according to the procedure for M12b, but using S-(2-methyl-3-hydroxy-4-pyridinon-1-ylethyl)-D-cysteine (D-H3) instead of S-(2-methyl-3-hydroxy-4-pyridinon-1-ylethyl)-L-cysteine as the starting compound. Yield 70%, $[\alpha]_D^{20}$=+17.3. ¹H NMR (250 MHz, CHCl₃+D₂O): 2.30 (m, 1H), 3.40 (d, J=5.6 Hz, 2H), 4.01 (m, 1H), 2.98 (d, 5.0 Hz, 2H), 3.07 (m, 2H), 3.78 (m, 2H), 7.20 (d, J=7.0 Hz, 1H), 7.89 (d, J=8.1 Hz, 1H), 2.58 (s, 3H). Mass spectrometry: calculated for C₁₄H₁₈N₂O₄S m/z [M+H]⁺=311.37. found [M+H]⁺=311.30.

Example 10

Synthesis of N-propargylglycine hydroxamate (M37, Appendix V)

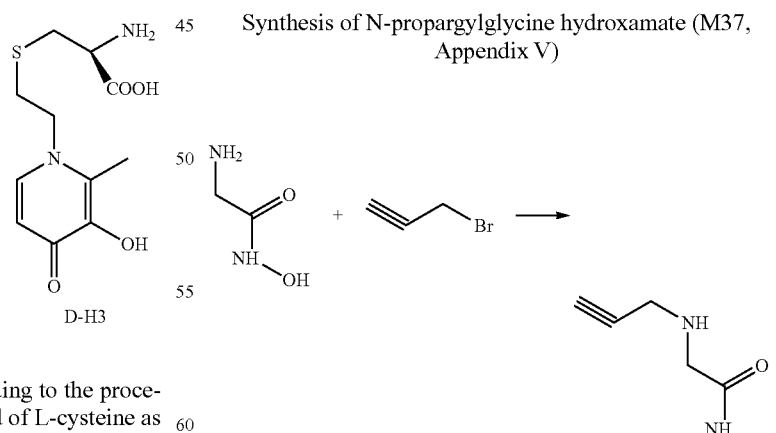

M37

Propargyl bromide (356.9 mg, 3 mmol) was slowly added to a mixture of glycine hydroxamate (270 mg, 3 mmol) and diisopropylethylamine (407.1 mg, 3.15 mmol) in CHCl₃ (20 ml) at 0° C. The mixture was stirred for 24 h at room temperature, and CHCl₃ (50 ml) was added. The solution was washed with 5% NaHCO₃ (3×50 ml), brine (2×50 ml), and then dried over Na₂SO₄. The solution was filtered and evaporated to dryness to give the title compound M37: 192 mg, 50% yield. $^1$H NMR (250 MHz, CHCl₃+D₂O) 2.33 (m, 1H), 3.33 (d, J=5.6 Hz, 2H), 3.13 (s 2H). Mass spectrometry: calculated for $C_5H_8N_2O_2S$ m/z [M+H]$^+$=129.13. found [M+H]$^+$=129.20.

Example 11

Synthesis of N-(4-methylpiperazin-1-ylmethylcarbonyl),N-propargyl glycine hydroxamate (M38, Appendix V)

The title compound was prepared by reaction of N-t-butoxy 2-(N-chloroacetyl,N-propargyl)amino-acetamide (H14, Appendix VII) with N-methyl piperazine. Compound H4 was obtained by reaction of N-t-butoxy 2-amino-acetamide with chloroacetyl chloride and propargyl bromide, as follows:
(i) Synthesis of N-t-butoxy 2-(N-chloroacetyl-N-propargyl) amino-acetamide (H4)

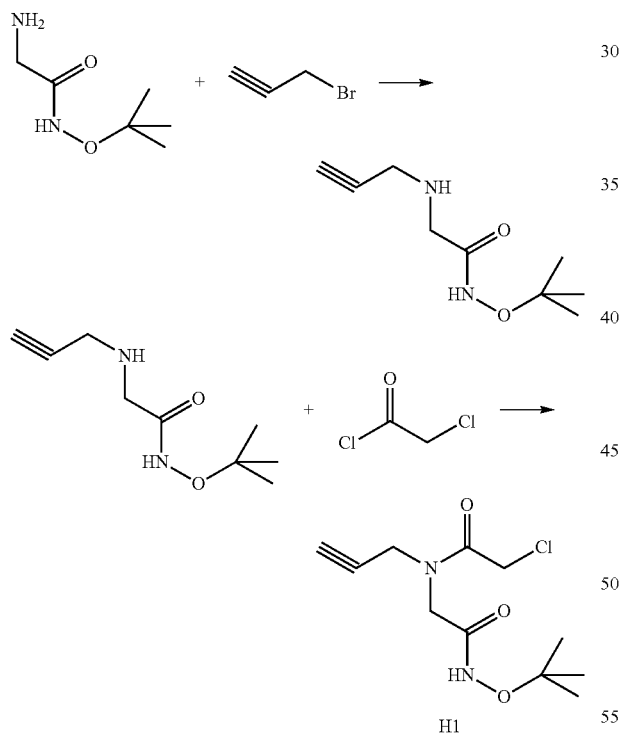

Propargyl bromide (356.9 mg, 3 mmol) was slowly added to a mixture of 2-amino-N-t-butoxy-acetamide (438.6 mg, 3 mmol) and diisopropylethylamine (407.1 mg, 3.15 mmol) in CHCl₃ (20 ml) at 0° C. The mixture was stirred for 24 h at room temperature, and CHCl₃ (50 ml) was added. The solution was washed with 5% NaHCO₃ (3×50 ml), brine (2×50 ml), and then dried over Na₂SO₄. The solution was filtered and evaporated to dryness. The residue was dissolved in diisopropylethylamine (258 mg, 2 mmol) in CH₂Cl₂ (25 ml) at room temperature, and chloroacetyl chloride (0.239 mL, 339 mg, 3 mmol) was slowly added at 0° C. over 30 min. After 2 h of stirring at room temperature, the solvent was removed by vacuum. The resulted residue was dissolved in Et₂OAc (60 ml) and washed with saturated NaHCO₃ (2×50 ml), brine (2×50 ml) and dried over Na₂SO₄ overnight. Evaporation in vacuum gave the title compound H4: 390 mg, 50% yield. $^1$H NMR (250 MHz, CHCl₃) 2.23 (m, 1H), 3.31 (d, J=5.6 Hz, 2H), 3.13 (s 2H). 4.85 (s 2H), 1.38 (s, 9H). Mass spectrometry: calculated for $C_{11}H_{17}N_2O_3$ m/z [M+H]$^+$=261.72. found [M+H]$^+$=261.61.

(ii) Synthesis of N-(4-methylpiperazin-1-ylmethylcarbonyl)-N-propargyl glycine hydroxamate (M38, Appendix V)

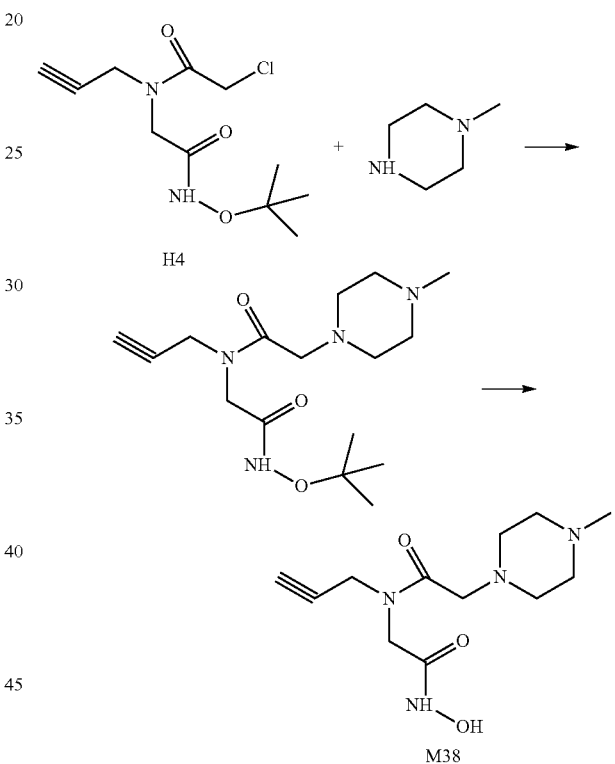

N-methylpiperazine (100 mg, 1 mmol, 1 eq) was added to a stirred solution of chloroform (5 ml), diisopropylethylamine (0.348 ml, 2 mmol, 2 eq) and H4 obtained in step (i) above (261 mg, 1 mmol) at room temperature After being stirred for 24 h at room temperature, 10 ml of CHCl₃ was then added and the solution was washed with 5% NaHCO₃ (3×10 ml), brine (2×10 ml), and then dried over Na₂SO₄. The solution was filtered and evaporated to dryness. The residue was dissolved in a solution of TFA:H₂O:TES:thioanisole (85:5:5:5) (5 ml), and stirred for 1 h at room temperature. After removal of the solvent under vacuum, the residue was dissolved in EtOAc (50 ml), washed with saturated NaHCO₃ (3×20 ml), brine (2×10 ml), and then dried over Na₂SO₄. Evaporation in vacuum gave the title compound M38: 160 mg, 60% yield. $^1$H NMR (250 MHz, CHCl₃+D₂O) 2.30 (m, 1H), 3.31 (d, J=5.6 Hz, 2H), 3.13 (s 2H), 2.83 (s, 3H), 2.44 (s, 8H), 3.87 (s, 2H) Mass spectrometry: calculated for $C_{12}H_{20}N_4O_3$ m/z [M+H]$^+$=269.31. found [M+H]$^+$=269.40.

Example 12

Synthesis of N-[4-(2-hydroxyethyl)piperazin-1-ylmethylcarbonyl), N-propargylglycine hydroxamate (M39, Appendix V)

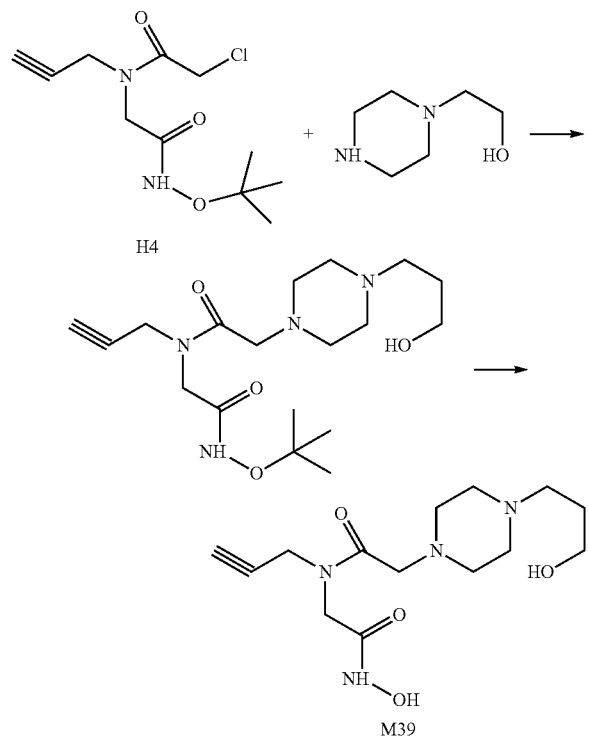

M39

The title compound M39 was synthesized according to the procedure for M38 in Example 11 above, but using 4-(2-hydroxyethyl)piperazine instead of N-methylpiperazine as the starting material. Yield 72%. Mass spectrometry: calculated for $C_{13}H_{22}N_4O_4$ m/z $[M+H]^+=299.34$. found $[M+H]^+=299.40$. $^1$H NMR (250 MHz, $CHCl_3+D_2O$): 2.25 (m, 1H), 3.31 (d, J=5.6 Hz, 2H), 3.13 (s 2H), 4.01 (dd, J=5.6, 1.5 Hz, 2H), 3.56 (dd, J=6.6, 1.5 Hz, 2H), 2.44 (s, 8H), 3.87 (s, 2H).

Example 13

Synthesis of N-[4-ethoxycarbonylpiperazin-1-ylmethylcarbonyl), N-propargylglycine hydroxamate (M40, Appendix V)

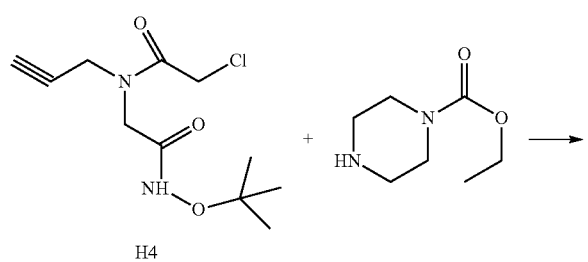

M40

The title compound M40 was prepared as described in Example 11 above, but using 4-ethoxycarbonylpiperazine instead of N-methylpiperazine as the starting material. Yield 78%. Mass spectrometry: calculated for $C_{14}H_{22}N_4O_5$ m/z $[M+H]^+=327.35$. found $[M+H]^+=327.28$. $H^1$ NMR (250 MHz $CDCl_3+D_2O$): 1.28 (dd, J=7.1, 7.1 Hz 3H), 3.81 (s, 2H), 2.44 (s, 4H), 3.43 (s, 4H), 4.01 (dd, J=14.21, 7.12 Hz, 2H), 2.33 (m, 1H), 3.33 (d, J=5.6 Hz, 2H), 3.13 (s, 2H).

Example 14

General Peptide Synthesis

The peptides used in the preparation of the compounds of the invention of formula I such as those depicted in Appendix I, are prepared by the general method as described below.

Unless otherwise stated, all chemicals and reagents were of analytical grade. Trifluoroacetic acid (TFA) for high performance liquid chromatography (HPLC) was obtained from Merck (Darmstadt, Germany). N-9-fluorenylmethoxycarbonyl (Fmoc)-protected amino acid derivatives and Rink amide resins were purchased from Novabiochem (Laufelfingen, Switzerland).

The peptides were prepared manually by solid-phase peptide synthesis using Fmoc chemistry following the company's protocols. N-α-Fmoc-amino acid derivatives were used in the synthesis. N-Methyl morpholine (NMM) and benzotriazol-1-yloxy-tris-pyrrolidino-phosphonium hexafluorophsphate (PyBOP) and, when necessary, a combination of 1,3-dicyclohexylcarbodiimide (DCC) and 1-hydroxybenzotriazole (HOBO, were utilized as coupling agents. N-methyl pyrrolidone (NMP) and DMF were used as solvent. Before each coupling, the deprotection of the α-amino group was achieved by reaction with 20% piperidine. All synthesized peptides were deprotected and cleaved from the resin using a solution of TFA:triethylsilane (TES):thioanisole:water (85:5:5:5). The cleavage mixtures were filtered and the peptides were precipitated from the solution with peroxide-free dry ether at 0° C. Precipitated peptides were washed with cold dry ether, dissolved in water or water/acetonitrile solution, and lyophilized. The crude peptides were subjected to semi-preparative HPLC purification, performed on a Waters system composed of two model 510 pumps, model 680 automated gradient controller, and model 441 absorbance detector (Waters, Milford, Mass.). The column effluents were monitored by UV absorbance at 214/254 nm. HPLC prepacked columns employed (Merck, Darmstadt, Germany) were LichroCART 250-10 mm containing Lichrosorb RP-18 (7 m) for semipreparative purifications and Lichrospher 100 RP-18, 250-4 mm (5 m) for analytical separations. Separations were achieved using gradients of acetonitrile in water containing 0.1% TFA. The solutions containing purified peptides were lyophilized overnight. Molecular weights of all peptides were confirmed by mass spectrometry. Mass spectrometry was performed on a Micromass Platform LCZ4000 (Manchester, UK) utilizing electron spray ionization method. For amino acid composition analysis, peptides were hydrolyzed in 6 N HCl at 100° C. for 24 h under vacuum, and the hydrolyzates were analyzed with a Dionex Automatic Amino Acid Analyzer.

Example 15

Synthesis of VIP analog derivative containing a 8-hydroxyquinoline (HQ) group—Fmoc-KKC(HQ)L-NH$_2$ (M7, Appendix II)

Vasoactive intestinal peptide (VIP) is a 28-mer peptide known to provide neuroprotection against β-amyloid toxicity in models of Alzheimer's disease. Mapping of the active site of VIP lead to a peptide of four amino acids: Lys-Lys-Tyr-Leu. An analog of this VIP fragment was prepared by replacing the Tyr residue by a Cys residue for linking to a 8-hydroxyquinoline (HQ) residue, thus obtaining the compounds of the invention M7 (Appendix II) and M7A (Appendix I) (see Example 16 below). Although both compounds M7 and M7A were given the same connotation Fmoc-KKC(HQ)L-NH$_2$ in Appendices II and I, respectively, it is clear from the structural formula of M7A that it carries a propargylamino group linked to the methylene radical at position 5 of the 8-hydroxyquinolinyl (HQ) radical.

To Rink amide resin (71 mg, 33 μmole) was added 2 ml 20% piperidine in NMP. After 5 minute shaking, the solution was drained and the resin was washed three times with DMF. To the resin was added Fmoc-Leu-OH (47 mg, 132 μmole, 4 eq) and PyBOP (69 mg, 132 μmole, 4 eq) in 1 ml DMF, and NMM (29 μl, 264 μmol, 8 eq). The resulting mixture was then shaken for 1 h. The liquid was drained and a second coupling was performed with equal amounts of Fmoc-Leu-OH, PyBOP and NMM. The third coupling was performed via DCC/HOBt activation: Fmoc-Leu-OH (47 mg, 132 μmole, 4 eq), HOBt (18 mg, 132 μmol, 4 eq), and DCC (132 μml 1N DMF, 132 μmol, 4 eq) were dissolved in 1 ml DMF. After 1 hour cooling, the precipitated dicyclohexylurea (DCU) was removed and the solution was added to the resin. After shaking overnight and draining the solution, the resin was washed (DMFx3, DCMx3). A negative ninhydrin test indicated the completion of the coupling reaction. Next three coupling cycles with Fmoc-Cys(Mmt)-OH, Fmoc-Lys(Boc)-OH, Fmoc-Lys(Boc)-OH, respectively were carried out according to the procedure above (both PyBOP and DCC). At the completion of all four coupling circles, the resulting resin was treated with a solution of TFA:TES:DCM (dichloromethane) (1:5:94 v/v) to remove the Mmt (4-methoxytrityl) protecting group.

A solution of 5-chloromethyl-8-hydroxyquinoline (32 mg, 165 μmol, 5 eq) and NMP (17 mg, 20 μl, 5 eq) in DMF/DCM (1 ml) were added to the resin and the mixture was shaken overnight. A negative DTNB (5,5'-dithio-bis-(2-nitrobenzoate) test indicated the completion of the reaction. The resulting HQ-modified peptide was cleaved from the resin using a solution of TFA:H$_2$O:TES:thioanisole (85:5:5:5) and precipitated with ether. The crude HQ-modified title peptide M7 was further purified by semi-preparative HPLC, as described above. Yield: 4.8 mg (5.5 μmol; 16.7%, based on the initial amino acid resin loading). Mass spectrometry: m/z 870.6 (MH+) calculated 870.1. Amino acid analysis after hydrolysis with 6 M HCl at 110° C. for 22 h: Leu 1.00, Lys 2.16. Cys could not be detected due to its destruction under the acidic conditions of hydrolysis.

Example 16

Synthesis of VIP analog derivative containing a 8-hydroxyquinoline (HQ) group and a propargylamino group—Fmoc-KKC(HQ)L-NH$_2$ (M7A, Appendix I)

(i) Synthesis of 5-(N-tert-butoxycarbonyl,N-propargyl)aminomethyl-8-t-butoxy-quinoline (H5, Appendix VII)

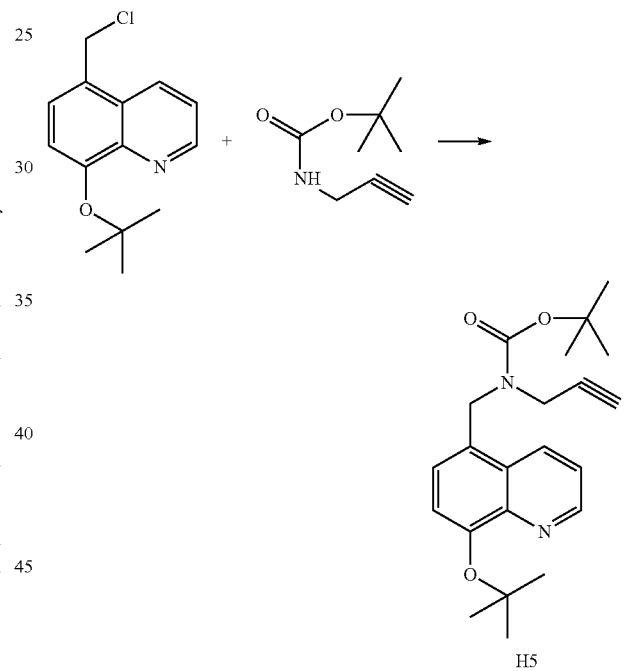

H5

5-Chloromethyl-8-hydroxyquinoline was protected as 5-chloromethyl-8-t-butoxy-quinoline, and propargylamine was converted into N-(tert-butoxycarbonyl)-propargylamine according to known procedures.

N-(tert-Butoxycarbonyl)propargylamine (310 mg, 2 mmol) was added in portions over 30 min to a stirred suspension of NaH (88 mg of 60% dispersion in oil, 2.2 mmol) in DMF (5 ml), under nitrogen. After the H$_2$ gas evolution had ceased, 5-chloromethyl-8-O-t-butyl-quinoline (600 mg, 2.4 mmol) in DMF (2 ml) was added dropwise below 30° C. (cold-water bath). Stirring was continued for 3 h and the reaction mixture was partitioned between EtOAc (3×30 ml) and H$_2$O (50 ml). The combined EtOAc solutions were washed with water, dried over Na$_2$SO$_4$ and evaporated to a buff solid which was washed with hexane and vacuum dried, giving the title compound: 443 mg (60%), $^1$H NMR (250 MHz, CHCl$_3$) 1.31 (s, 9H), 1.41 (s, 9H), 2.29 (m, 1H), 3.27 (s, 2H), 3.91 (s, 2H), 7.25 (d, J=8.0 Hz, 1H), 7.57 (d, J=8.0 Hz, 1H), 7.96 (dd, J=8.7, 5.5 Hz, 1H), 8.88 (d, J=5.4 Hz, 1H), 9.22 (d, J=8.7 Hz, 1H); Mass spectrometry: calculated for $C_{22}H_{28}N_2O_5$ m/z $[M+H]^+$=369.47. found $[M+H]^+$=369.54.

(ii) Synthesis of 5-(propargylaminobromomethyl)-8-hydroxyquinoline (H6, Appendix VII)

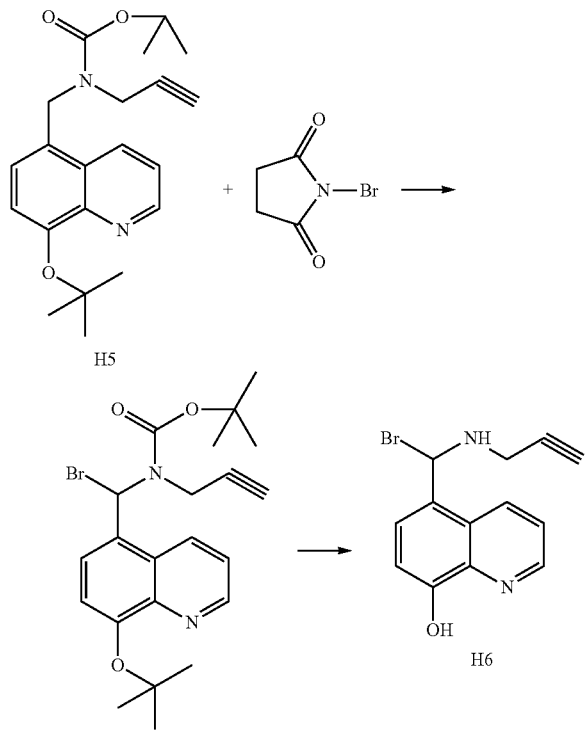

Compound H5 from step (i) above (368 mg, 1 mmol) and N-bromosuccinimide (231 mg, 1.3 mmol) were dissolved in 5 ml of $CCl_4$. To this solution was added benzoyl peroxide (2.5 mg, 0.01 mmol), and the reaction mixture was heated at reflux for 12 h. After reflux, the solution was cooled to 0° C., and the solid precipitate was filtered. The filtrate was washed with 1 M aqueous $Na_2CO_3$, saturated aqueous $NaS_2O_3$, and brine. The organic layer was dried ($Na_2SO_4$), filtered, and evaporated to dryness in vacuum. The residue was dissolved in a solution of TFA:$H_2O$:TES:thioanisole (85:5:5:5) (5 ml). After 1 h, HPLC indicated complete removal of the protecting groups. The solution was evaporated to dryness and the residue was dissolved in water (10 ml) and then basified with $Na_2CO_3$ (pH 11), and extracted with $Et_2OAc$ (3×50 ml). The organic layer was washed with brine (2×50 ml) and dried over $Na_2SO_4$ overnight. Evaporation in vacuum gave the title compound H6: 218 mg, 75% yield. $^1$H NMR (250 MHz, $CHCl_3$) 2.23 (m, 1H), 3.27 (s, 2H), 5.10 (s, 1H), 7.25 (d, J=8.0 Hz, 1H), 7.57 (d, J=8.0 Hz, 1H), 7.96 (dd, J=8.7, 5.5 Hz, 1H), 8.88 (d, J=5.4 Hz, 1H), 9.22 (d, J=8.7 Hz, 1H); Mass spectrometry: calculated for $C_{22}H_{28}N_2O_5$ m/z $[M+H]^+$=292.14. found $[M+H]^+$=292.04.

(iii) Synthesis of VIP analog derivative containing a 8-hydroxyquinoline (HQ) group and a propargylamino group—M7A (Appendix I, Scheme A)

A solution of H6 of step (ii) above (48 mg, 0.165 mmol, 5 eq) and NMP (17 mg, 0.020 ml, 5 eq) in DMF/$CH_2Cl_2$ (1 ml) was added to the resin (0.033 mmol, 1 eq) obtained in Example 15 above and the mixture was shaken overnight. A negative DTNB test indicated the completion of the reaction.

The resulting HQ-modified peptide was cleaved from the resin using a solution of TFA:$H_2O$:TES:thioanisole (85:5:5:5) and precipitated with ether. The crude HQ-modified peptide M7A was further purified by semi-preparative HPLC ($t_R$): 35.1 min (linear gradient: 50% B for the first 4 min, increased linearly to 100% B 60 min). Yield: 6 mg (5.5 μmol; 16.7%, based on the initial amino acid resin loading). Mass spectrometry: calculated for $C_{49}H_{63}N_9O_7S$ m/z $[M+H]^+$= 923.68. found m/z $[M+H]^+$=923.91. Amino acid analysis after hydrolysis with 6 M HCl at 110° C. for 22 h: Leu 1.00, Lys 2.10. Cys could not be detected due to its destruction under the acidic conditions of hydrolysis.

Example 17

Synthesis of VIP analog derivative containing a 8-hydroxyquinoline (HQ) group—Stearyl-KKC(HQ)L-$NH_2$ (M6, Appendix II)

Fmoc-Lys(Boc)-Lys(Boc)-Cys(Mmt)-Leu-[Rink amide resin] 33 μmol was synthesized as described above in Example 15. After removing the Fmoc group, the free N-terminal function was coupled with stearic acid (38 mg, 132 μmol, 4 eq) according to the procedure described above. A negative ninhydrin test indicated the completion of the coupling reaction. The peptide was cleaved from the resin using a solution of TFA:$H_2O$:TES:thioanisole (85:5:5:5) and precipitated with ether. A solution of 5-chloromethyl-8-hydroxyquinoline (32 mg, 165 μmol, 5 eq) and NMP (17 mg, 20 μl, 5 eq) in DMF/$CH_2Cl_2$. (1 ml) was added to the crude peptide. The mixture was shaken overnight at room temperature. A negative DTNB test indicated the completion of the reaction. Upon completion of the reaction, the solution was drained, and the crude peptide was further purified by semi-preparative HPLC to yield: 4.6 mg (5.0 μmol; 15.3%, based on the initial amino acid-resin loading). HPLC ($t_R$): 38.1 min (linear gradient: 50% B for the first 4 min, increased linearly to 100% B 60 min), $t_R$=47.5 min for St-KKCLNH$_2$ at the same conditions. Mass spectrometry: m/z 914.9 (MH+), (calculated 914.3). Amino acid analysis after hydrolysis with 6 M HCl at 110° C. for 22 h: Leu 1.00, Lys 2.21. Cys could not be detected due to its destruction under the acidic conditions of hydrolysis.

Example 18

Synthesis of VIP analog derivative containing a 8-hydroxyquinoline (HQ) group and a propargylamino group—Stearyl-KKC(HQ)L-$NH_2$ (M6A, Appendix I)

To the resin (33 μmol, 1 eq) obtained in Example 17 above was added a solution of 5-(propargylaminobromomethyl)-8-hydroxyquinoline H6 (48 mg, 0.165 mmol, 5 eq) and NMP (17 mg, 0.020 ml, 5 eq) in DMF/$CH_2Cl_2$ (1 ml). The mixture was then shaken overnight. A negative DTNB test indicated the completion of the reaction. The resulting HQ-modified peptide was cleaved from the resin using a solution of TFA: $H_2O$:TES:thioanisole (85:5:5:5) and precipitated with ether. The crude HQ-modified peptide M6A was further purified by semi-preparative HPLC ($t_R$): 40.1 min (linear gradient: 50% B for the first 4 min, increased linearly to 100% B 60 min). Yield: 5.8 mg (6 μmol; 18%, based on the initial amino acid resin loading). Mass spectrometry: calculated for $C_{52}H_{87}N_9O_6S$ m/z $[M+H]^+$=967.37. found m/z $[M+H]^+$= 967.21. Amino acid analysis after hydrolysis with 6 M HCl at 110° C. for 22 h: Leu 1.00, Lys 2.20. Cys could not be detected due to its destruction under the acidic conditions of hydrolysis.

Example 19

Synthesis of Substance P analog derivative containing a 8-hydroxyquinoline (HQ) group—[Cys$^7$(HQ)]-substance P (M27, Appendix II)

[Cys$^7$]-Substance P (9.0 mg, 6.9 µmol) was dissolved in N,N'-dimethylformamide (DMF) (350 µl), and NMM (7.6 µl, 69 µmol, 10 equiv) was added. After being stirred for 1 h at room temperature, 5-chloromethyl-8-hydroxyquinoline hydrochloride (1.5 mg, 7.6 µmol, 1.1 equiv) in 150 µl mixed solvent (DMF:DMSO:CH$_3$CN 3:3:1) was added dropwise. The reaction mixture was stirred overnight at room temperature. The progress of the reaction was monitored by analytical HPLC. When necessary, additional 5-chloromethyl-8-hydroxyquinoline hydrochloride was added for completion of the reaction. Upon completion of the reaction, the crude peptide was precipitated with ice-cold tert-butyl methyl ether/petroleum ether, collected by centrifugation, and then purified by semi-preparative HPLC. $t_R$=32.27 min (linear gradient: t B=0% at 1.0 ml/min over 5 min; B=0%-58% at 1.0 ml/min over 45 min), ($t_R$=32.28 min for [Cys$^7$]-substance P in the same conditions). Amino acid analysis after hydrolysis with 6 M HCl at 110° C. for 22 h: Lys 1.00, Arg 1.09, Glu 2.03, Gly 1.32, Pro 1.93, Leu 1.01, Phe 0.96, Cys 0.92. Cys was detected using S-(8-hydroxyquinolin-5-ylmethyl)-L-cysteine as standard reference. Met could not be detected due to its destruction under the acidic conditions of hydrolysis. Mass spectrometry: calculated for C$_{67}$H$_{101}$N$_{19}$O$_{14}$S$_2$ m/z [M+H]$^+$=1461.77. found [M+H]$^+$=1461.15.

Example 20

Synthesis of Substance P analog derivative containing a 8-hydroxyquinoline (HQ) group—[Cys$^8$(HQ)]-substance P (M28, Appendix II)

Compound M28 was synthesized by the method described in Example 19 above for compound M27 using the appropriate starting materials. The crude peptide M28 was further purified by semi-preparative HPLC. $t_R$=32.10 min (linear gradient: t B=0% at 1.0 ml/min over 5 min; B=0%-58% at 1.0 ml/min over 45 min), ($t_R$=32.89 min for [Cys$^8$]-substance P in the same conditions). Mass spectrometry: calculated for C$_{67}$H$_{101}$N$_{19}$O$_{14}$S$_2$ m/z [M+H]$^+$=1461.77. found [M+H]$^+$=1461.17. Amino acid analysis after hydrolysis with 6 M HCl at 110° C. for 22 h: Lys 1.00, Arg 1.18, Glu 1.96, Gly 1.22, Pro 1.77, Leu 0.92, Phe 0.91, Cys 0.96. Cys was detected using S-(8-hydroxyquinolin-5-ylmethyl)-L-cysteine as standard reference. Met could not be detected due to its destruction under the acidic conditions of hydrolysis.

Example 21

Synthesis of Substance P analog derivative containing a 8-hydroxyquinoline (HQ) group and a propargylamino group—[Cys$^7$(HQ)]-Substance P (M27A, Appendix I)

To [Cys$^7$]-substance P (9.0 mg, 6.9 mmol, 1 eq) in DMF (350 µl) was added NMM (7.6 µl, 69 µmol, 10 equiv). After being stirred for 1 h at room temperature, a solution of 5-(propargylamino-bromomethyl)-8-hydroxyquinoline H6 (2.2 mg, 7.6 µmol, 1.1 eq) in 150 µl mixed solvent (DMF:DMSO:CH$_3$CN 3:3:1) was added dropwise. The reaction mixture was stirred overnight at room temperature. The progress of the reaction was monitored by analytical HPLC. When necessary, additional 5-(propargylamino-bromomethyl)-8-hydroxyquinoline was added for completion of the reaction. Upon completion of the reaction, the crude peptide was precipitated with ice-cold tert-butyl methyl ether/petroleum ether, collected by centrifugation, and then purified by semi-preparative HPLC. $t_R$=35.27 min (linear gradient: t B=0% at 1.0 ml/min over 5 min; B=0%-58% at 1.0 ml/min over 45 min), ($t_R$=32.28 min for [Cys$^7$]-substance P in the same conditions). Amino acid analysis after hydrolysis with 6 M HCl at 110° C. for 22 h: Lys 1.00, Arg 1.10, Glu 2.01, Gly 1.32, Pro 1.93, Leu 1.03, Phe 0.96, Cys 0.99. Cys was detected using S-(8-hydroxyquinolin-5-yl-(propargylamino-methyl)-L-cysteine as standard reference. Met could not be detected due to its destruction under the acidic conditions of hydrolysis. Mass spectrometry: calculated for C$_{70}$H$_{104}$N$_{20}$O$_{14}$S$_2$ m/z [M+H]$^+$=1514.78. found [M+H]$^+$=1514.25.

Example 22

Synthesis of Substance P analog derivative containing a 8-hydroxyquinoline (HQ) group and a propargylamino group—[Cys$^8$(HQ)]-Substance P (M28A, Appendix I)

The title compound M28A was synthesized according to the procedure for M27A in Example 21 above, but using [Cys$^8$]-substance P instead of [Cys$^7$]-substance P as the starting material. Yield 75%. Amino acid analysis after hydrolysis with 6 M HCl at 110° C. for 22 h: Lys 1.00, Arg 1.08, Glu 2.11, Gly 1.22, Pro 1.93, Leu 1.01, Phe 1.04, Cys 0.99. Cys was detected using S-(8-hydroxyquinolin-5-yl-(propargylamino-methyl)-L-cysteine as standard reference. Met could not be detected due to its destruction under the acidic conditions of hydrolysis. Mass spectrometry: calculated for C$_{70}$H$_{104}$N$_{20}$O$_{14}$S$_2$ m/z [M+H]$^+$=1514.78. found [M+H]$^+$=1514.88.

Example 23

Synthesis of GnRH analog derivative containing a 8-hydroxyquinoline (HQ) group—L-Cys$^5$(HQ)]GnRH (M8, Appendix II)

Compound M8 was synthesized according to the method for synthesizing compound M27 described in Example 19 above, using the appropriate starting materials. The crude peptide M8 was further purified by semi-preparative HPLC. $t_R$=26.02 min (linear gradient: t B=0% at 1.0 ml/min over 5 min; B=0%-75% at 1.0 ml/min over 45 min), ($t_R$=27.54 min for [Cys$^5$]GnRH under the same conditions). Mass spectrometry: calculated for C$_{59}$H$_{78}$N$_{18}$O$_{13}$S m/z [M+H]$^+$=1279.43. found [M+H]$^+$=1279.86. Amino acid analysis after hydrolysis with 6 M HCl at 110° C. for 22 h: Arg 1.00, Ser 1.09, Glu 0.92, Gly 2.21, His 0.88, Pro 0.89, Leu 0.89, Cys 0.85. Cys was detected using S-(8-hydroxyquinolin-5-ylmethyl)-L-cysteine as standard reference.

Example 24

Synthesis of GnRH analog derivative containing a 8-hydroxyquinoline (HQ) group—D-Cys$^6$(HQ)]GnRH (M22, Appendix II)

Compound M22 was synthesized according to the method for synthesizing compound M27 described in Example 19 above, using the appropriate starting materials. Upon completion of the reaction, the crude peptide M22 was precipitated with ice-cold tert-butyl methyl ether (3 ml). After centrifugation, the solid was dissolved in DDW and purified by preparative HPLC to yield mg (mmol; %). $t_R$=30.82 min (linear gradient: t B=0% at 1.0 ml/min over 5 min; B=0%-58% at 1.0 ml/min over 45 min), ($t_R$=32.57 min for [D-Cys$^6$]GnRH under the same conditions). Mass spectrometry: calculated for $C_{66}H_{84}N_{18}O_{14}S$ m/z [M+H]$^+$=1386.55. found [M+H]$^+$=1386.71.

Example 25

Synthesis of GnRH analog derivative containing a 8-hydroxyquinoline (HQ) group and a propargylamino group—L-Cys$^5$(HQ-Pr)]GnRH (MBA, Appendix I)

[Cys$^5$]GnRH (7.7 mg, 6.9 mmol) was dissolved in DMF (350 µl), and NMM (7.6 µml, 69 µmol, 10 equiv) was added. After being stirred for 1 h at room temperature, 5-(propargyl-aminobromomethyl)-8-hydroxyquinoline H6 (2.2 mg, 76 mmol, 1.1 eq) in 150 µl mixed solvent (DMF:DMSO:CH$_3$CN 3:3:1) was added dropwise. The reaction mixture was stirred overnight at room temperature. The progress of the reaction was monitored by analytical HPLC. When necessary, additional H6 was added for completion of the reaction. Upon completion of the reaction, the crude peptide was precipitated with ice-cold tert-butyl methyl ether/petroleum ether, collected by centrifugation. The crude peptide M8A was further purified by semi-preparative HPLC. $t_R$=30.12 min (linear gradient: t B=0% at 1.0 ml/min over 5 min; B=0%-75% at 1.0 ml/min over 45 min), ($t_R$=27.54 min for [Cys$^5$]GnRH under the same conditions). Yield: 7.2 mg (5.4 mmol; 78%). Mass spectrometry: calculated for $C_{62}H_{81}N_{19}O_{13}S$ m/z [M+H]$^+$=1332.46. found [M+H]$^+$=1332.66. Amino acid analysis after hydrolysis with 6 M HCl at 110° C. for 22 h: Arg 1.00, Ser 1.09, Glu 0.99, Gly 2.21, His 0.98, Pro 0.89, Leu 0.89, Cys 0.85. Cys was detected using S-(8-hydroxyquinolin-5-yl-(propargylaminomethyl)-L-cysteine as standard reference.

Example 26

Synthesis of GnRH analog derivative containing a 8-hydroxyquinoline (HQ) group and a propargylamino group—D-Cys$^6$(HQ-Pr)GnRH (M22A, Appendix I)

The title compound M22A was synthesized according to the procedure for M27A in Example 23 above, but using [D-Cys$^6$]GnRH instead of [Cys$^5$]GnRH as the starting material. Yield 70%. Mass spectrometry: calculated for $C_{69}H_{87}N_{20}O_{13}S$ m/z [M+H]$^+$=1439.56. found [M+H]$^+$=1439.66. Amino acid analysis after hydrolysis with 6 M HCl at 110° C. for 22 h: Arg 1.00, Ser 1.09, Glu 0.99, Tyr 1.03, Gly 1.11, His 0.98, Pro 0.99, Leu 0.89, Cys 0.85. Cys was detected using S-(8-hydroxyquinolin-5-yl-(propargylaminomethyl)-L-cysteine as standard reference Example 27

Synthesis of enkephalin analog derivatives containing a 8-hydroxyquinoline (HQ) group—YGGC(HQ)L (M18), YGGC(HQ)M (M19), C(HQ)GGFL (M20), C(HQ)GGFM (M21) (Appendix II)

(i) General Procedure for the Synthesis of Compounds M18, M19, M20, M21

To a solution of Cys$^1$Met$^5$-enkephalin or Cys$^1$Leu$^5$-enkephalin (25 mop in DMF (150 µl) was added NMM (26 µl, 250 µmol). After stirring 1 h at room temperature, 5-chloromethyl-8-hydroxyquinoline hydrochloride (61 mg, 25 µmol) in 250 µl mixed solvent (DMF:DMSO:CH$_3$CN 3:3:1) was added dropwise. The reaction mixture was stirred overnight at room temperature. The progress of the reaction was monitored by analytical HPLC. When necessary, additional 5-chloromethyl-8-hydroxyquinoline hydrochloride was added for completion of the reaction. Upon completion of the reaction, the crude peptide was precipitated with ice-cold tert-butyl methyl ether/petroleum ether, collected by centrifugation, and then purified by semipreparative HPLC (linear gradient: t B=0% at 1.0 ml/min over 5 min; B=0%-58% at 1.0 ml/min over 55 min).

(ii) [Cys$^4$(HQ)]-Leu$^5$-enkephalin (M18, Appendix II)

Mass spectrometry: calculated for $C_{32}H_{40}N_6O_8S$ m/z [M+H]$^+$=669.76. found [M+H]$^+$=669.62

(iii) [Cys$^4$(HQ)]-Met$^5$-enkephalin (M19, Appendix II)

HPLC. $t_R$=26.43 min (linear gradient: t B=0% at 1.0 ml/min over 5 min; B=0%-58% at 1.0 ml/min over 55 min) ($t_R$=23.87 min for [Cys$^1$]-Leu$^5$-enkephalin in the same conditions). Mass spectrometry: calculated for $C_{32}H_{40}N_6O_8S$ m/z [M+H]$^+$=687.80. found [M+H]$^+$=687.79.

(iv) [Cys$^1$(HQ)]-Leu$^5$-enkephalin (M20, Appendix II)

HPLC. $t_R$=29.56 min (linear gradient: t B=0% at 1.0 ml/min over 5 min; B=0%-58% at 1.0 ml/min over 55 min) ($t_R$=27.92 min for [Cys$^1$]-Leu$^5$-enkephalin under the same conditions). Mass spectrometry: calculated for $C_{32}H_{40}N_6O_7S$ m/z [M+H]$^+$=653.76. found [M+H]$^+$=653.48

(v) [Cys$^1$(HQ)]-Met$^5$-enkephalin (M21, Appendix II)

Mass spectrometry: calculated for $C_{31}H_{38}N_6O_7S_2$ m/z [M+H]$^+$=671.80. found [M+H]$^+$=671.43.

Example 28

Synthesis of enkephalin analog derivatives containing a 8-hydroxyquinoline (HQ) group and a propargylamino group—YGGC(HQ)L (M18A), YGGC(HQ)M (M19A), C(HQ)GGFL (M20A), C(HQ)GGFM (M21A) (Appendix I)

(i) General Procedure for the Synthesis of Compounds M18A, M19A, M20A, M21A (Appendix I, Scheme C)

The modified enkephalin peptide ([Cys$^4$]-Leu$^5$-enkephalin, [Cys$^4$]-Met$^5$-enkephalin, [Cys$^1$]-Leu$^5$-enkephalin, or [Cys$^1$]-Met$^5$-enkephalin) (25 µmol) was dissolved in DMF (150 µl), and NMM (26 µl, 250 µmol) was added. After 1 h of stirring at room temperature, 5-(propargylaminobromomethyl)-8-hydroxy-quinoline H6 (25 µmol) in 250 µl mixed solvent (DMF:DMSO:CH$_3$CN 3:3:1) was added dropwise. The reaction mixture was stirred overnight at room temperature. The progress of the reaction was monitored by analytical HPLC. When necessary, additional H6 was added for completion of the reaction. Upon completion of the reaction, the crude peptide was precipitated with ice-cold tert-butyl methyl ether/petroleum ether, collected by centrifugation, and then purified by semi-preparative HPLC (linear gradient: t B=0% at 1.0 ml/min over 5 min; B=0%-58% at 1.0 ml/min over 55 min).

(ii) [Cys$^4$(propargyl-HQ)]-Leu$^5$-enkephalin (M18A, Appendix I)

Yield 70%, HPLC. $t_R$=28.43 min (linear gradient: t B=0% at 1.0 ml/min over 5 min; B=0%-58% at 1.0 ml/min over 55 min) ($t_R$=25.87 min for [Cys$^4$]-Leu$^5$-enkephalin in the same conditions) Mass spectrometry: calculated for $C_{35}H_{43}N_7O_8S$ m/z [M+H]$^+$=722.80. found [M+H]$^+$=722.62.

(iii) [Cys$^4$(propargyl-HQ)]-Met$^5$-enkephalin (M19A, Appendix I)

Yield 60%, HPLC. $t_R$=27.83 min (linear gradient: t B=0% at 1.0 ml/min over 5 min; B=0%-58% at 1.0 ml/min over 55 min) ($t_R$=23.87 min for [Cys$^4$]-Met$^5$-enkephalin in the same conditions). Mass spectrometry: calculated for $C_{35}H_{43}N_7O_8S$ m/z [M+H]$^+$=740.84. found [M+H]$^+$=740.70.

(iv) [Cys$^1$(propargyl-HQ)]-Leu$^5$-enkephalin (M20A, Appendix I)

Yield 72%, HPLC. $t_R$=30.16 min (linear gradient: t B=0% at 1.0 ml/min over 5 min; B=0%-58% at 1.0 ml/min over 55 min)=27.92 min for [Cys$^1$]-Leu$^5$-enkephalin under the same conditions). Mass spectrometry: calculated for $C_{35}H_{43}N_7O_7S$ m/z [M+H]$^+$=706.80. found [M+H]$^+$=706.88.

(v) [Cys$^1$(propargyl-HQ)]-Met$^5$-enkephalin (M21A, Appendix I)

Yield 78%, HPLC. $t_R$=27.26 min (linear gradient: t B=0% at 1.0 ml/min over 5 min; B=0%-58% at 1.0 ml/min over 55 min) ($t_R$=25.90 min for [Cys$^1$]-Leu$^5$-enkephalin under the same conditions). Mass spectrometry: calculated for $C_{34}H_{41}N_7O_7S_2$ m/z [M+H]$^+$=724.84. found [M+H]$^+$=724.94.

Example 29

Synthesis of VIP, GnRH, and Substance P analog derivatives containing a propargylamino group and a hydroxamate group—Compounds M6B, M7B, M8B, M22B, M27B, and M28B (n=1) (Appendix V, Scheme C)

(i) General Procedure for the Synthesis of Hydroxamate Compounds M6B, M7B, M8B, M22B, M27B, and M28B (n=1) (Appendix V)

The modified peptide (7 μmol, 1 equiv.) (St-KKCL-NH$_2$, Fmoc-KKCL-NH2, [Cys$^5$]GnRH, [D-Cys$^6$]GnRH, [Cys$^7$]-substance P, or [Cys$^8$]-substance P synthesized as described above) was dissolved in DMF (350 μl), and NMM (7.6 μl, 70 μmol, 10 equiv) was added. After 1 hour of stirring at room temperature, N-t-butoxy 2-(N-chloroacetyl-N-propargyl)-amino-acetamide (H4) (2 mg, 7.7 μmol, 1.1 equiv) in 150 μl DMF was added dropwise. The mixture was stirred overnight at room temperature. The progress of the reaction was monitored by analytical HPLC. When necessary, additional H4 was added for completion of the reaction. Upon completion of the reaction, the solvent was removed under vacuum. To the residue was added a solution (2 mL) of TFA:H$_2$O:TES:thioanisole (85:5:5:5). The mixture was stirred for 1 h and then precipitated with ice-cold tert-butyl methyl ether/petroleum ether, collected by centrifugation; the crude modified peptide was further purified by semi-preparative HPLC.

(ii) Synthesis of Compound M6B (n=1)(Appendix V)

Yield 71%, HPLC ($t_R$): 25.1 min (linear gradient: 50% B for the first 4 min, increased linearly to 100% B 40 min). Mass spectrometry: calculated for $C_{46}H_{85}N_9O_8S$ m/z [M+H]$^+$=925.29. found m/z [M+H]$^+$=925.21 Amino acid analysis after hydrolysis with 6 M HCl at 110° C. for 22 h: Leu 1.00, Lys 2.20. Cys could not be detected due to its destruction under the acidic conditions of hydrolysis.

(iii) Synthesis of Compound M7B (n=1)(Appendix V)

Yield: 68% HPLC ($t_R$): 25.1 min (linear gradient: 50% B for the first 4 min, increased linearly to 100% B 50 min. Mass spectrometry: calculated for $C_{43}H_{61}N_9O_9S$ m/z [M+H]$^+$=881.07. found m/z [M+H]$^+$=881.15. Amino acid analysis after hydrolysis with 6 M HCl at 110° C. for 22 h: Leu 1.00, Lys 2.15. Cys could not be detected due to its destruction under the acidic conditions of hydrolysis.

(iv) Synthesis of Compound M8B (n=1)(Appendix V)

Yield: 70%. HPLC $t_R$=29.1 min (linear gradient: t B=0% at 1.0 ml/min over 5 min; B=0%-75% at 1.0 ml/min over 45 min), ($t_R$=27.54 min for [Cys$^5$]GnRH under the same conditions). Mass spectrometry: calculated for $C_{56}H_{79}N_{19}O_{15}S$ m/z [M+H]$^+$=1291.57. found [M+H]$^+$=1291.66. Amino acid analysis after hydrolysis with 6 M HCl at 110° C. for 22 h: Arg 1.00, Ser 1.12, Glu 0.95, Gly 2.16, His 0.98, Pro 0.89, Leu 0.99. Cys could not be detected due to its destruction under the acidic conditions of hydrolysis.

(v) Synthesis of Compounds M22B (n=1)(Appendix V)

Yield 75%. HPLC $t_R$=25.1 min (linear gradient: t B=0% at 1.0 ml/min over 5 min; B=0%-100% at 1.0 ml/min over 45 min), ($t_R$=23.54 min for [D-Cys$^6$]-GnRH under the same conditions). Mass spectrometry: calculated for $C_{63}H_{85}N_{19}O_{16}S$ m/z [M+H]$^+$=1397.53. found [M+H]$^+$=1397.61 Amino acid analysis after hydrolysis with 6 M HCl at 110° C. for 22 h: Arg 1.00, Ser 1.09, Glu 0.99, Tyr 1.03, Gly 1.11, His 0.98, Pro 0.99, Leu 0.89. Cys could not be detected due to its destruction under the acidic conditions of hydrolysis.

(vi) Synthesis of compound M27B (n=1) (Appendix V)

Yield 60%. HPLC. $t_R$=33.27 min (linear gradient: t B=0% at 1.0 ml/min over 5 min; B=0%-58% at 1.0 ml/min over 45 min), ($t_R$=32.28 min for [Cys$^7$]-substance P in the same conditions). Amino acid analysis after hydrolysis with 6 M HCl at 110° C. for 22 h: Lys 1.00, Arg 1.10, Glu 2.01, Gly 1.32, Pro 1.93, Leu 1.03, Phe 0.96. Cys and Met could not be detected due to its destruction under the acidic conditions of hydrolysis. Mass spectrometry: calculated for $C_{64}H_{102}N_{20}O_{16}S_2$ m/z [M+H]$^+$=1472.75. found [M+H]$^+$=1472.55.

(vii). Synthesis of Compound M28B (n=1) (Appendix V)

Yield 65%. HPLC. $t_R$=32.91 min (linear gradient: t B=0% at 1.0 ml/min over 5 min; B=0%-58% at 1.0 ml/min over 45 min), ($t_R$=31.28 min for [Cys$^8$]-substance P in the same conditions). Amino acid analysis after hydrolysis with 6 M HCl at 110° C. for 22 h: Lys 1.00, Arg 1.08, Glu 2.11, Gly 1.22, Pro 1.93, Leu 1.01, Phe 1.04, Cys 0.99. Cys and Met could not be detected due to its destruction under the acidic conditions of hydrolysis. Mass spectrometry: calculated for $C_{63}H_{100}N_{20}O_{16}S_2$ [M+H]$^+$=1458.73. found [M+H]$^+$=1458.84.

II Biological Section:
Methods
(a) Metal Binding Properties

It is known that 8-hydroxyquinoline is a strong chelator for iron and has a higher selectivity for iron over copper. It is an important precondition for the antioxidative-type drugs because it is the excessive iron stores and iron-mediated generation of free radicals in the brain that are thought to be associated with neurodegenerative diseases. Therefore, only chelators with a higher selectivity for iron over copper are expected to chelate iron instead of copper and have potential neuroprotective effects. In order to discuss possible correlation between chelating properties of 8-hydroxyquinoline and its derivatives with their anti-oxidative ability, and the correlation between its derivative and the best established iron chelating drug, desferal, with antioxidative properties, a reliable measurement of the stability constants of the newly synthesized compounds is necessary. A spectrophotometric method was used for measurement of the iron-complexes stability constants of the compounds.

(b) Partition Coefficients

The partition coefficient ($P_{ow}$) or the distribution ratio ($D_{ow}$) between octanol and water are most commonly used measures of the hydrophobicity of compounds. $D_{ow}$ can depend on the concentration of solute, but at reasonably low concentrations. If the solute is in the same form in both phases, $D_{ow}$ becomes constant and is called the partition coefficient $P_{ow}$. $P_{ow}$ plays an important role in determining the physico-chemical properties and the behaviour of numerous organic compounds in biological systems. $P_{ow}$ is applied to quantitative structure-activity relationship studies, and as a measure of hydrophobicity. All the partition measurements are carried out using a 1-octanol/water shake-flask procedure (Leo, A J. 1991, "Hydrophobic parameter: measurement and calculation", *Methods Enzymol.* 202:544-91) or simply by the elution time of solute from HPLC column. Thereafter, the transport properties of the iron-complexes are examined in the water/lipid membrane system (liposomes), which mimics biomembranes much better than the octanol/water system (Breuer et al, 1995).

1-Octanol (Riedel-deHaën, synthesis grade (250-270 nm abs. <0.06) and glass distilled deionized water were used as the partitioning solutions. A Hewlett-Packard 8450A diode array spectrophotometer was used for the quantitative determination of the tested com-pounds in the standard solutions and in the partitioned solutions. The aqueous phase stock solutions were shaken with an excess of 1-octanol to presaturate them and were then allowed to stand overnight before use. The 1-octanol stock solutions were also presaturated with 10 mM NaOH and allowed to settle overnight. The experiments were performed in 10-ml stoppered centrifuge tubes. The tubes were inverted gently for 5 min and then, to assure complete phase separation, they were centrifuged for 20 min at 1,000-2,000 g. The aqueous and organic phases were removed separately and analyzed by UV spectrophotometry.

(c) Antioxidative Properties

Free radicals and reactive oxygen species generated in biological systems are thought to be responsible, among other factors, for neurodegenerative diseases. The ability of the compounds to reduce the rate of formation or decrease the overall yield of free radicals and reactive oxygen species in Fenton and Fenton-type reactions is an important precondition for the antioxidative-type drugs. Therefore a reliable measurement of antioxidative properties of the compounds is necessary. When the free radical has a long lifetime, direct electron spin resonance (ESR) spectroscopy may be the convenient way to identify this species. However, for unstable free radicals, like superoxide ($O_2 \overset{\cdot}{O_2^-}$) or hydroxyl radical (.OH) other ways must be used. The influence of the compounds on Fenton and Fenton-type reactions is measured by deoxyribose assay and Spin trapping method.

The deoxyribose assay (Sawahara et al., 1991) is based on the destruction of deoxyribose by hydroxyl radicals, leading to the formation of malondialdehyde (MDA), which reacts on heating with thiobarbituric acid (TBA), at low pH, to give a pink pigment. Visible absorption spectra of this pigment shows very strong and sharp absorbance with maximum at 532 nm.

The "spin trapping" method has been developed to detect and identify low concentration of free radicals in reacting systems. This involves the reaction of a free radical X' with a diamagnetic compound to form a more stable radical product, which is readily observable by EPR (electron paramagnetic resonance) technique. This method consists of using a nitron or nitroso compound to "trap" the initial free radical, as a long-lived nitroxide, (d) Mitochondria Isolation:

Male Sprague-Dawley rats (300-350 g) are decapitated and the brains are immediately isolated and cooled in ice-cold isotonic 10 mM Tris-HCl buffer (pH 7.5) containing 0.25 M sucrose, 2 mM EDTA and 2% bovine serum albumin free of fatty acids (isolation buffer), and homogenized with 50 ml glass-teflon homogenizer with a motor (Heidolf, Germany) at 200 rpm in a 1:10 (w/v) ratio isolation buffer.

The homogenate is centrifuged at 1000 g for 10 min and the resultant supernatant then centrifuged at 10,000 g for 10 min. The pellet is washed with 10 mM Tris-HCl (pH 7.5), 0.25 M sucrose, and centrifuged again at 10,000 g for 10 min This step is then repeated three more times. The pellet is resuspended in 10 mM Tris-HCl (pH 7.5), 0.25 M sucrose at a final concentration of 50-60 mg protein/ml. The samples are stored at −18° C. until use.

(e) Inhibition of Lipid Peroxidation

The ability of the compounds to inhibit lipid peroxidation as initiated by iron and ascorbate is examined in brain mitochondria preparation employing the malondialdehyde procedure (Gassen et al. 1996; Ben-Shachar et al., 1991).

The experiments are carried out in triplicates. 7.5 µM of mitochondrial preparation (0.25 mg protein) are suspended in 750 µM of 25 mM Tris-HCl (pH 7.4) containing 25 µM ascorbic acid. Samples of the drugs to be tested are dissolved in water or ethanol and added to the suspension. The reaction is started by the addition of 2.5 or 5 µM FeSO4 (from a 1 mM stock solution), and incubation for 2 h at room temperature. The reaction is stopped by addition of 750 µl of 20% (w/v) trichloroacetic acid. The samples are centrifuged at 12,000 g for 10 mini. 500 µl of the supernatant is mixed with 500 µl of 0.5% (w/v) thiobarbituric acid and heated t: 95° C. for 30 min. The absorption of thiobarbituric acid derivatives is measured photometrically at X=532 nm. Blank analysis is based on emission of the mitochondria, or of FeSO4, or alternatively, addition of the drugs after incubation.

(f) Neuroprotective Effects

Neuroprotective effects of the iron chelators are determined both in vivo and in vitro systems.

For in vitro experiments, rat pheochromocytoma type 12 (PC12) cells and human neuroblastoma SH-SY5Y cells are used to examine the neuroprotective action of the chelators in response to iron and beta-amyloid toxicity. Cell viability is tested in MTT (2,5-diphenyltetrazolium bromide) and LDH (lactate dehydrogenase) tests as well as measuring dopamine and tyrosine hydroxylase by HPLC and release of alpha-amyloid (soluble) by Western, since these cells are used as models of dopamine and cholinergic neurons.

The protection in vivo is tested in MPTP (1-methyl-4-phenyl-1,2,3,6-tetrahydropyridine) animal model of PD (Parkinson's disease), a very viable and well-established model of neurodegeneration, by measuring striatal dopamine and tyrosine hydroxylase, the markers of dopamine neurons.

(g) PC12 Cell Culture.

Rat PC12 cells, originated from rat pheochromocytoma, were grown at 37° C., in a humid 5% $CO_2$, 95% air environment, in a growth medium containing Dulbecco's modified Eagle's Medium (DMEM, GIBCO, BRL) supplemented with glucose (1 mg/1 ml), 5% fetal calf serum, 10% horse serum, and 1% of a mixture of streptomycin/penicillin. On confluence, the culture was removed and the cells were detached by vigorous washing, centrifuged at 200 g for 5 min and resuspended in DMEM with full serum content. $0.5 \times 10^4$ cells/well were placed in microliter plates (96 wells) precoated with collagen (10 μg/cm$^2$ were allowed to attach for 24 h before treatment).

(h) MTT Tests for Cell Viability.

Twenty-four hours after attachment of the PC12 cells as described in (g), the medium was replaced with DMEM containing 0.1% BSA. The test compounds were added to the cells after 1 h of incubation. After 24 h incubation, the cells were subjected to MTT test as previously described (Gassen et al., 1998). The absorption was determined in a Perkin-Elmer Dual Wavelength Eliza-Reader at $\lambda = 570/650$ nm after automatic subtraction of background readings. The results are expressed as percentage of the untreated control.

Example 30

Iron Chelation in Solution

Iron binding was determined by the chelator capacity for restoring the fluorescence of iron-quenched calcein (CAL), a dynamic fluorescent metallosensor. The iron-scavenging properties of the chelators were assessed in solution, by mixing iron salts with free CAL.

Figure 1B:
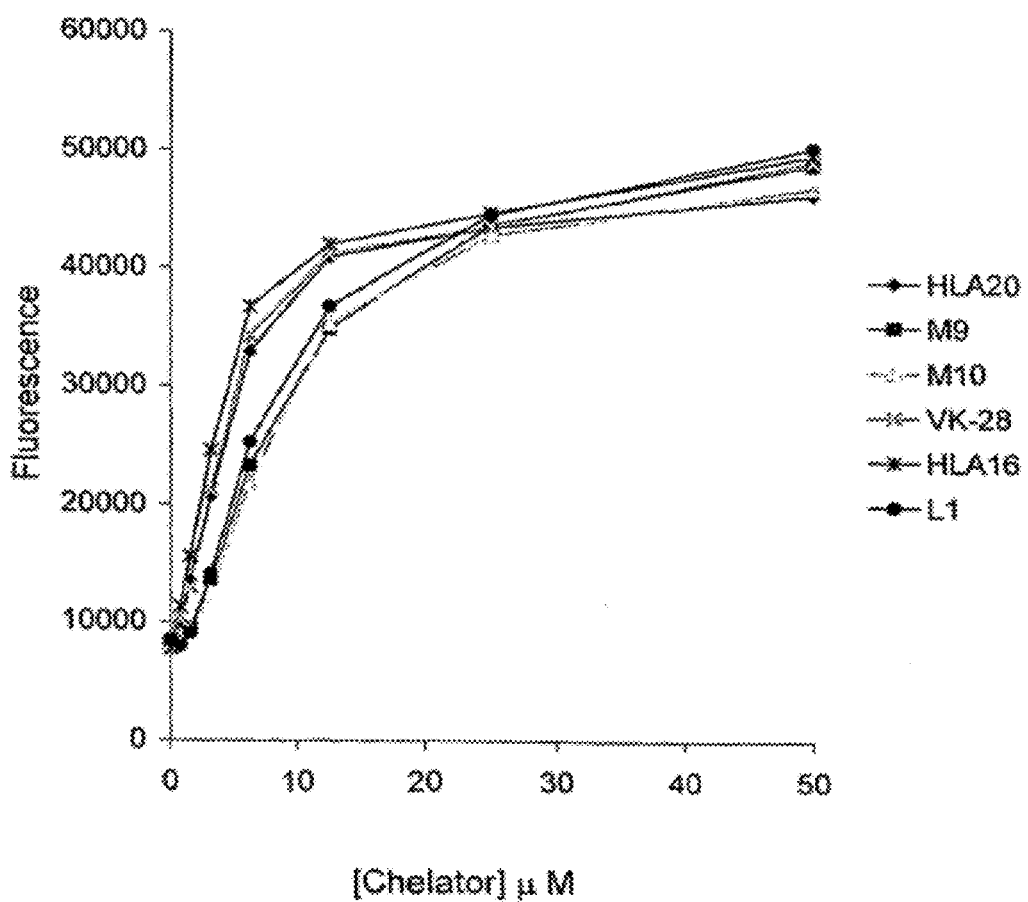
Figure 1C:
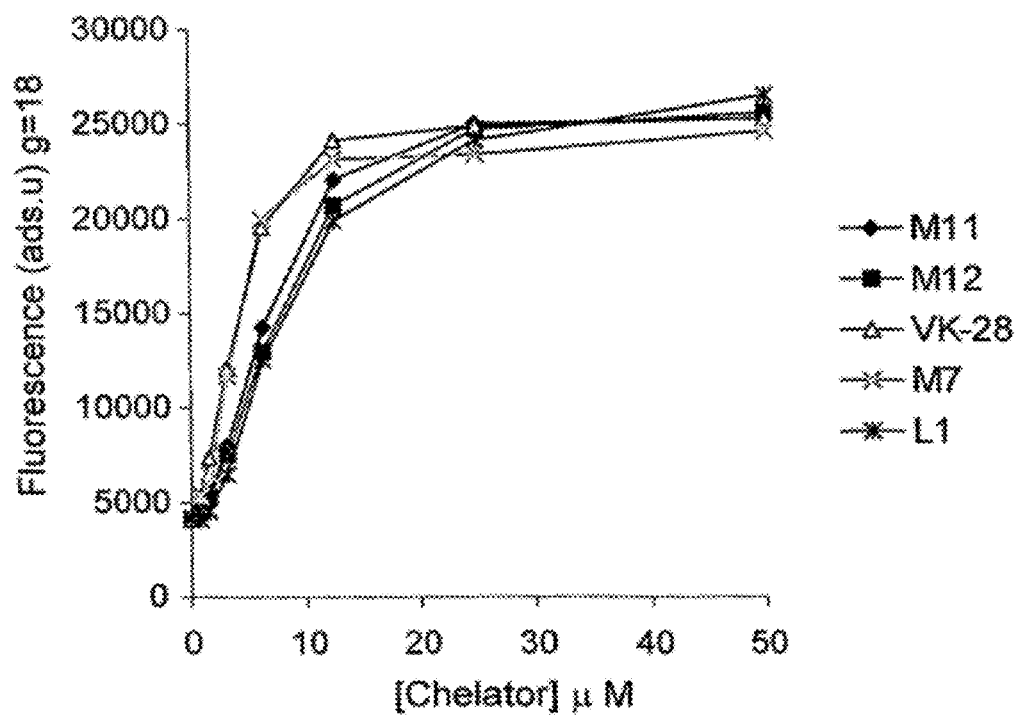

Iron precomplexed calcein (Fe-CAL) solutions of 1 μM (in Hepes 20 mM buffered saline, pH 7.4=HBS) were incubated in the presence of the indicated concentrations of different chelators at room temperature and the fluorescence intensity (475 nm→520 nm) followed with time in a Tecan fluorescence plate reader, using 96-well culture plates (Nunc) at 100 μl final volume. The time-dependent complexation of iron from Fe-CAL by the chelators was followed by fluorescence dequenching. The results are shown in FIGS. 1A-1C. The fluorescence intensity attained after 1 h incubation is shown as a function of the chelator concentration.

The corresponding half maximal dequenching level for the corresponding chelator was (in μM) (rank order from the fastest acting to the slowest):

FIG. 1A: DFO (0.5)(not shown)>>HLA16 (3.5)=HLA20 (3.5)>HLM7 (5.0)>HLM8 (6.0)>HLM9 (7.2)>L1 (8.3).

FIG. 1B: DFO (0.5)(not shown)>>HLA16 (4.4)>VK-28 (5.2)>HLA20 (5.4)>L1 (8.4)>M9 (9.7)>M10 (9.85)

FIG. 1C: DFO (0.5)(not shown)>>VK-28(3.2)>M7 (3.4)>M11 (5.4)>M12 (6)>L1 (6.6).

DFO=desferrioxamine B
L1=1,2-dimethyl-3-hydroxy-pyridin-4-one (deferiprone)

Example 31

Iron permeation of the chelators into K562 cells

The iron-scavenging properties of the chelators were assessed in human erythroleukemia K562 cells, by loading with the permeant CAL-AM probe, in situ formation of free CAL, and binding of cytosolic labile iron. Calcein-AM readily passes through the cell membrane of viable cells because of the enhanced hydrophobicity as compared to Calcein. When Calcein-AM permeates into the cytoplasm, it is hydrolyzed by esterases in cells to the parent Calcein, a pH-independent, cytosolic fluorescent marker, which remains inside of the cell. The time-dependent recovery of fluorescence in the presence of a given chelator provided a continuous measure for the capacity of the chelator to access the iron/CAL-containing compartment.

Calcein uptake and intracellular fluorescence were determined as follows: K562 erythroleukemia cells were pre-loaded with calcein (CAL) by incubation with 0.25 mM of the fluorescent probe CAL-AM for 5 min at 37° C., washed and incubated in HBS medium containing anti-CAL antibodies in order to quench traces of extracellular-associated fluorescence. The suspensions were placed in 96-well plates (100 μl final volume) and analyzed as described above while maintaining the system at 37° C. At the indicated time, the indicated chelator was added so as to reach a final 5 μM concentration.

Figure 2A:
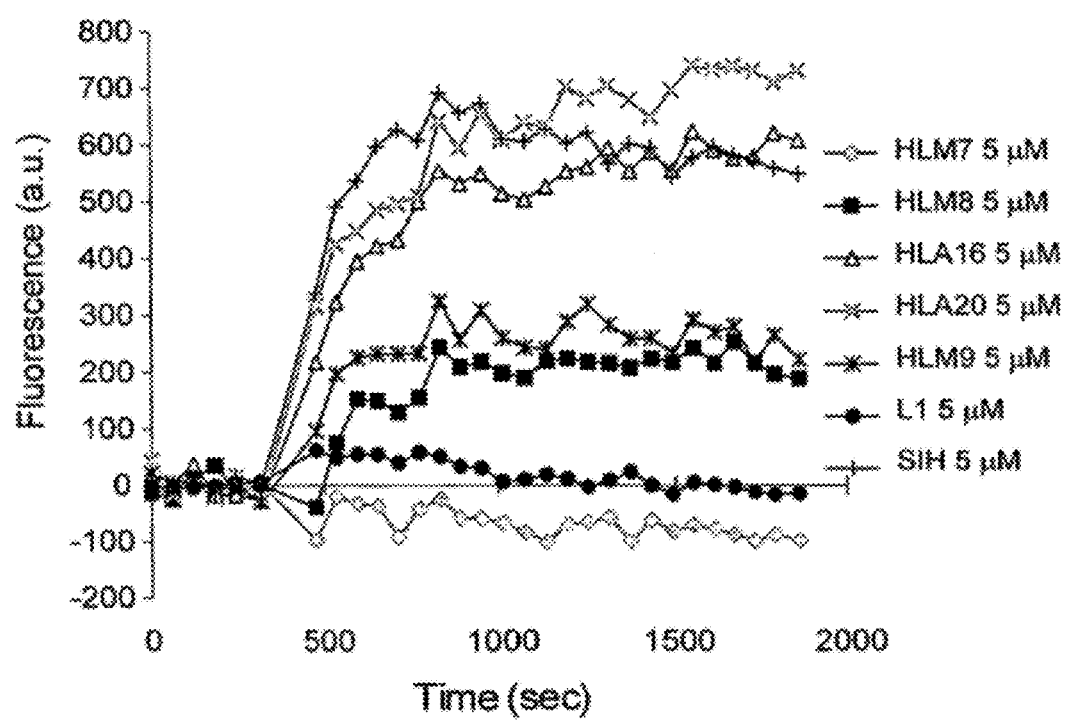
FIGS. 2A-2D show iron permeation into K562 cells of the chelators of the invention HLM7, HLM8, HLM9, HLA16, HLA20 (FIG. 2A), HLA16, HLA20, M9, M10 (FIG. 2B), and M7, M11, M12 (FIG. 2C), HLM9, HLA16, HLA20 (FIG. 2D), and the known iron chelators deferiprone (L1), VK-28 desferrioxamine B (DFO), and salicylaldehyde isonicotinoyl hydrazone (SIH).

The results are shown in FIGS. 2A-2D. The values of half maximal time (sec) and fraction of fluorescence recovery were:

FIG. 2A: SIH: (125, 1)>HLA20 (175, 1)>HLA16 (225, 0.95)>HLM9 (200, 0.50), HLM8 (600, 0.4), L1 (ND)>>DFO (not shown)

Figure 2B:
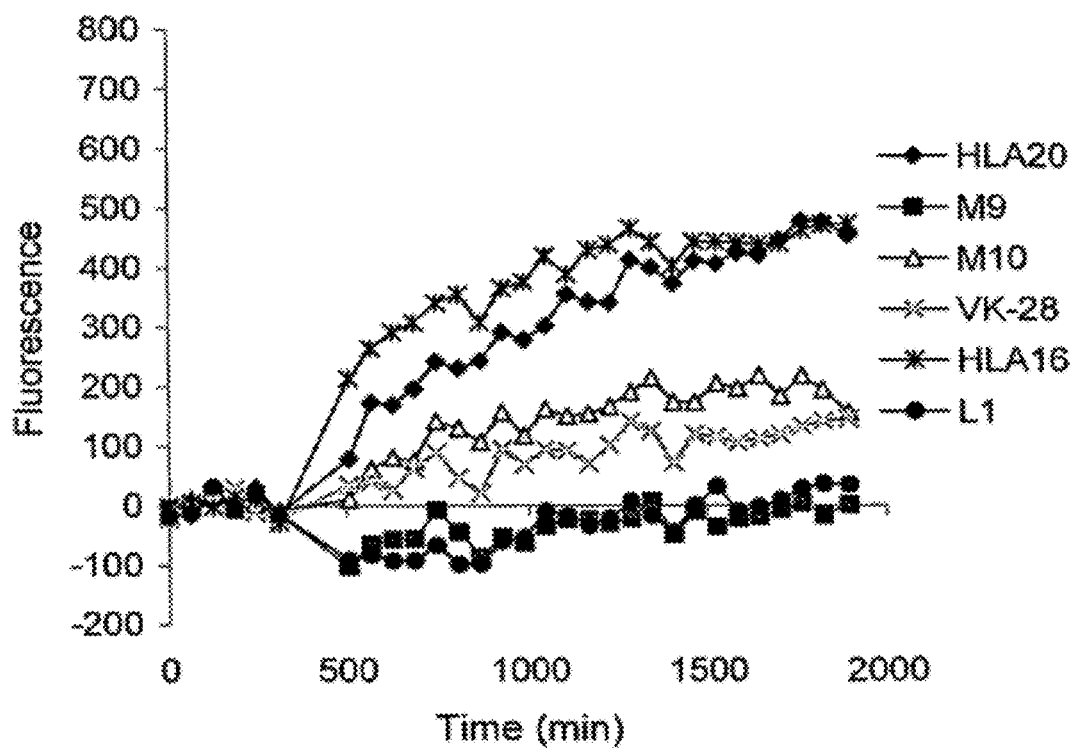

FIG. 2B: HLA16 (220, 1)>HLA20 (390, 1)>M10 (1050)>VK-28 (1250,)>>, L1 & M9 (ND)>>>)>>DFO (not shown)

Figure 2C:
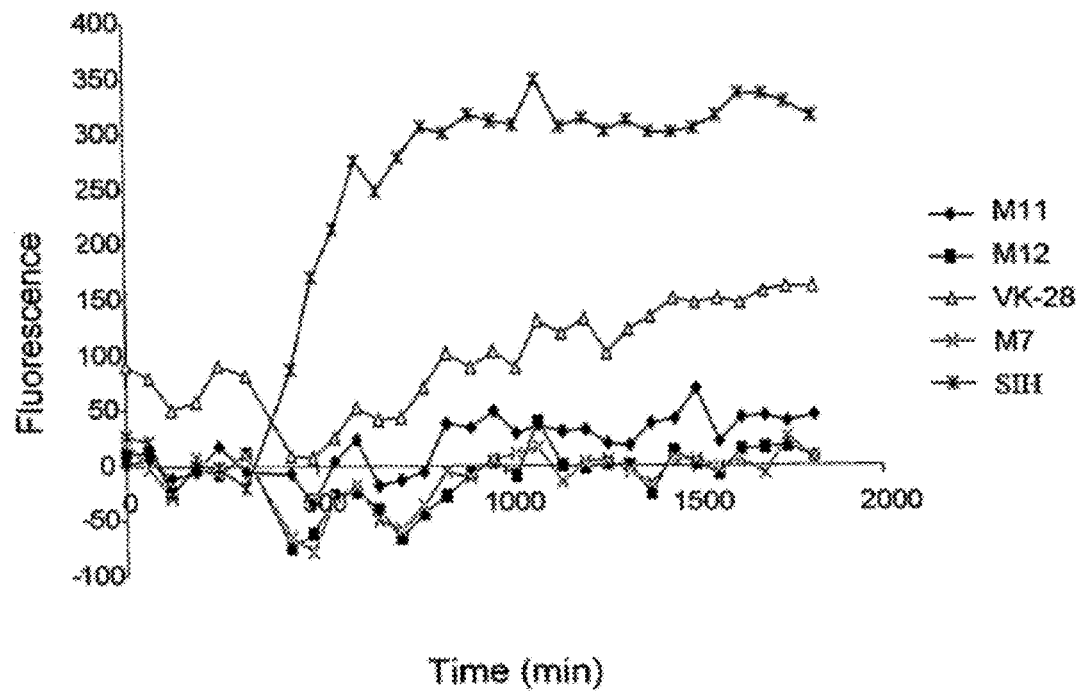

FIG. 2C: SIH: (100, 1)>VK-28 (1500, ?)>>M11, M12, M7 (ND)>>)>>DFO (not shown)

Figure 2D:
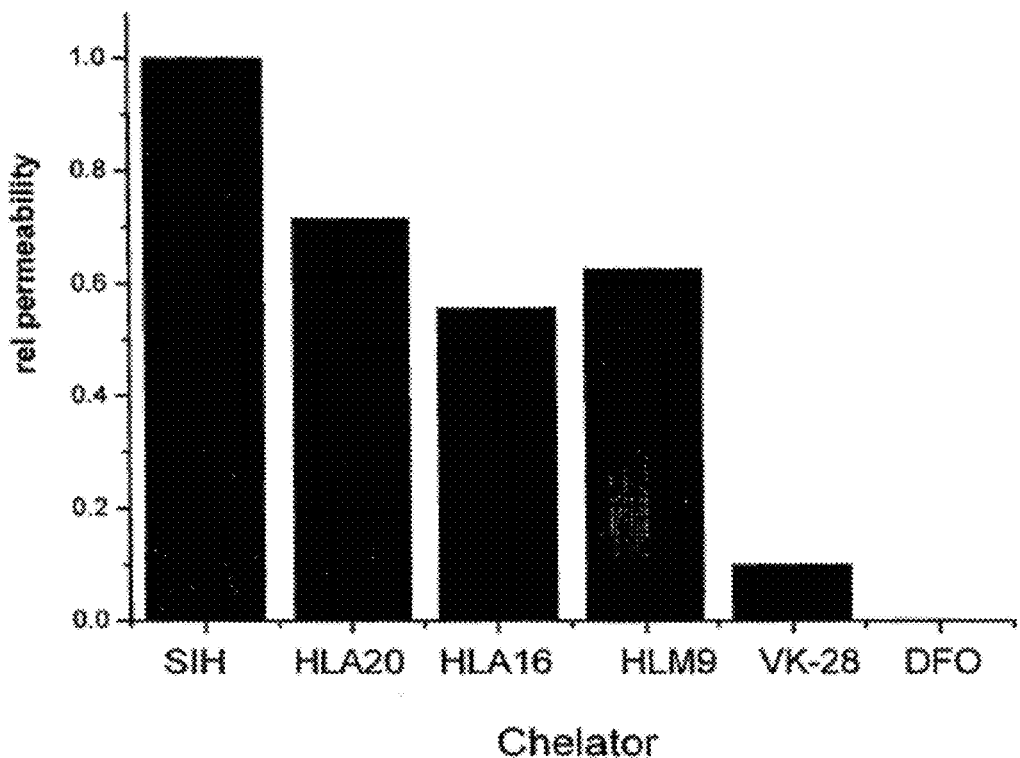

FIG. 2D shows relative permeabilities of the iron chelators HLA20, HLA16, HLM9, VK-28 in K562 cells (values are given relative to those obtained with SIH, for which 1.0 represents an apparent rate constant of 0.005 sec$^{-1}$. (equiv. to a $t_{1/2}$ of ingress of 125 sec for a 5 μM chelator solution).

SIH=salicylaldehyde isonicotinoyl hydrazone.

Example 32

Neuroprotection of Differentiated P19 Cells

This experiment was carried out on P19 mouse embryonal carcinoma cells differentiated to neuronal cells.

Figure 3:
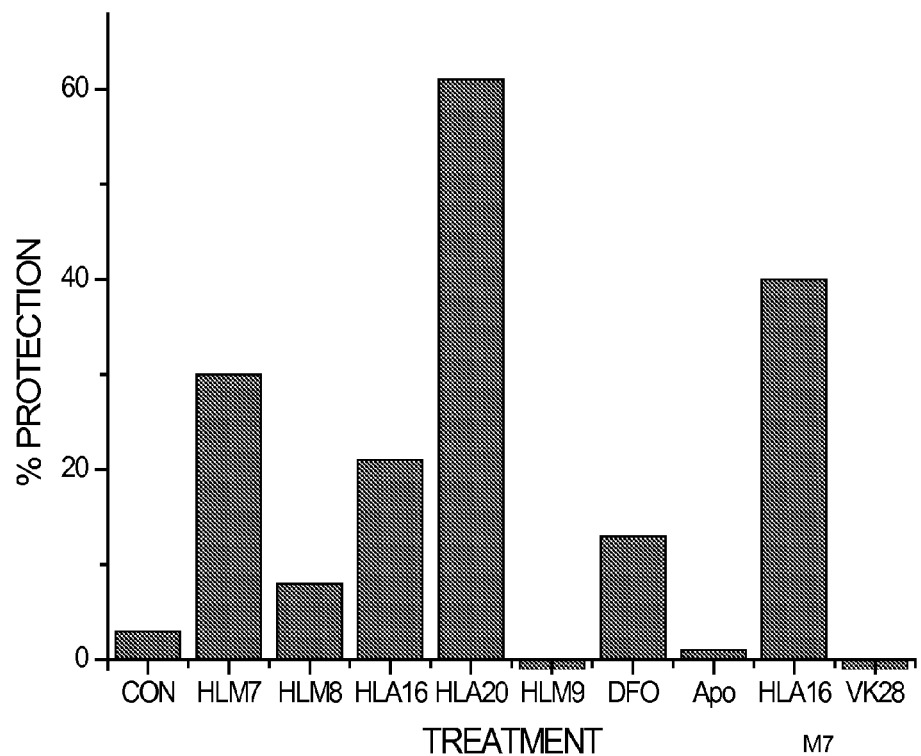
FIG. 3 shows neuroprotective effect of the chelators of the invention HLM7, HLM8, HLM9, HLA16, M7, HLA20 and of apomorphine (Apo) on differentiated neuronal P19 cells treated with 6-OH-dopamine.

Differentiated P19 neuronal cells grown in 96-well culture plates were treated for 6 h with 50 μM 6-OHDA (6-hydroxy-dopamine) in full medium containing either 5 μM of the indicated chelator (HLM7, HLM8, HLM9, HLA16, HLA20, M7, VK-28, DFO) or 1 μM apomorphine (Apo). The cells were subsequently washed and resuspended in fresh medium containing 5% Alamar blue, incubated for 4 h, and the fluorescence monitored at 450 nm exc 590 nm emission (Tecan Safire fluorescence plate reader). The results are shown in FIG. 3. Data are given as % protection, which is equivalent to the % activity relative to the system not treated with 6-OHDA.

Example 33

Neuroprotection of PC12 Cells Against Serum-Deprivation Induced Apoptosis

PC12 cells were grown in serum-free medium alone or in serum-free medium with different concentration of the chelators VK-28, M32, HLA20 and Rasagiline. After 24 h incubation, the cells were subjected to MTT test.

Figure 4A:
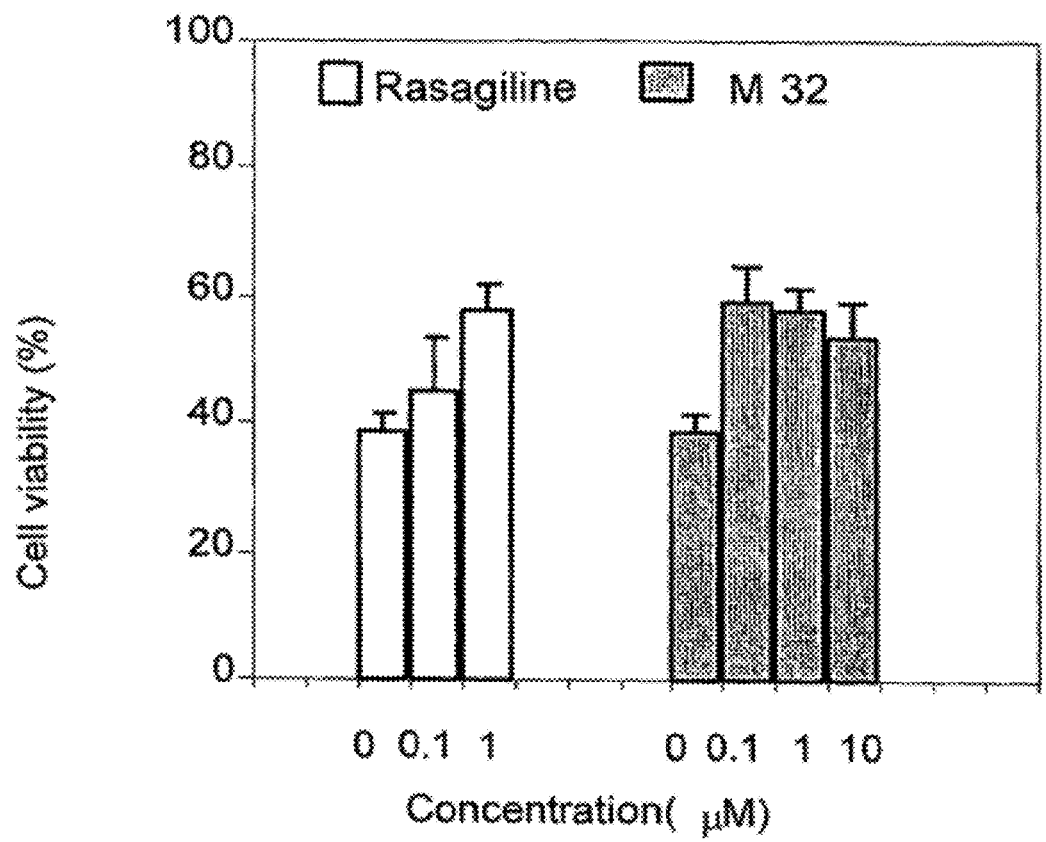
FIGS. 4A-4B show protection by of PC12 cells against serum deprivation-induced apoptosis by the chelators of the invention M32 (FIG. 4A) and HLA20 (FIG. 4B), in comparison to the known chelators Rasa line and VK-28.
Figure 4B:
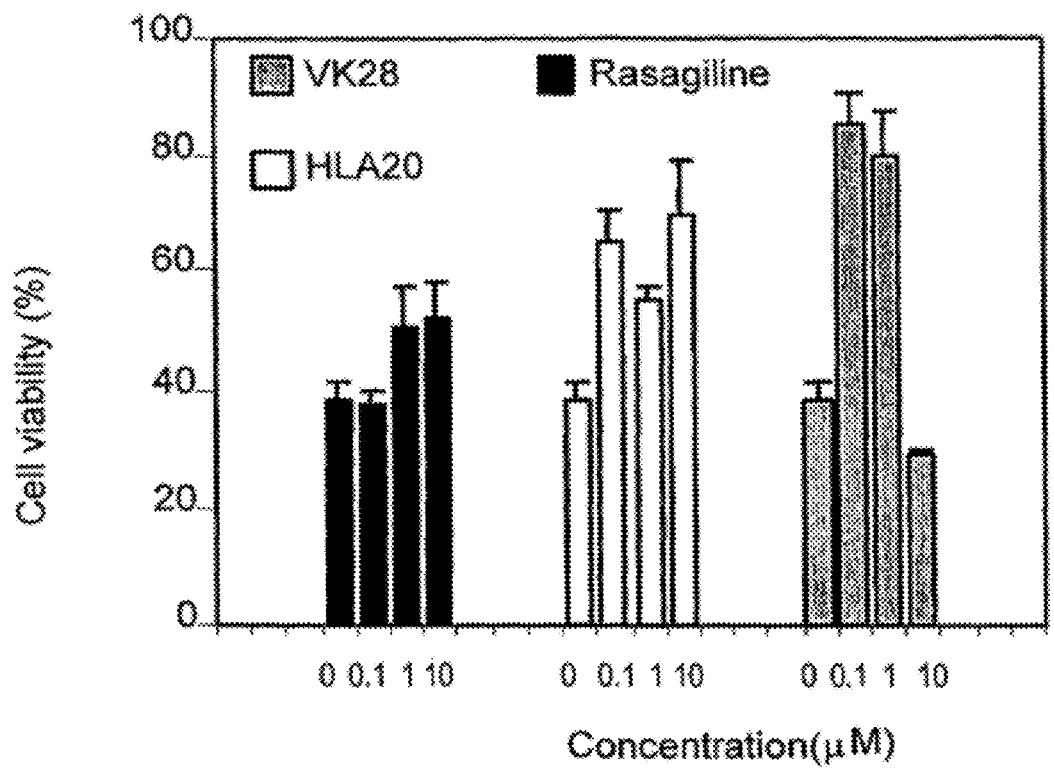

The results are shown in FIGS. 4A-4B. Cell viability was expressed as a percentage of cells cultured in medium supplemented with serum, which served as the control group and was designated as 100%. PC12 cells grown in serum-free medium had a cell viability of 38% (at 24 hr) and were used as a positive control. Experimental data are shown as mean±SD (r=6).

As shown in FIGS. 4A-4B, the chelators VK-28, HLA20 and M32 all protected against PC12 cell death after serum withdrawal. After 24 h incubation, the viability of PC12 cells grown in serum-free medium with 0.1 µM VK-28, 0.1 µM HLA20, or 0.1 µM M32 was significantly different from that in serum-free medium without the chelators (P<0.01). The number of survival cells was elevated to 80%, 65% and 59%, respectively, as compared with the serum-free control group (38%). At ten or hundred times the concentration of the chelators HLA20 (1 or 10 µM) and M32 (1 or 10 µM) there was no significant change in the protection against PC12 cell death induced by serum withdrawal. With concentration of 1 µM, VK-28 also showed a good inhibitory activity against PC12 apoptosis induced by serum withdrawal. However, at the concentration of 10 µM, the toxicity of VK28 became increasingly dominant. This concentration caused about 75% PC12 cell death in serum-free medium.

Example 34

Inhibitory Effects on MAO Activity in Rat Brain

Monoamine oxidase (MAO), an enzyme that plays a crucial role in the metabolic degradation of biogenic amines, exists in two functional forms: MAO-A and MAO-B. The two isoenzymes have different substrate and inhibitor specificities.

i. Preparation of Brain MAO

Rats were decapitated and the brains were quickly taken into a weighted ice-cold sucrose buffer (0.32 M), and their weights were determined. All subsequent procedures were performed at 0-4° C. The brains were homogenized in 0.25 M sucrose (one part tissue to 20 parts sucrose) in a Teflon glass homogenizer followed by the addition of sucrose buffer to a final concentration of 10% homogenate. The homogenates were centrifuged at 600 g for 15 min. The supernatant fraction was taken out and centrifuged at 4500 g for 30 min, the pellet was diluted in 0.32 M sucrose buffer and kept frozen for later assaying of MAO. Protein concentration was determined with Bradford reagent at 595 nm, using bovine serum albumin as a standard.

ii. Determination of MAO Inhibitoy Activity In Vitro

The activity of MAO-A and MAO-B was determined by the adapted method of Tipton & Youdim (1983). The test compound was added to a suitable dilution of the enzyme preparation (70 pg protein for MAO-B and 150 µg MAO-A assay) in 0.05 M phosphate buffer (pH 7.4). The mixture was incubated together with 0.05 M deprenyl/selegiline, a specific inhibitor of MAO-B (for determination of MAO-A) or 0.05 M clorgylin, a specific inhibitor of MAO-A (for determination of MAO-B). Incubation was carried for 1 h at 37° C. before addition of $^{14}$C-5-hydroxytryptamine binoxalate (100 M) for determination of MAO-A, or $^{14}$C-phenylethylamine 100 M for determination of MAO-B, and incubation continued for 30 min or 20 min, respectively. The reaction was stopped with 2 M ice-cold citric acid, and the metabolites were extracted and determined by liquid-scintillation counting in cpm units.

iii. Inhibition of MAO-A and MAO-B by the Iron Chelators

MAO-A and MAO-B activities were determined in rat brain homogenate in vitro following incubation with varying concentrations of the test compounds. The inhibitory activities of the tested compounds are shown in FIGS. 5A-5D.

Figure 5A:
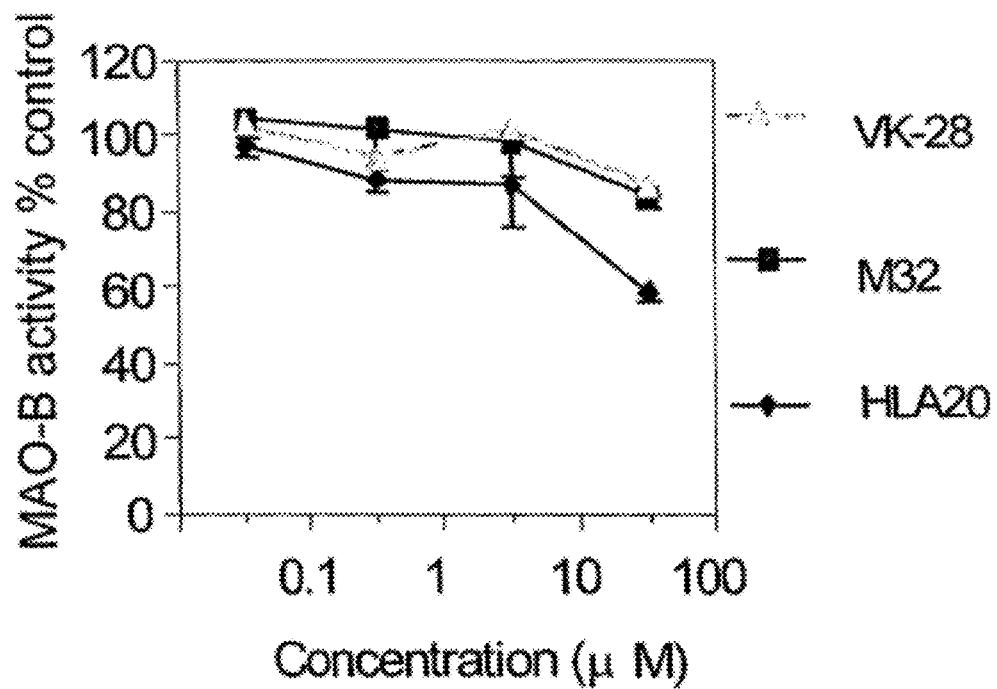
FIGS. 5A-5D are graphs showing the in vitro inhibitory action of HLA20 and M32 (FIG. 5A), M30 and M31 (FIG. 5B), VK-28, and propargylamine (P) against rat brain MAO-B, and of M31 (FIG. 5C), M32 and HLA20 (FIG. 5D), VK-28, and propargylamine (P) against rat brain MAO-B and MAO-A.
Figure 5B:
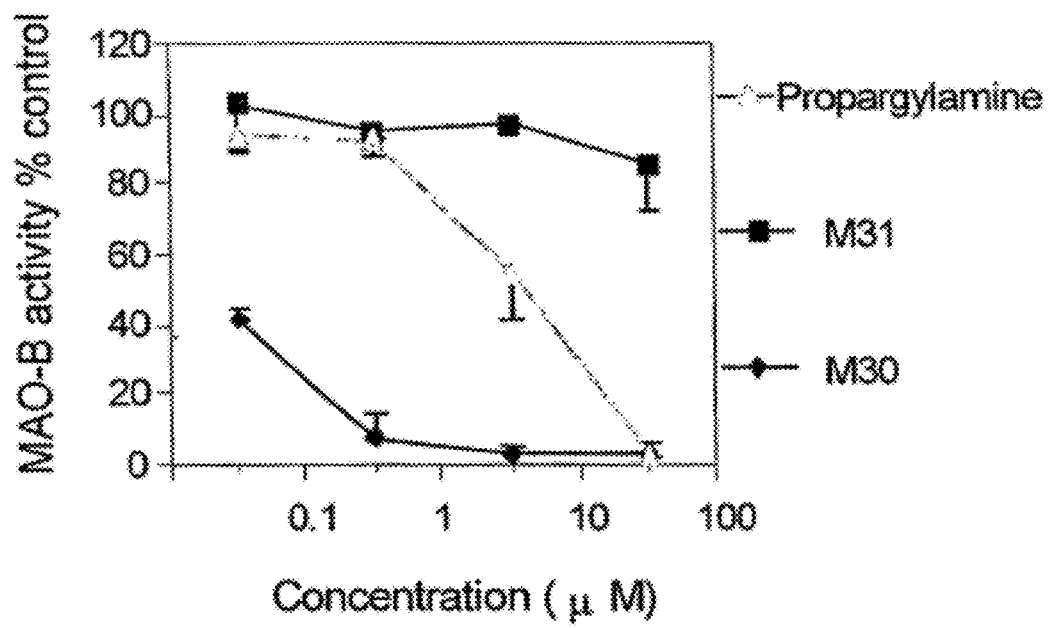

In one experiment, the in vitro inhibitory activity of HLA20, M32, VK-28, M30, M31, and propargylamine (P) was tested against rat brain MAO-B. The test compounds were added to buffer containing $10^{-7}$M clorgylin and were incubated with the tissue homogenate for 60 min at 37° C. before addition of $^{14}$C-β-phenyl-ethylamine. The results are shown in FIGS. 5A-5B. MAO-B activity in presence of the test compound was expressed as a percentage of that in control samples. Mean values shown±s.e.mean.

Figure 5C:
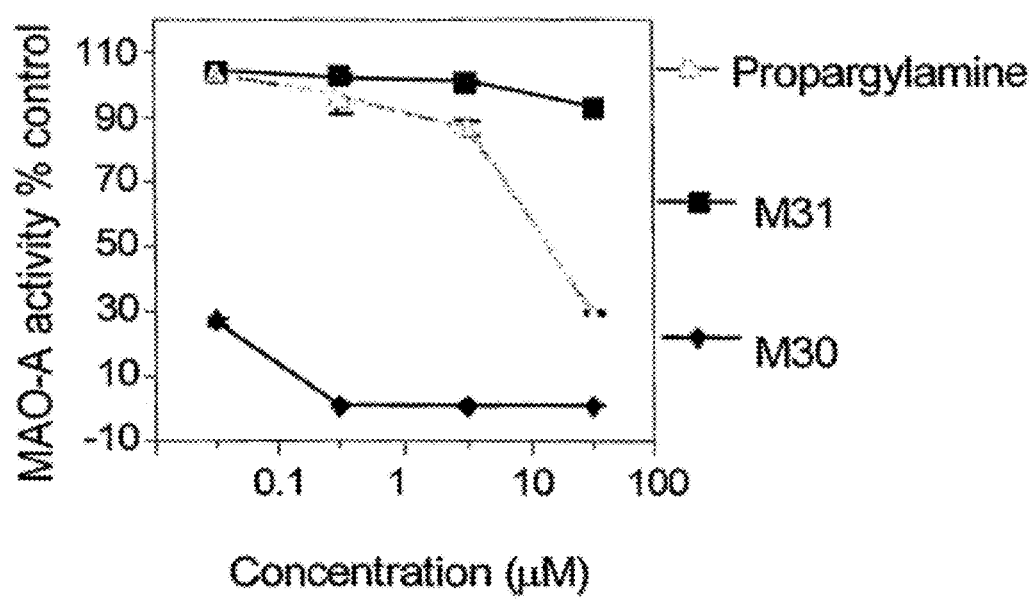
Figure 5D:
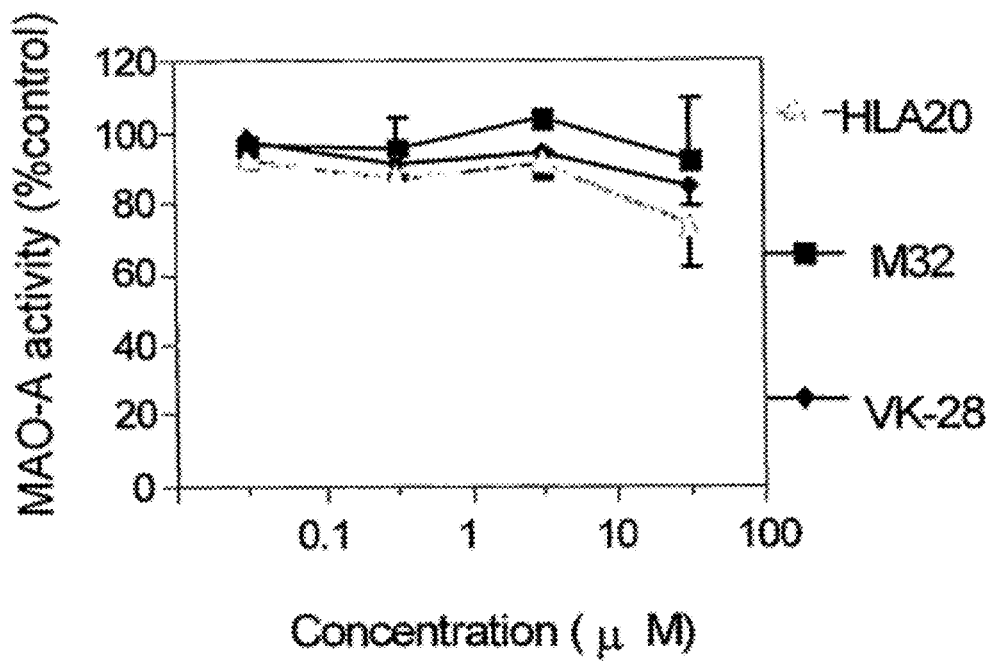

In another experiment, the in vitro inhibitory activity of HLA20, M32, VK-28, M30, M31, and propargylamine (P) was tested against rat brain MAO-A. The test compounds were added to buffer containing $10^{-7}$M deprenyl and were incubated with the tissue homogenate for 60 min at 37° C. before addition of $^{14}$C-5-hydroxytryptamine. The results are shown in FIGS. 5C-5D. MAO-A activity in presence of the test compound was expressed as a percentage of that in control samples. Mean values shown±s.e.mean.

These experimental results showed that there were distinct differences in the inhibitory activities among the test compounds. While iron chelator M30 caused a significant inhibition of both MAO-A and MAO-B activities with the $IC_{50}$ values less than 0.1 µM, chelators M32 and M31 had almost no effect on MAO-A and poor inhibitory effect on MAO-B activity (17.2% and 14.2% inhibition at 100 µM, respectively). VK-28 and HLA20 showed similar mild inhibitory activities on MAO-A (15.1% and 26.1% inhibition at 100 µM, respectively), but on MAO-B activity HLA20 exhibited more potent inhibitory effect than that of VK-28 (42.0% inhibition for HLA20 and 13.3% for VK-28). Propargylamine (P) preferentially inhibited both MAO-A and MAO-B activities in a concentration-dependent manner, with the $IC_{50}$ values 66.3 µM and 10.1 µM, respectively.

Example 35

Transport Property of the Chelators

Lipophilicity plays an important role in drug absorption and distribution. The logarithm of the n-octanol/water distribution coefficients (logD) is the most commonly used measure of the lipophilicity of a drug candidate. Here we used an n-octanol/water shake-flask procedure to determine logD. The results (Table 1) indicated that the distribution coefficients (logD) of the test chelators varied greatly with pH values and the compounds tested. In acidic and basic solution, all the test compounds have low log D values, which refer to a good hydrophilicity. This can be explained by the formation of oxinium chloride (in acid) and sodium oxinate (in base) derivatives. Table 1 shows the order of the lipophilicity of the chelators in water: HLM7 (2.19)>HLA16 (1.79)>HLA20 (1.57)>HLM9 (−1.70)>HLM8 (<−2). These data suggest that HLM9 and HLM8 may have a poor permeability through biological membranes due to their highly hydrophilicity; on the other hand, HLM7 HLA16, and HLA20, because of their lipid solubility, may be able to cross biological membranes.

TABLE 1

Distribution coefficients of the chelators at different pH values

| Compounds | D[a] | | | LogD | | |
|---|---|---|---|---|---|---|
| | in 0.01N HCl | in H2O | in 0.01N NaOH | in 0.01N HCl | in H2O | in 0.01N NaOH |
| HLA16 | 0.018 | 62.96 | 2.44 | −1.74 | 1.79 | 0.39 |
| HLM7 | 0.043 | 155.68 | 0.097 | −1.37 | 2.19 | −1.01 |
| HLM8 | 0.0031 | 0.0049 | 0.020 | <−2[c] | <−2[c] | −1.70 |
| HLM9 | 0.038[b] | 0.018 | 0.0014 | −1.42[b] | −1.70 | <−2[c] |
| HLA20 | 0.025 | 37.02 | 0.70 | −1.60 | 1.57 | −0.16 |

[a]Distribution ratios D = $C_{org}/C_{aq}$ for different compounds, where $C_{org}$ and $C_{aq}$ are concentrations of the measured compound in organic and in aqueous phase respectively.
[b]D was measured in phosphate buffer (pH = 5.64).
[c]These compounds were found to have Log D values below −2. Since such values are not considered reliable no exact values are given.

Example 36

Inhibition of Lipid Peroxidation in Brain Mitochondrial Fraction

Figure 6:
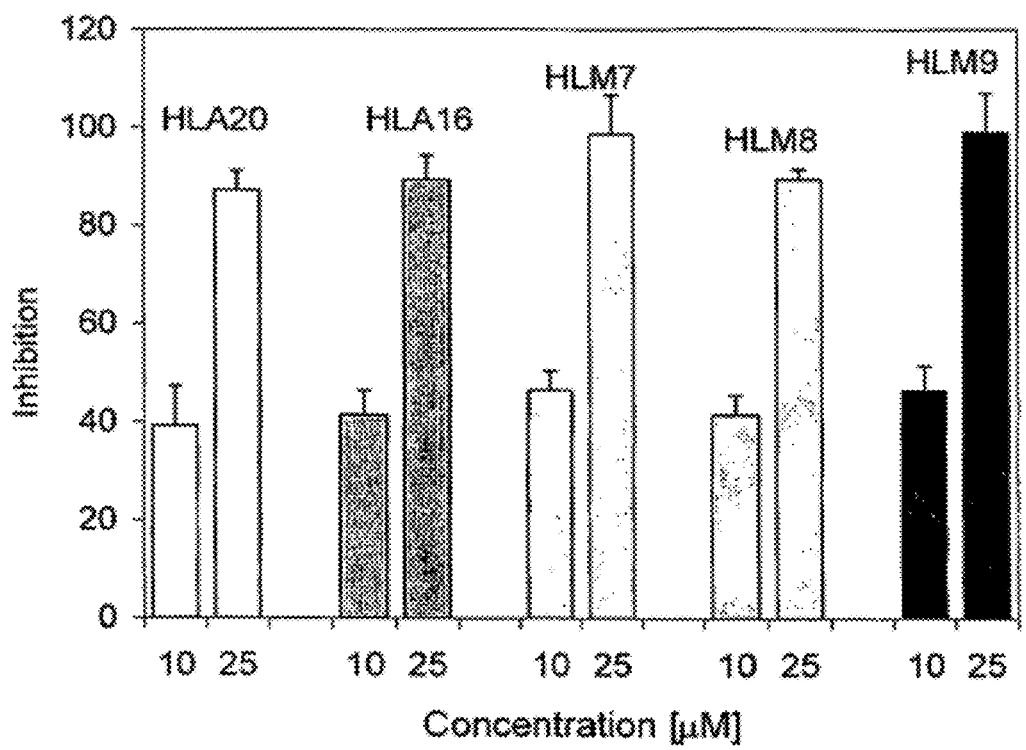
FIG. 6 shows inhibition of lipid peroxidation by the chelators of the invention HLM7, HLM8, HLM9, HLA16 and HLA20 in the presence of 5.0 μM $Fe_2SO_4$/50 μM ascorbic acid. The results are the mean±SEM, n=3, p<0.05.

The radical scavenging/antioxidant properties of the novel chelators were determined by the lipid peroxidation assay. This system has been used to measure the ability of antioxidants to protect biological lipid from free radical damage. In the present work, formation of MDA in the mitochondria was induced with 50 μM ascorbic acid and 5 μM $FeSO_4$. As shown in FIG. 6, all the chelators tested inhibited lipid peroxidation. This inhibition was dose-dependent. The remarkable inhibitory effects were observed with all the chelators at 25 μM, reducing radical damage by 90% to 97%. At compound concentration as low as 10 μM these chelators significantly reduced radical formation (about 40% inhibition). This inhibition may be attributed to radical scavenging and iron chelating properties of the test compounds.

Example 37

Topical Photoprotection

In order to determine the level of topical photoprotection provided by the iron chelators of the invention, guinea pigs are treated topically with the test compound, and are then exposed to varying doses of UV radiation to determine the sun protection factor (SPF). Hairless mice are treated topically with the test compound and then subjected to long-term exposure to a suberythemal dose of UV radiation. The mice are evaluated for skin wrinkling and skin tumors.

In another experiment, guinea pigs are treated topically with the test compound, sunscreen, and a combination of the two and are then exposed to varying doses of UV radiation to determine the sun protection factor (SPF). Hairless mice are treated topically with the test compound, sunscreen, and a combination of the two and then subjected to long-term exposure to a suberythemal dose of UV radiation. The mice are evaluated for skin wrinkling and skin tumors.

REFERENCES

Andrews F J, Morris C J, Kondratowicz G, Blake D R. (1987) "Effect of iron chelation on inflammatory joint disease". Ann Rheum Dis. 46(4):327-33.

Ben-Shachar, D, Eshel, G, Finberg, J P and Youdim, M B. (1991). "The iron chelator desferrioxamine (Desferal) retards 6-hydroxydopamine-induced degeneration of nigrostriatal dopamine neurons." J Neurochem, 56:1441-1444.

Bissett D L, McBride J F. (1996) "Synergistic topical photoprotection by a combination of the iron chelator 2-furildioxime and sunscreen". J Am Acad Dermatol. 35(4):546-9.

Breuer, W., Epsztejn, S., Millgram, P., Cabantchik, I Z. (1995) "Transport of iron and other transition metals into cells as revealed by a fluorescent probe". Am J. Physiol. 268(6 Pt 1):C1354-61.

Buss J L, Torti F M, Torti S V. (2003) "The role of iron chelation in cancer therapy". Curr Med Chem 10(12):1021-34.

Butterfield D A, Howard B J, LaFontaine M A. (2001) "Brain oxidative stress in animal models of accelerated aging and the age-related neurodegenerative disorders, Alzheimer's disease and Huntington's disease". Curr Med. Chem. 8(7): 815-28.

Crivori, P.; Cruciani, G.; Carrupt, P. A.; Testa, B. (2000) "Predicting Blood-Brain Barrier Permeation from Three-Dimensional Molecular Structure". J. Med. Chem., 43: 2204-2216.

Cuajungco, M P, Faget, K Y, Huang, X, Tanzi, R E and Bush, A I. (2000) "Metal chelation as a potential therapy for Alzheimer's disease". Ann.N.Y. Acad. Sci. 920:292-304.

Flaherty J T, Zweier J L. (1991) "Role of oxygen radicals in myocardial reperfusion injury: experimental and clinical evidence". Klin Wochenschr. 69(21-23):1061-5.

Gassen, M and Youdim M B. (1999) "Free radical scavengers: chemical concepts and clinical relevance". J Neural Transm Suppl. 56:193-210.

Gassen, M., Gross, A. and Youdim, M B. (1998) "Apomorphine enantiomers protect cultured pheochromocytoma (PC 12) cells from oxidative stress induced by $H_2O_2$ and 6-hydroxydopamine." Movement Disorders 13:242-248.

Gassen, M and Youdim M B. (1997) "The potential role of iron chelators in the treatment of Parkinson's disease and related neurological disorders." Pharmacol Toxicol. 80(4): 159-66.

Gassen, M., Glinka, Y., Pinchasi, B., Youdim, M B (1996) "Apomorphine is a highly potent free radical scavenger in rat brain mitochondrial fraction". Eur. J. Pharmacol. 308 (2): 219-25.

Gozes I, Pert O, Giladi E, Davidson A, Ashur-Fabian O, Rubinraut S, Fridkin M. (1999) "Mapping the active site in vasoactive intestinal peptide to a core of four amino acids: neuroprotective drug design." Proc Natl Acad Sci USA. 96(7):4143-8.

Hershko C. (1994) "Control of disease by selective iron depletion: a novel therapeutic strategy utilizing iron chelators". Eur J Biochem 270(8): 1689.

Hershko C, Pinson A, Link G. (1996) "Prevention of anthracycline cardiotoxicity by iron chelation". Acta Haematol. 95(1):87-92.

Hewitt S D, Hider R C, Sarpong P, Morris C J, Blake D R. (1989) "Investigation of the anti-inflammatory properties of hydroxypyridinones". Annals of Rheum Diseases 48:382-388.

Kitazawa M, Iwasaki K. (1999) "Reduction of ultraviolet light-induced oxidative stress by amino acid-based iron chelators". Biochim Biophys Acta. 27; 1473(2-3):400-8.

Kontoghiorghes G J. (2001) "Clinical use, therapeutic aspects and future potential of deferiprone in thalassaemia and other conditions of iron and other metal toxicity". Drugs of Today Vol. 37, pages 23-35.

Ostrakhovitch E A, Afanas'ev I B. (2001) "Oxidative stress in rheumatoid arthritis leukocytes: suppression by rutin and other antioxidants and chelators". Biochem Pharmacol. 62(6): 743-6.

Podda M, Grundmann-Kollmann M. (2001) "Low molecular weight antioxidants and their role in skin ageing". Clin Exp Dermatol. 26(7):578-82.

Polla A S, Polla L L, Polla B S. (2003) "Iron as the malignant spirit in successful ageing". Ageing Res Rev 2(1):25-37.

Roza A M, Slakey D P, Pieper G M, Van Ye T M, Moore-Hilton G, Komorowski R A, Johnson C P, Hedlund B E, Adams M B. (1994) "Hydroxyethyl starch deferoxamine, a novel iron chelator, delays diabetes in BB rats". J Lab Clin Med. 123(4):556-60.

Sawahara H, Goto S, Kinoshita N. (1991) "Double fluorescent labeling method used for a study on liposomes". Chem Pharm Bull (Tokyo) 39(1):227-9.

Sayre, L M, Perry, G, Atwood, C S and Smith, M A. (2000) "The role of metals in neurodegenerative diseases". Cell. Mol. Biol. 46:731-741.

van Asbeck B S, Georgiou N A, van der Bruggen T, Oudshoorn M, Nottet H S, Marx J J. (2001) "Anti-HIV effect of iron chelators: different mechanisms involved". J Clin Virol 20(3):141-7.

Vile G F, Tyrrell R M. (1995) "UVA radiation-induced oxidative damage to lipids and proteins in vitro and in human skin fibroblasts is dependent on iron and singlet oxygen". Free Radic Biol Med 18(4):721-30.

Yogev-Falach M, Amit T, Bar-Am O, Youdim M B. (2003) "The importance of propargylamine moiety in the anti-Parkinson drug rasagiline and its derivatives for MAPK-dependent amyloid precursor protein processing." FASEB J. 2003 Oct. 2 [Epub ahead of print].

APPENDIX I

| code name | M6A | M7A | M8A |
|---|---|---|---|
| another name | StKKC(HQ-Pr)L | Fmoc-KKC(HQ-Pr)L | [L-Cys$^5$(HQ-Pr)]GnRH |
| structure | StearylKKCLNH2 | FmocKKCLNH2 | [L-Cys$^5$]GnRH |

| code name | M18A | M19A |
|---|---|---|
| another name | YGGC(HQ-Pr)L | YGGC(HQ-Pr)M |
| structure | Tyr-Gly-Gly-Cys-Leu-OH | Tyr-Gly-Gly-Cys-Met-OH |

| code name | M20A | M21A | M22A |
|---|---|---|---|
| another name | C(HQ-Pr)GGFL | C(HQ-Pr)GGFM | [D-Cys$^5$(HQ-Pr)]GnRH |
| structure | HO-Leu-Phe-Gly-Cys | HO-Met-Phe-Gly-Gly-Cys | [D-Cys$^5$]GnRH |

APPENDIX I-continued

| code name | M27A | M28A |
|---|---|---|
| structure | [Cys⁷(HQ)]-Substance-P 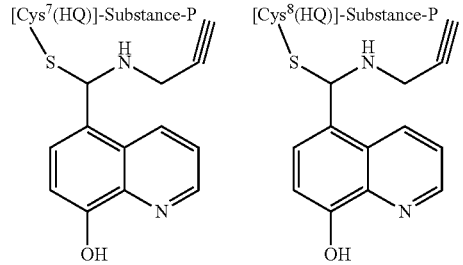 | [Cys⁸(HQ)]-Substance-P 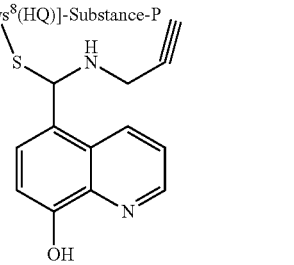 |

APPENDIX II

| code name | M6 | M7 | M8 |
|---|---|---|---|
| another name | StKKC(HQ)L | Fmoc-KKC(HQ)L | [L-Cys⁵(HQ)]GnRH |
| structure | StearylKKCLNH2 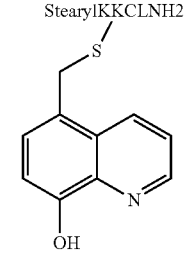 | FmocKKCLNH2 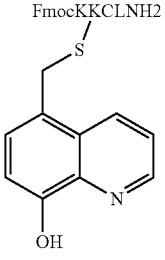 | [L-Cys⁵]GnRH 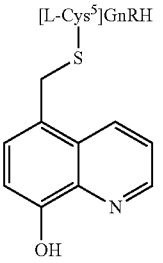 |

| code name | M11 | M12 | M18 |
|---|---|---|---|
| another name | D-HQ-CysOH | L-HQ-CysOH | YGGC(HQ)L |
| structure | 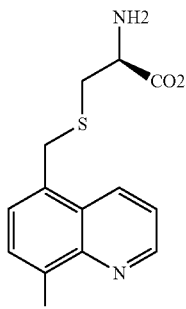 | 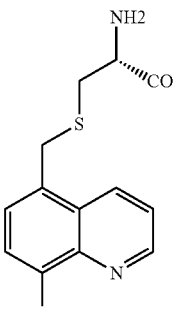 | Tyr-Gly-Gly-Cys-Leu-OH 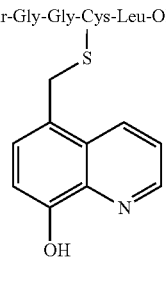 |

| code name | M19 | M20 | M21 |
|---|---|---|---|
| another name | YGGC(HQ)M | C(HQ)GGFL | C(HQ)GGFM |
| structure | Tyr-Gly-Gly-Cys-Met-OH 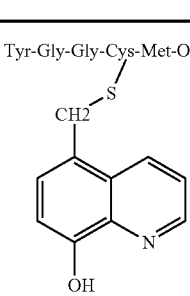 | Cys-Gly-Gly-Phe-Leu-OH 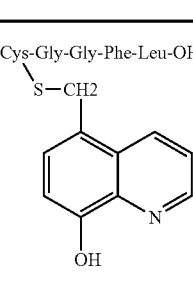 | Cys-Gly-Gly-Phe-Met-OH 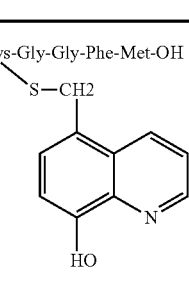 |

APPENDIX II-continued
| code name | M22 | M27 | M28 |
|---|---|---|---|
| another name | [D-Cys6(HQ)]GnRH | ([Cys7(HQ)]-Substance-P | [Cys8(HQ)]-Substance-P |
| structure | [D-Cys8]GnRH | [Cys7]-Substance-P | [Cys8]-Substance-P |
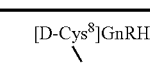
APPENDIX III
| code name | HLA16a | HLA20 | M9a |
|---|---|---|---|
| another name | | | D-(HQ-Pr)-Ala |
| code name | M11a | M12a | M13a |
|---|---|---|---|
| another name | D-(HQ-Pr)-CysOH | L-(HQ-Pr)-CysOH | |
| code name | M15a | M17 | M30 |
|---|---|---|---|
| another name | | | |
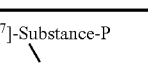
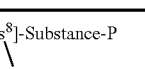

APPENDIX III-continued
| code name | M31 | M33 | M34 |
|---|---|---|---|
| another name | | | |
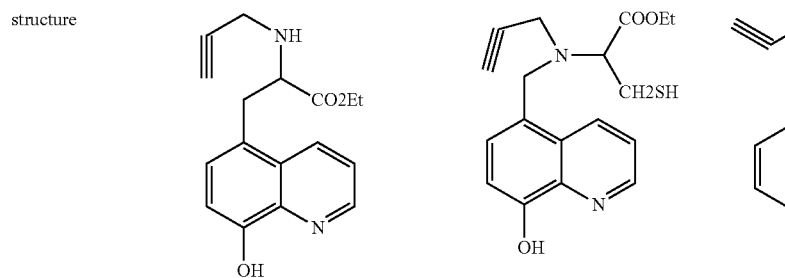
| code name | M10a |
| --- | --- |
| another name | L-(HQ-Pr)-Ala |
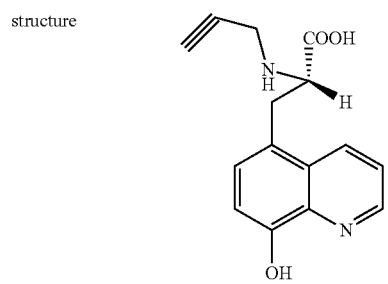
APPENDIX IV
| code name | VK-28 | HLA16 | HLM7 |
|---|---|---|---|
| another name | | HQPCOOEt | |
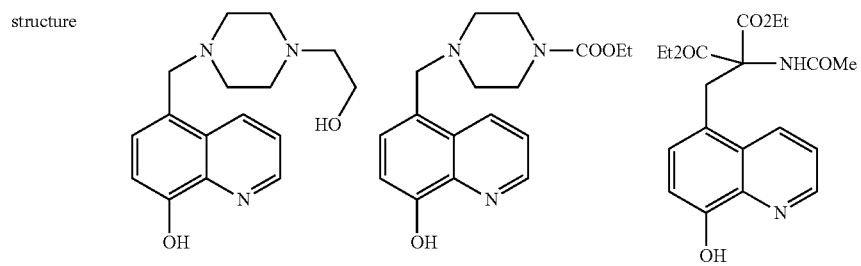
| code name | HLM8 | HLM9 | M9 |
|---|---|---|---|
| another name | HQAla | HQAlaEt | D-HQ-Ala |
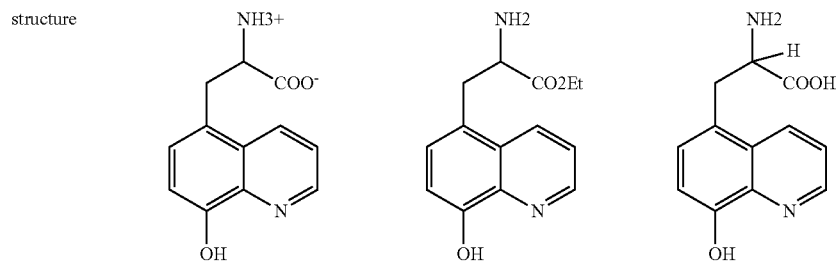

APPENDIX IV-continued

| code name | M10 | M11B | M12B |
|---|---|---|---|
| another name | L-HQ-Ala | | |
| structure | (8-hydroxyquinolin-5-yl)methyl-substituted alanine with NH2 and COOH | Fmoc-NH, CO2H, S-CH2-(8-hydroxyquinolin-5-yl) | Fmoc-NH, CO2H, S-CH2-(8-hydroxyquinolin-5-yl) (wavy bond) |

| code name | M13 | M15 | M32 |
|---|---|---|---|
| structure | Me, NH-NH2, COOH, CH2-(8-hydroxyquinolin-5-yl) | HN-NH-C(O)-CH(NH2)-CH2OH attached via ethyl to 8-hydroxyquinolin-5-yl | CO2Et, NH-CH(CH2SH)-, CH2-(8-hydroxyquinolin-5-yl) |

APPENDIX V

| code name | M6B | M7B | M8B |
|---|---|---|---|
| structure | StearylKKCLNH2-S-CH2-C(O)-N(CH2-C≡CH)(CH2)n-CONHOH | FmocKKCLNH2-S-CH2-C(O)-N(CH2-C≡CH)(CH2)n-CONHOH | [L-Cys$^5$]GnRH-S-CH2-C(O)-N(CH2-C≡CH)(CH2)n-CONHOH |

| code name | M18B | M19B | M20B |
|---|---|---|---|
| structure | Tyr-Gly-Gly-Cys-Leu-OH-S-CH2-C(O)-N(CH2-C≡CH)(CH2)n-CONHOH | Tyr-Gly-Gly-Cys-Met-OH-S-CH2-C(O)-N(CH2-C≡CH)(CH2)n-CONHOH | HO-Leu-Phe-Gly-Cys-S-CH2-C(O)-N(CH2-C≡CH)(CH2)n-CONHOH |

APPENDIX V-continued

| code name | M21B | M22B | M27B |
|---|---|---|---|
| structure | HO-Met-Phe-Gly-Gly-Cys (structure with S, C=O, N, (CH₂)n, CONHOH, propargyl) | [D-Cys⁶]GnRH (structure with S, C=O, N, (CH₂)n, CONHOH, propargyl) | [Cys⁷]-Substance-P (structure with S, C=O, N, (CH₂)n, CONHOH, propargyl) |

| code name | M28B | M35 | M36 |
|---|---|---|---|
| structure | [Cys⁸]-Substance-P (structure with S, C=O, N, (CH₂)n, CONHOH, propargyl) | structure with CONHOH, (CH₂)n, N, propargyl, O, O-benzyl | structure with HOHNOC, (CH₂)n, OCOCH₃, CON, HC-COOEt, CH₂SH, benzene ring, NH, allyl |

| code name | M36a | M37 | M38 |
|---|---|---|---|
| structure | COOH, (CH2)n, HN, CONHOH, propargyl | HN, CH2, CONHOH, propargyl | structure with O, N-piperazine-N-CH3, CH2, CONHOH, propargyl |

| code name | M39 | M40 | M41 |
|---|---|---|---|
| structure | O, N, piperazine-N-CH2CH2OH, CH2, CONHOH, propargyl | O, N, piperazine-N-COOEt, CH2, CONHOH, propargyl | O, N, CH2-phenyl-OH, CH2, CONHOH, propargyl |

| code name | M42 | M43 | M44 |
|---|---|---|---|
| structure | COCH₂-N-piperazine-N-CH2CH2OH, N, (CH₂)n, CONHOH, propargyl | O, N, CH2-phenyl-OH, CH2, CONHOH, propargyl | COCH2-N-piperazine-N-propargyl, N-(CH2)n-CONHOH, CH2, SH, COOEt |

APPENDIX V-continued

| code name | M45 | M46 |
|---|---|---|
| structure | (chemical structure) | (chemical structure) |

APPENDIX VI

| code name | M9b | M11b | M12b |
|---|---|---|---|
| structure | (chemical structure) | (chemical structure) | (chemical structure) |

| code name | M13b | M15b | HLA16b |
|---|---|---|---|
| structure | (chemical structure) | (chemical structure) | (chemical structure) |

| code name | M17a | HLA20a | M30a |
|---|---|---|---|
| structure | (chemical structure) | (chemical structure) | (chemical structure) |

APPENDIX VI-continued
| code name | M31a | M33a | M34b |
|---|---|---|---|
| structure | 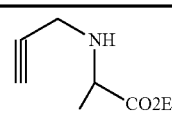 | | |
| APPENDIX VII | | APPENDIX VII-continued | |
|---|---|---|---|
| 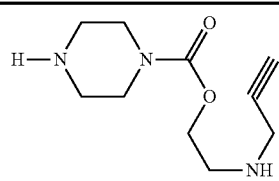 | H1 | 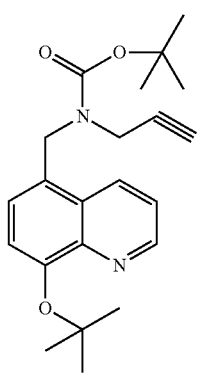 | H5 |
| 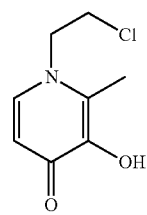 | H2 | | |
| 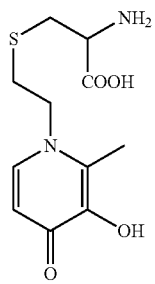 [SMILES: Cc1c(O)c(=O)ccn1CCSCC(N)C(=O)O] | H3 | | |
| 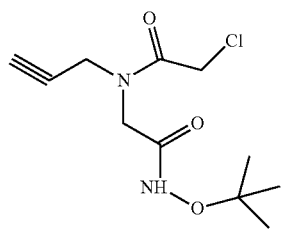 [SMILES: C#CCN(CC(=O)NOC(C)(C)C)C(=O)CCl] | H4 | 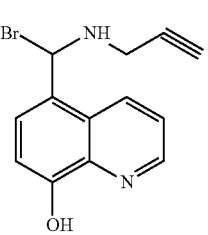 [SMILES: C#CCNC(Br)c1ccc(O)c2ncccc12] | H6 |

The invention claimed is:

1. A method for treatment of a neurodegenerative or cerebrovascular disease, condition or disorder, which comprises administering to an individual in need thereof an effective amount of a compound of formula I to IV or a pharmaceutically acceptable salt thereof:

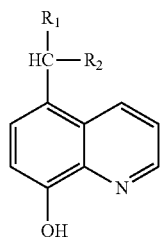

I

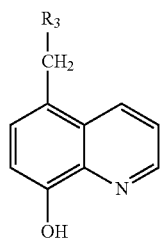

II

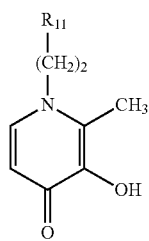

IV wherein $R_1$ is a residue of an analog of a neuroprotective peptide, or of a fragment thereof, containing a cysteine residue that is linked to the C atom via the —S— atom of the L- or D-Cys residue, and wherein the amino terminal of the peptide is unsubstituted or substituted by a hydrophobic group;

$R_2$ is, NH—X;

$R_3$ is a group selected from the group consisting of —NH—$CH_2$—$CH_2$—NH—$R_4$,

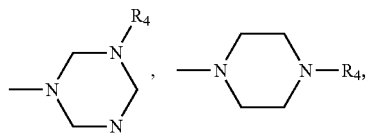

—$CR_5R_6R_7$, —N($CH_3$)—X, —N($R_8$)—CH($CH_2$SH)COO$C_2H_5$, —N($R_8$)—$CH_2$—COO$CH_2C_6H_5$, and —S—$CH_2$—CH(COOH)—NH$R_8$';

$R_4$ is a group selected from the group consisting of X, COO$C_2H_5$, $(CH_2)_2$—O—$R_8$, and —COO—$(CH_2)_2$—NH—$R_8$;

$R_5$ is H, $C_1$-$C_4$ lower alkyl or COO$C_2H_5$;

$R_6$ is H, COOH, COO— or COO$C_2H_5$;

$R_7$ is selected from the group consisting of —NH—$R_8$, NH—COCH—NH—NH—$R_8$, and —NH—NH—CO—CH($CH_2$OH)—NH—$R_8$;

$R_8$ is X; $R'_8$ is X;

—CO—$CH_2$ $R_{12}$——CO—$CH_2$—CO—$CH_2$ $R_{11}$ is a group selected from the group consisting of
(i) —S—$CH_2$—CH(COOH)—NH—X;
(ii) —N(X)—$CH_2$COO—$CH_2$—$C_6H_5$;
(iii) —N($CH_3$)—X;
(iv) —N(X)—CH($CH_2$SH)COO$C_2H_5$;
(v) —$CH_2$—NH—NH—CO—CH($CH_2$OH)—NH—X;

(vi) —C(CH₃)(COOH)—NH—NH—X;
(vii) —CH(COOH)—NH—X;
(viii) —CH(COOC₂H₅H)—NH—X; and

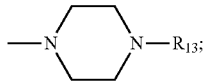
(ix)

R₁₂ is X, C₁-C₄ lower alkyl, COOC₂H₅ or —(CH₂)₂—OH—;

R₁₃ is X, —CH₂)₂—OX—, or —COO—(CH₂)₂—NH—X; and

X is a propargyl group.

2. The method according to claim 1, wherein said compound is a compound of the formula I:

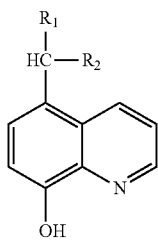
I or a pharmaceutically acceptable salt thereof wherein

R₁ is an analog of a neuroprotective peptide selected from the group consisting of vasoactive intestinal peptide (VIP), gonadotropin-releasing hormone (GnRH), Substance P and enkephalin or a fragment thereof, in which one amino acid residue has been replaced by a L- or D-cysteine residue, said analog is linked to the C atom via the —S— atom of the Cys residue, and the amino terminal of said peptide or fragment thereof is unsubstituted or substituted by a hydrophobic group;

R₂ is —NH—X; and

X is a propargyl group.

3. The method according to claim 2, wherein said compound of formula I, is selected from the group consisting of:

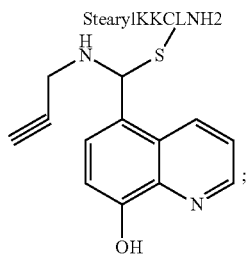
M6A

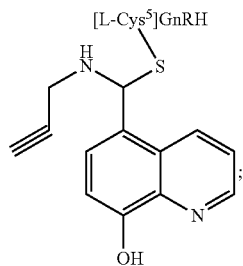
M7A

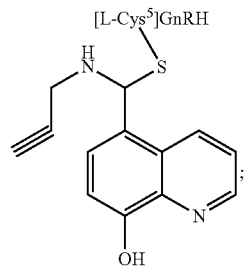

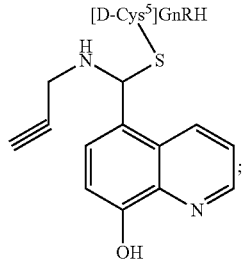
M22A

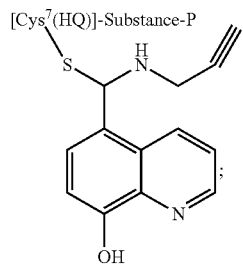
M27A

M28A 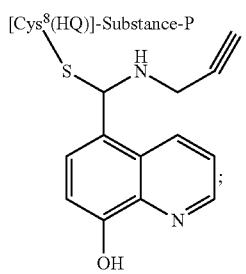
M19A 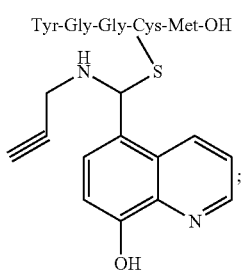
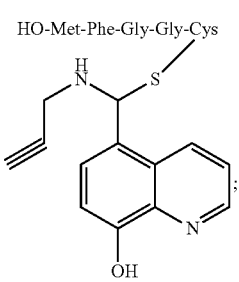
M18A 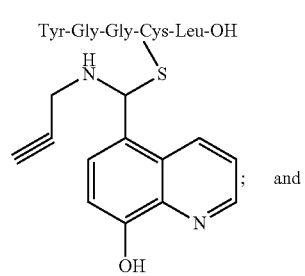; and
M20A 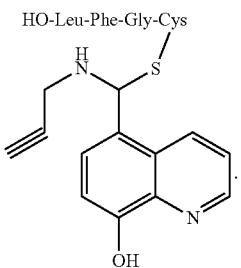
4. The method according to claim 1, wherein said compound is a compound of the formula II or a pharmaceutically acceptable salt thereof.
5. The method according to claim 4, wherein, in the compound of formula II, $R_3$ is:
(i) a piperazine ring, and the compound is HLA16a, M17, or HLA20:
HLA16a 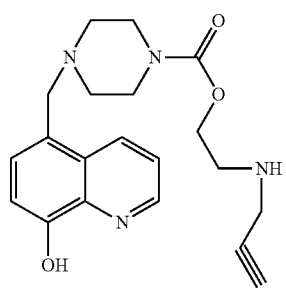
M17 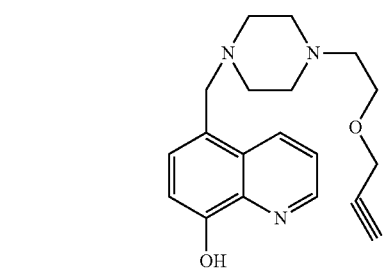
HLA20 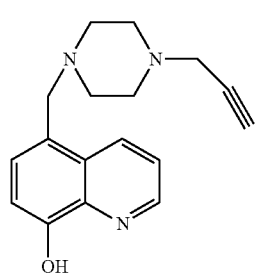

(ii) —S—CH$_2$—CH(COOH)—NHR$_8$' wherein

R$_8$' is propargyl, and the compound is M11a or M12a

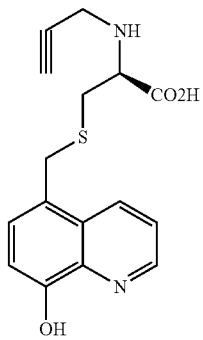
M11a

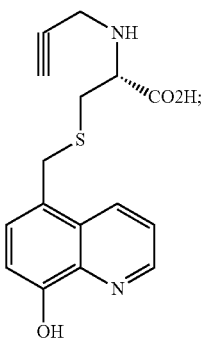
M12a (iii) —CR$_5$R$_6$R$_7$, wherein (a) R$_5$ is H, R$_6$ is COOH, R$_7$ is —NH—R$_8$, and
or R$_8$ is propargyl and the compound is M9a or M10a:

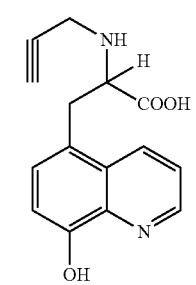
M9a

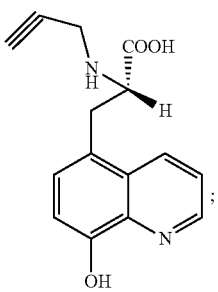
M10a (b)

or R$_5$ is H, R$_6$ is COOC$_2$H$_5$ and R$_7$ is —NH-propargyl and the compound is M31:

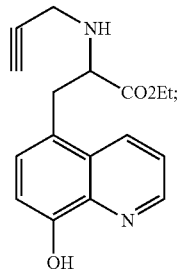
M31

(iv) —NR$_8$—CH(CH$_2$SH)COOC$_2$H$_5$, wherein
R$_8$ is propargyl and the compound is M33:

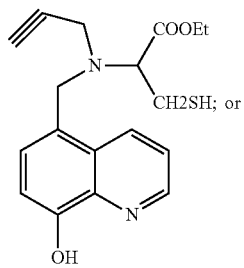
M33

(v) —N(CH$_3$)-propargyl and the compound is M30:

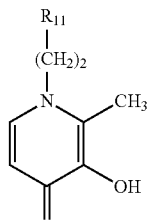
M30

6. The method according to claim 1, wherein said compound is a compound of formula IV or a pharmaceutically acceptable salt thereof:

IV wherein R$_{11}$ is as defined in claim 1.

7. The method according to claim 1, wherein said disease, condition or disorder is a neurodegenerative disease selected from the group consisting of Parkinson's disease and Alzheimer's disease.

8. The method according to claim 1, wherein said disease, condition or disorder is stroke.

9. The method according to claim 6, wherein said compound is selected from the group consisting of:
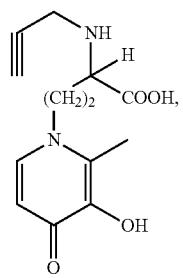
M9b
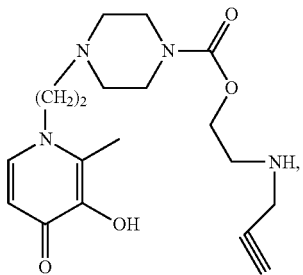
HLA16b
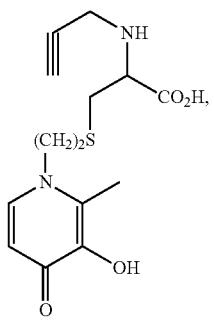
M11b
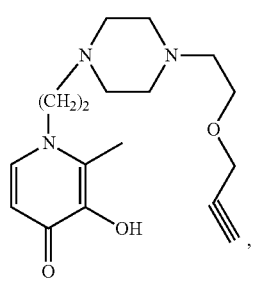
M17a
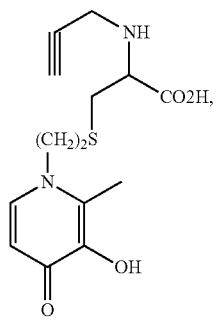
M12b
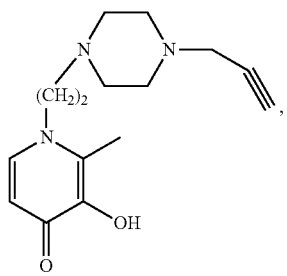
HLA20a
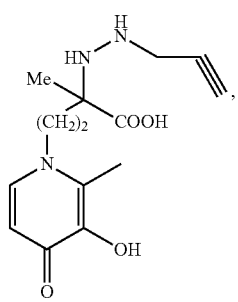
M13b
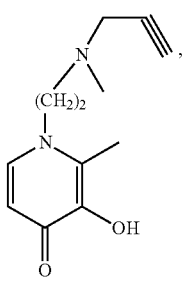
M30a
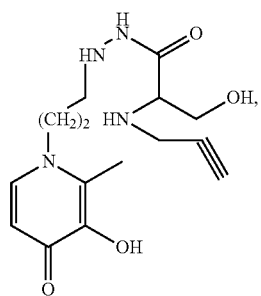
M15b
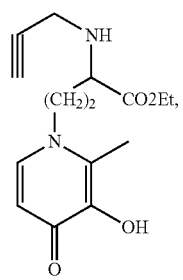
M31a M33a
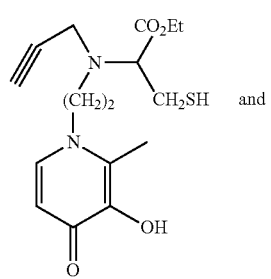 and
M34b
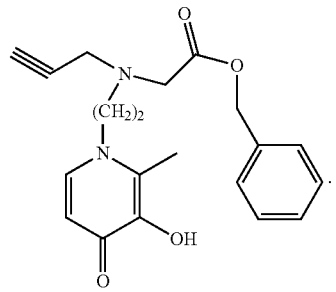.
* * * * *

SEQUENCE LISTING
<160> NUMBER OF SEQ ID NOS: 14
<210> SEQ ID NO 1
<211> LENGTH: 4
<212> TYPE: PRT
<213> ORGANISM: Artificial Sequence
<220> FEATURE:
<223> OTHER INFORMATION: Synthetic peptide: a segment of vasoactive

```
            intestinal peptide (VIP). Lys (position 1) is bound to Stearyl.
            Leu (position 4) is amidated.

<400> SEQUENCE: 1

Lys Lys Tyr Leu
1

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide: a modification of peptide of
      SEQ ID NO: 1. Lys (position 1) may be bound to stearyl or Fmoc.
      Leu (position 4) is amidated.

<400> SEQUENCE: 2

Lys Lys Cys Leu
1

<210> SEQ ID NO 3
<211> LENGTH: 10
<212> TYPE: PRT
<213> ORGANISM: Human
<220> FEATURE:
<221> NAME/KEY: MOD_RES
<222> LOCATION: (1)..(10)
<223> OTHER INFORMATION: Natural gonadotropin-releasing hormone (GnRH).
      Pro (position 1) is 5-oxo-Pro. Gly (position 10) is amidated.

<400> SEQUENCE: 3

Pro His Trp Ser Tyr Gly Leu Arg Pro Gly
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic peptide: a modification of the GnRH
      peptide of SEQ ID NO:3. Pro (position 1) is 5-oxo-Pro.Gly
      (position 10) is amidated

<400> SEQUENCE: 4

Pro His Trp Ser Cys Gly Leu Arg Pro Gly
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic peptide: a modification of the GnRH
      peptide of SEQ ID NO: 3. Pro (position 1) is 5-oxo-Pro. Cys
      (position 6) is D-Cys. Gly (position 10) is amidated.

<400> SEQUENCE: 5

Pro His Trp Ser Tyr Cys Leu Arg Pro Gly
1               5                   10

<210> SEQ ID NO 6
<211> LENGTH: 11
<212> TYPE: PRT
<213> ORGANISM: Human
<220> FEATURE:
<221> NAME/KEY: MOD_RES
<222> LOCATION: (11)..(11)
<223> OTHER INFORMATION: Natural Substance P peptide. Met (position 11)
      is amidated.
```

```
<400> SEQUENCE: 6

Arg Pro Lys Pro Gln Gln Phe Phe Gly Leu Met
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic peptide: a modification of Substance
      P peptide of SEQ ID NO: 6. Met (position 11) is amidated.

<400> SEQUENCE: 7

Arg Pro Lys Pro Gln Gln Cys Phe Gly Leu Met
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic peptide: a modification of Substance
      P peptide of SEQ ID NO: 6. Met (position 11) is amidated.

<400> SEQUENCE: 8

Arg Pro Lys Pro Gln Gln Phe Cys Gly Leu Met
1               5                   10

<210> SEQ ID NO 9
<211> LENGTH: 5
<212> TYPE: PRT
<213> ORGANISM: Human

<400> SEQUENCE: 9

Tyr Gly Gly Phe Met
1               5

<210> SEQ ID NO 10
<211> LENGTH: 5
<212> TYPE: PRT
<213> ORGANISM: Human

<400> SEQUENCE: 10

Tyr Gly Gly Phe Leu
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic peptide: a modification of
      Met(5)-enkephalin peptide of SEQ ID NO: 9.

<400> SEQUENCE: 11

Tyr Gly Gly Cys Met
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic peptide: a modification of
      Met(5)-enkephalin peptide of SEQ ID NO: 9.

<400> SEQUENCE: 12
```

```
Cys Gly Gly Phe Met
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic peptide: a modification of
      Leu(5)-enkephalin peptide of SEQ ID NO: 10.

<400> SEQUENCE: 13

Tyr Gly Gly Cys Leu
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic peptide: a modification of
      Leu(5)-enkephalin peptide of SEQ ID NO: 10.

<400> SEQUENCE: 14

Cys Gly Gly Phe Leu
1               5
```